US012807940B2

(12) United States Patent
Mali et al.

(10) Patent No.: US 12,807,940 B2
(45) Date of Patent: Nov. 24, 2026

(54) GENE FRAGMENT OVEREXPRESSION SCREENING METHODOLOGIES, AND USES THEREOF

(71) Applicant: The Regents of the University of California, Oakland, CA (US)

(72) Inventors: Prashant Mali, La Jolla, CA (US); Kyle M. Ford, La Jolla, CA (US); Nathan Palmer, La Jolla, CA (US); Rebecca Panwala, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 895 days.

(21) Appl. No.: 17/638,428

(22) PCT Filed: Aug. 28, 2020

(86) PCT No.: PCT/US2020/048594
§ 371 (c)(1),
(2) Date: Feb. 25, 2022

(87) PCT Pub. No.: WO2021/041953
PCT Pub. Date: Mar. 4, 2021

(65) Prior Publication Data

US 2022/0307013 A1 Sep. 29, 2022

Related U.S. Application Data

(60) Provisional application No. 63/030,898, filed on May 27, 2020, provisional application No. 62/980,649, filed on Feb. 24, 2020, provisional application No. 62/894,664, filed on Aug. 30, 2019.

(51) Int. Cl.

| | |
|---|---|
| ***C07K 14/82*** | (2006.01) |
| ***A61P 35/00*** | (2006.01) |
| ***C07K 14/47*** | (2006.01) |
| ***C07K 14/71*** | (2006.01) |
| ***C07K 19/00*** | (2006.01) |
| ***C12N 15/10*** | (2006.01) |
| ***C12N 15/79*** | (2006.01) |
| *A61K 38/00* | (2006.01) |

(52) U.S. Cl.
CPC ...... *C12N 15/1079* (2013.01); *C07K 14/4703* (2013.01); *C07K 14/71* (2013.01); *C07K 14/82* (2013.01); *A61K 38/00* (2013.01)

(58) Field of Classification Search
CPC ............ C12N 15/1079; C12N 15/1072; C07K 14/4703; C07K 14/71; C07K 14/82; C07K 2319/50; A61K 38/00; A61K 38/1709; A61P 35/00
See application file for complete search history.

(56) References Cited

U.S. PATENT DOCUMENTS

| | | | | |
|---|---|---|---|---|
| 5,736,337 | A * | 4/1998 | Avruch | A61P 3/08 435/7.1 |
| 2003/0170751 | A1 | 9/2003 | Sherman et al. | |
| 2010/0144636 | A1 | 6/2010 | Pincus et al. | |
| 2015/0299278 | A1 | 10/2015 | Orrichio et al. | |
| 2016/0122415 | A1 | 5/2016 | Soucek et al. | |
| 2017/0067122 | A1* | 3/2017 | Langland | A61P 35/00 |

FOREIGN PATENT DOCUMENTS

| | | | |
|---|---|---|---|
| WO | 2017/173321 | A1 | 10/2017 |
| WO | 2018/227286 | A1 | 12/2018 |

OTHER PUBLICATIONS

Human RAF1 UniProtKB Accession No. P04049, accessed Mar. 20, 2025 at URL: uniprot.org/uniprot/P04049 (Year: 2025).*
De Rooij et al, "Minimal Ras-binding domain of Raf1 can be used as an activation-specific probe for Ras," Oncogene 14:623-625 (1997) (Year: 1997).*
Chuang et al, "Critical Binding and Regulatory Interactions between Ras and Raf Occur through a Small, Stable N-Terminal Domain of Raf and Specific Ras Effector Residues," (Mol Cell Biol 14:5318-5325 (1994)) (Year: 1994).*
Athuluri-Divakar et al, "A Small Molecule RAS-Mimetic Disrupts RAS Association with Effector Proteins to Block Signaling," Cell 165(3): 643-655 (2016) (Year: 2016).*
Chu et al., "Towards understanding cell penetration by stapled peptides", Med. Chem. Comm., Oct. 7, 2015, 6, 111-119.
Young, Lee, International Search Report and Written Opinion, PCT/US2020/048594, International Searching Authority, United States Patent and Trademark office, Feb. 5, 2021.
Bidwell et al., "Therapeutic peptides for cancer therapy. Part I—Peptide inhibitors of signal transduction cascades", Expert Opinion on Drug Delivery, Jul. 29, 2009, vol. 6, No. 10, pp. 1033-1047.
Steinheimer, K., Invitation Pursuant to Rule 62a(1) EPC and Rule 63(1) EPC, European Patent Office, Application No. 20857783.3, Aug. 24, 2023.

(Continued)

*Primary Examiner* — Julie Ha
*Assistant Examiner* — Kristina M Hellman
(74) *Attorney, Agent, or Firm* — Gavrilovich, Dodd & Lindsey LLP

(57) ABSTRACT

Screening methodologies using gene fragment overexpression that provide for the identification of peptide sequences which can modulate the functional regions of proteins of interests, and uses thereof are described. Peptides, polypeptides and polynucleotides identified by the methods of the disclosure, compositions containing such peptides, polypeptides and polynucleotides and uses thereof are also described.

7 Claims, 31 Drawing Sheets

Specification includes a Sequence Listing.

(56) References Cited

OTHER PUBLICATIONS

Lee, Sun Hwa, International Preliminary Report on Patentability and Written Opinion, PCT/US2020/048594, International Bureau of WIPO, Mar. 10, 2022.

Steinheimer, K., Extended European Search Report, European Patent Office, Application No. 20857783.3, Jan. 11, 2024.

* cited by examiner

| **Control** | **Apoptosis** | **Cell cycle** | **Chromatin Histone Modifiers** | **Genome Integrity** | **MAPK Signaling** | **Metabolism** | **NOTCH Signaling** | **Other Signaling** |
|---|---|---|---|---|---|---|---|---|
| HPRT1<br>GFP | CASP8 | CCND1<br>CDKN2A<br>RB1 | NCOA3 | CHEK2<br>MDM2<br>MDM4<br>TERT<br>TP53 | ARA<br>BRAF<br>HRAS<br>KRAS<br>MAP2K1<br>NRAS<br>RAB25<br>RAF1<br>RRAS2 | IDH1<br>IDH2 | NOTCH1 | AR<br>CDH1<br>GNA11<br>GNAQ<br>KEAP1<br>PTPN11<br>RAC1<br>RHOA |
| **PI3K Signaling** | **Protein Homeostasis** | **RNA Abundance** | **RTK Signaling** | **Splicing** | **TGFB Signaling** | **TOR Signaling** | **Transcription Factor** | **Wnt/B-Catenin Signaling** |
| AKT1<br>PIK3CA<br>PIK3R1<br>PPP2R1A | FBXW7<br>SKP2<br>VHL | DDX3X<br>DICER1 | EGRF<br>ERBB2<br>ERBB3<br>ERBB4<br>FGFR2<br>FGFR3<br>FLT3<br>KIT<br>MET<br>RASA1 | SF381 | SMAD2<br>SMAD4<br>TGFBR2 | MTOR<br>RHEB | MAX<br>MYC<br>MYCL<br>MYCN<br>NFE2L2<br>NKX2-98<br>RUNX1<br>YAP1 | CTNNB1 |

FIG. 6A

| Genes | # of Mutants | Genes | # of Mutants | Genes | # of Mutants |
|---|---|---|---|---|---|
| HPRT1 | NA | NOTCH1 | 3 | EGFR | 19 |
| GFP | NA | Other Signaling | | ERBB2 | 3 |
| Apoptosis | | CDH1 | 4 | ERBB3 | 3 |
| CASP8 | 3 | GNA11 | 4 | ERBB4 | 3 |
| Cell Cycle | | GNAQ | 4 | FGFR2 | 3 |
| CDKN2A | 3 | KEAP1 | 9 | FGFR3 | 2 |
| RB1 | 1 | PTPN11 | 15 | FLT3 | 2 |
| Chromatin Histone Modifiers | | RAC1 | 8 | KIT | 9 |
| EP300 | 8 | RHOA | 16 | MET | 4 |
| KMT2C | 2 | PI3K Signaling | | RASA1 | 1 |
| SETD2 | 5 | AKT1 | 3 | Splicing | |
| Genome Integrity | | PIK3CA | 12 | SF3B1 | 16 |
| CHEK2 | 6 | PIK3R1 | 11 | TGFB Signaling | |
| TP53 | 195 | PPP2R1A | 13 | SMAD2 | 2 |
| MAPK Signaling | | Protein Homeostasis | | SMAD4 | 31 |
| BRAF | 16 | FBXW7 | 13 | TGFBR2 | 3 |
| HRAS | 11 | VHL | 24 | TOR Signaling | |
| KRAS | 16 | SPOP | 2 | MTOR | 9 |
| MAP2K1 | 4 | RNA Abundance | | RHEB | 1 |
| NRAS | 9 | DDX3X | 3 | Transcription Factor | |
| RRAS2 | 2 | DICER1 | 9 | NFE2L2 | 9 |
| Metabolism | | ZFP36L2 | 1 | RUNX1 | 2 |
| IDH1 | 2 | | | Wnt/B-Catenin Signaling | |
| IDH2 | 5 | | | CTNNB1 | 15 |

*FIG. 6E*

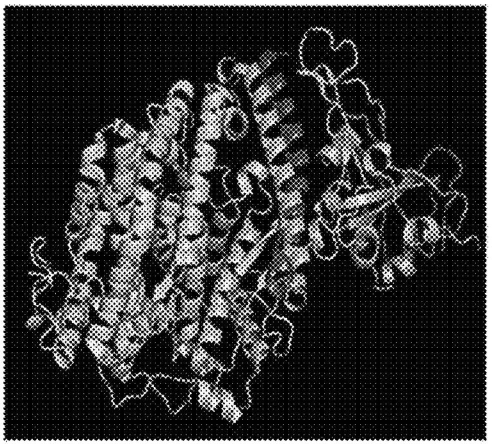

SARS-CoV-2 – ACE2 binding interface

ACE2 – RBD
Green: ACE2
Cyan: SARS-CoV2 RBD
Red: Candidate peptide 1
Orange: Candidate peptide 2

| | |
|---|---|
| ACE2: | MSSSSWLLL------SL------VTAAQSTIEEQAKTFLDK----------------FNHEAEDLFYQSS--------------LASWNYNTNI |
| ACE1 (iso1): | VLGWPEY------QWHFPLPDNYPEGIDLVTDEAEASKFVEE----------------YDRTSQVVWNEYA--------------EANWNYNTNI |
| ACE1 (iso2): | TTSSQTT------THQATAHQTSAQSPNLVTDEAEASKFVEE----------------YDRTSQVVWNEYA--------------EANWNYNTNI |
| DPP9: | VTVWMAYDTGYTERYMDVPENNQH-GYEAGSVALHVEKLPNE----------------PNRL-LILHGFL--------------DENVHFFHTN |
| DPP8: | VTLWIFYDTGYTERYMGHPDQNEQ-GYYLGSVAMQAEKFPSE----------------PNRL-LLLHGFL--------------DENVHFAHTS |
| ANPEP: | -NVTGYYRVNYDEENWRKIQTQLQRDHS-AIPVINRAQIIN------------------------------------DAFNLASAH |
| FAP: | VSSWEYYASVYTERFMGLPTKDDNLEHYKNSTVMARAEYFR----------------NVDY-LLIHGTA--------------DDNVHFQNSA |
| DPP4: | VSRWEYYDSVYTERYMGLPTPEDNLDHYRNSTVMSRAENFK----------------QVEY-LLIHGTA--------------DDNVHFQQSA |
| Fibronectin: | GSSIPPYNTEVTETTIVITWTPAPRIGFKLGVRPSQGGEAPREVTSDSGSIVVSGLTPGVEYVYTIQVLRDGQERDAPIVNKVVTPLSPPTNLHLEANP |

| | |
|---|---|
| ACE2: | TEENVQNMNNAGD--------------------KW---SAFLKEQSTLAQ----MY-PLQEIQNLTVKLQLQALQQNGSSVLSEDK |
| ACE1: | TTETSKILLQKNM--------------------QI---ANHTLKYGTQAR----KF--DVNQLQNTTIKRIIKKVQDLERAALPAQE |
| DPP9: | F-LVSQLIRAGKPYQLQIYPNERHSIRCP-----ESGEHYEVTLLHFLQEYL------------------------------ |
| DPP8: | I-LLSFLVRAGKPYDLQIYPQERHSIRVP-----ESGEHYELHLLHYLQENLGSRIAAL-----KVI------------------ |
| ANPEP: | KVPVTLALINNTLFLIEERQYMPWEAALSSLSYFKLMFDRSEVYGPMKNYLKKQVTPL--F-------IHFRN---------NTNNWREIPEN- |
| FAP: | Q-IAKALVNAQVDFQAMWYSDQNHGLSGL------STNHLYTHMTHFLKQCFSLSD------------------------------ |
| DPP4: | Q-ISKALVDVGVDFQAMWYTDEDHGIASS------TAHQHIYTHMSHFIKQCFSLP------------------------------ |
| Fibronectin: | QSSCTFDNLSPGLEYNVSVYTVKDDKESVP------------ISD------------TIIPA--------------------- |

*FIG. 8C*

GENE FRAGMENT OVEREXPRESSION SCREENING METHODOLOGIES, AND USES THEREOF

CROSS REFERENCE TO RELATED APPLICATIONS

This application is a U.S. National Stage Application filed under 35 U.S.C. § 371 and claims priority to International Application No. PCT/US2020/048594, filed Aug. 28, 2020, which application claims priority of under 35 U.S.C. § 119 from Provisional Application Ser. No. 62/894,664, filed Aug. 30, 2019; Provisional Application Ser. No. 62/980,649, filed Feb. 24, 2020; and Provisional Application Ser. No. 63/030,898, filed May 27, 2020; the disclosures of each of which are incorporated herein by reference in their entirety.

STATEMENT REGARDING FEDERALLY SPONSORED RESEARCH

This invention was made with government support under CA222826, GM123313, and HG009285 awarded by the National Institutes of Health and under DGE1650112 awarded by the National Science Foundation. The government has certain rights in the invention.

TECHNICAL FIELD

The disclosure provides for screening methodologies using gene fragment overexpression that provide for the identification of peptide sequences which can modulate the functional regions of proteins of interests, and uses thereof. The disclosure further provides peptides and methods use for inhibiting oncoproteins and infectious agents.

INCORPORATION BY REFERENCE OF SEQUENCE LISTING

Accompanying this filing is a Sequence Listing entitled, "Sequence-listing ST25" created on Jun. 24, 2025 and having 6,309,988 bytes of data, machine formatted on IBM-PC, MS-Windows operating system. The sequence listing is hereby incorporated by reference in its entirety for all purposes.

BACKGROUND

Genetic screening has rapidly become a ubiquitous tool to probe protein function and accelerate drug discovery. Libraries of genetically encoded perturbations (CRISPR-Cas9 sgRNA, siRNA, etc.) enable high throughput identification of proteins essential to cancer cells fitness and infectious organisms. However, existing screens typically fail to capture how proteins function biologically and provide little information on how to target hits therapeutically. Transposon mediated fragmentation and overexpression of cDNA has been used to identify peptide inhibitors of essential proteins in *Saccharomyces cerevisiae*. However, these libraries randomly generate gene fragments of various lengths hindering control of library composition, feature many out of frame fragments, and are limited in their translational relevance due to the choice of model organism.

SUMMARY

Disclosed herein are pharmaceutical compositions in unit dose form comprising: (a) a peptide or salt thereof; and (b)

at least one of a pharmaceutically acceptable: excipient, diluent, or carrier. In some embodiments, a peptide or salt thereof can have at least about 80% sequence identity to a polypeptide of any one of SEQ ID NO: 1-9489. In some embodiments, a peptide or salt thereof (i) can modulate an expression level of a target protein implicated in a disease or condition, as measured by an at least partial increase or an at least partial decrease of a level of the target protein in an in vitro assay in a cell treated with the peptide or salt thereof as determined by a Western blot relative to a level of the target protein in an otherwise comparable cell not treated with the peptide or salt thereof; (ii) can produce an at least partial increase or an at least partial decrease of an activity of the target protein, as measured by a level of the activity of the target protein in a cell treated with the peptide or salt thereof relative to a level of activity of the target protein in an otherwise comparable cell not treated with the peptide or salt thereof as determined by an in vitro assay; (iii) can produce an at least partial increase or an at least partial decrease of an activity of a protein downstream of the target protein in a cellular pathway in a cell treated with the peptide or salt thereof relative to a level of activity of the protein downstream of the target protein in a cellular pathway in an otherwise comparable cell not treated with the peptide or salt thereof as determined by an in vitro assay; (iv) can kill a cancer cell in an in vitro assay; or (v) any combination of (i-iv). In some embodiments, a peptide or salt thereof can comprise at least about an 80% sequence identity to a polypeptide of SEQ ID NO:9530. In some embodiments, a peptide or salt thereof can comprise at least about an 80% sequence identity to a polypeptide of SEQ ID NO:9522.

In some embodiments, a peptide or salt thereof can comprise at least about an 80% sequence identity to a polypeptide of SEQ ID NO:9521 or SEQ ID NO:9526. In some embodiments, a peptide or salt thereof can comprise at least about an 80% sequence identity to the polypeptide of SEQ ID NO:9531 or SEQ ID NO:9701. In some embodiments, a peptide or salt thereof can modulate an expression level of a target protein implicated in a disease or condition, as measured by an at least partial increase or the at least partial decrease of a level of the target protein in the in vitro assay in a cell treated with the peptide or salt thereof as determined by the Western blot relative to a level of the target protein in the otherwise comparable cell not treated with the peptide or salt thereof. In some embodiments, a target protein can be at least partially encoded by a gene in Table 7, a variant of a gene in Table 7, or a fragment of any of these. In some embodiments, a peptide or salt thereof can produce an at least partial increase or an at least partial decrease of an activity of a target protein, as measured by a level of the activity of the target protein in the cell treated with the peptide or salt thereof relative to a level of activity of the target protein in the otherwise comparable cell not treated with the peptide or salt thereof as determined by the in vitro assay. In some embodiments, a target protein can be at least partially encoded by a gene in Table 7, a variant of a gene in Table 7, or a fragment of any of these. In some embodiments, a target protein can be a kinase or a biologically active fragment thereof. In some embodiments, a target protein can be a phosphatase or a biologically active fragment thereof. In some embodiments, a peptide or salt thereof can produce an at least partial increase or an at least partial decrease of an activity of a protein downstream of a target protein in a cellular pathway in the cell treated with the peptide or salt thereof relative to a level of activity of the protein downstream of the target protein in the cellular pathway in an otherwise comparable cell not treated with the peptide or salt thereof as determined by an in vitro assay. In some embodiments, a target protein can be at least partially encoded by a gene in Table 7, a variant of a gene in Table 7, or a fragment of any of these. In some embodiments, a target protein can comprise a protein at least partially encoded by a gene in Table 7, a variant of a gene in Table 7, or a fragment of any of these. In some embodiments, a peptide of salt thereof can kill a cancer cell in an in vitro assay. In some embodiments, a peptide or salt thereof can modulate a target protein by at least partially inhibiting a protein to protein interaction. In some embodiments, a protein to protein interaction can comprise a ligand to receptor interaction. In some embodiments, a protein to protein interaction can comprise a regulatory protein complex. In some embodiments, a peptide or salt thereof can at least partially reduce a protein to nucleic acid interaction. In some embodiments, a peptide can comprise independently Gly, or an amino acid comprising a $C_1$-$C_{10}$ alkyl, a $C_1$-$C_{10}$ alkenyl, a $C_1$-$C_{10}$ alkynyl, a cycloalkyl, or an alkylcycloalkyl side chain. In some embodiments, a peptide can comprise an amino acid comprising an aromatic side chain. In some embodiments, a peptide can comprise an amino acid comprising a side chain that can be at least partially protonated at a pH of about 7.3. In some embodiments, a peptide can comprise an amino acid comprising an amide containing side chain. In some embodiments, a peptide can comprise an amino acid comprising an alcohol or thiol containing side chain. In some embodiments, a peptide can comprise an amino acid comprising a side chain that can be at least partially deprotonated at a pH of about 7.3. In some embodiments, a peptide or salt thereof can comprise a recombinant peptide. In some embodiments, at least one amino acid of the peptide or salt thereof can comprise a chemical modification. In some embodiments, a chemical modification can comprise acetylation, sulfonation, amidation, or esterification. In some embodiments, a peptide or salt thereof can comprise a stapled peptide or salt thereof, a stitched peptide or salt thereof, a macrocyclic peptide or salt thereof, or any combination thereof. In some embodiments, peptide or salt thereof can comprise a stapled peptide and the stapled peptide can comprise a covalent linkage between two amino acid side-chains. In some embodiments, a peptide or salt thereof can further comprise a cell penetrating peptide directly or indirectly linked to a peptide or salt thereof. In some embodiments, an amino acid of the peptide or salt thereof positioned at an end terminus can comprise a side chain that can be at least partially deprotonated at a pH of about 7.3.

Also disclosed herein are nucleic acids. In some embodiments, a nucleic acid can at least partially encode a peptide, having at least about 80% sequence identity to a polypeptide of SEQ ID NO:1-9489 or 9701. In some embodiments, the peptide; (i) can modulate an expression level of a target protein implicated in a disease or condition, as measured by an at least partial increase or an at least partial decrease of a level of the target protein in an in vitro assay in a cell treated with the nucleic acid as determined by a Western blot relative to a level of the target protein in an otherwise comparable cell not treated with the nucleic acid; (ii) can produce an at least partial increase or an at least partial decrease of an activity of the target protein, as measured by a level of the activity of the target protein in a cell treated with the nucleic acid relative to a level of activity of the target protein in an otherwise comparable cell not treated with the nucleic acid in as determined by an in vitro assay; (iii) can produce an at least partial increase or an at least partial decrease of an activity of a protein downstream of the target protein in a cellular pathway in a cell treated with the nucleic acid relative to a level of activity of the protein downstream of the target protein in a cellular pathway in an otherwise comparable cell not treated with the nucleic acid as determined by an in vitro assay; (iv) can kill a cancer cell in an in vitro assay; or (v) any combination of (i-iv). In some embodiments, a peptide at least partially encoded by the nucleic acid may not comprise more than about 40 amino acids. In some embodiments, a nucleic acid can be comprised in a pharmaceutical composition in unit dose form. In some embodiments, a peptide at least partially encoded by the nucleic acid can comprise independently Gly, or an amino acid comprising a $C_1$-$C_{10}$ alkyl, a $C_1$-$C_{10}$ alkenyl, a C1-C10 alkynyl, a cycloalkyl, or an alkylcycloalkyl side chain. In some embodiments, a peptide at least partially encoded by a nucleic acid can comprise an amino acid comprising an aromatic side chain. In some embodiments, a peptide at least partially encoded by a nucleic acid can comprise an amino acid comprising a side chain that can be at least partially protonated at a pH of about 7.3. In some embodiments, a peptide at least partially encoded by a nucleic acid can comprise an amino acid comprising an amide containing side chain. In some embodiments, a peptide at least partially encoded by a nucleic acid can comprise an amino acid comprising an alcohol or thiol containing side chain. In some embodiments, a peptide at least partially encoded by a nucleic acid can comprise an amino acid comprising a side chain that can be at least partially deprotonated at a pH of about 7.3. In some embodiments, a nucleic acid can be double stranded. In some embodiments, a nucleic acid can comprise DNA, RNA or any combination thereof.

Also disclosed herein are vectors that comprise a nucleic acid of the disclosure. In some embodiments, a vector can comprise a polypeptide coat. In some embodiments, a vector can comprise a nanoparticle, a microparticle, a viral vector, a virus-like particle, a liposome, or any combination thereof. In some embodiments, a vector can comprise a viral vector, and the viral vector can comprise an AAV vector. In some embodiments, an AAV vector can be selected from the group consisting of: AAV1, AAV2, AAV3, AAV4, AAV5, AAV6, AAV7, AAV8, AAV9, AAV10, AAV11, AAV12, AAVDJ, and variants thereof. In some embodiments, the vector can be a gamma-retroviral vector.

Also disclosed herein are isolated peptides or salt thereof comprising a sequence having at least about 80% sequence homology to any one of the peptides of SEQ ID NO: 1-9489 or 9701.

Also disclosed herein is a kit that comprises a pharmaceutical composition, a nucleic acid, a vector, an isolated peptide or salt thereof; and a container.

Provided herein is a method of at least partially treating or preventing a disease or condition in a subject. In some cases, the method comprises administering a therapeutically effective amount of a pharmaceutical composition, a nucleic acid, a vector, or an isolated peptide or salt thereof; to a subject to at least partially prevent or treat the disease or condition. In some cases, a method comprises at least partially treating a subject. In some cases, at least partially treating comprises ameliorating at least one symptom of a disease or condition. In some cases, a method comprises at least partially treating. In some cases, at least partially treating comprises reducing a growth of a tumor. In some cases, a method comprises at least partially treating. In some cases, at least partially treating comprises at least partially eliminating a tumor. In some cases, a disease or condition comprises a cancer. In some cases, a cancer comprises a sarcoma, a carcinoma, a melanoma, a lymphoma, a leukemia, a blastoma, a germ cell tumor, a myeloma, or any combination thereof. In some cases, prior to treating a subject, the subject has been diagnosed with cancer.

In some cases, a method provided herein can further comprise diagnosing a subject with cancer. In some cases, diagnosing comprises diagnosing with a physical examination, a biopsy, a radiological image, a blood test, a urine test, an antibody test, or any combination thereof. In some cases, diagnosing comprises radiological imagine. In some cases, radiological imaging comprises a computed tomography (CT) image, a nuclear scan, an X-Ray image, a magnetic resonance image (MRI), an ultrasound image, or any combination thereof. In some cases, administering can be intra-arterial, intravenous, intramuscular, oral, topical, intranasal, subcutaneous, inhalation, catheterization, gastrostomy tube administration, intraosseous, ocular, otic, transdermal, rectal, nasal, intravaginal, intracavernous, transurethral, sublingual, or any combination thereof. In some cases, administering can be performed at least about: 1 time per day, 2 times per day, 3 times per day, or 4 times per day. In some cases, administering can be performed for about: 1 day to about 7 days, 1 week to about 5 weeks, 1 month to about 12 months, 1 year to about 3 years, 3 years to about 8 years, or 8 years to about 20 years. In some cases, a method further comprises administering a therapeutically effective amount of a second therapy to a subject. In some cases, a second therapy comprises surgery, chemotherapy, radiation therapy, immunotherapy, hormone therapy, a checkpoint inhibitor, targeted drug therapy, a gene editing therapy, an RNA editing therapy, a protein knockdown therapy, chimeric antigen receptor (CAR) T-cell therapy, or a combination thereof.

In some cases, a subject is a human. In some cases, a human is from about 1 day to about 1 month old, from about 1 month to about 12 months old, from about 1 year to about 7 years old, from about 5 years to about 25 years old, from about 20 years to about 50 years old, from about 45 years to about 80 years old, or from about 75 years to about 130 years old.

Provided herein is a method of making a pharmaceutical composition. In some cases, a method comprises contacting a peptide or salt thereof with a pharmaceutically acceptable excipient, diluent or carrier.

Provided herein is a method of at least partially reducing or at least partially increasing activity of a target protein comprising: (a) expressing a fragment of a gene in a target cell, wherein the gene fragment is expressed from a polynucleotide, wherein the gene fragment comprises at least a portion of the target protein and wherein the gene fragment is from about 60 nucleotides to about 150 nucleotides in length; and (b) measuring the at least partial reduction or the at least partial increase of activity by determining a change of a level of activity of the target protein in a cell treated with the polynucleotide relative to a level of activity of the target protein in an otherwise comparable cell not treated with the polynucleotide an in vitro assay; wherein the target protein is selected from a protein at least partially encoded by a gene or a variant thereof recited in Table 7.

Provided herein is a method of at least partially reducing or at least partially increasing activity of a protein downstream of a target protein in a cellular pathway comprising: (a) expressing a fragment of a gene in a target cell, wherein the gene fragment is expressed from a polynucleotide, wherein the gene fragment comprises at least a portion of the target protein and wherein the gene fragment is from about 60 nucleotides to about 150 nucleotides in length; and (b) measuring the at least partial reduction or the at least partial increase of activity by determining a change of a level of activity of the downstream protein of a cell treated with the polynucleotide relative to a level of activity of the downstream protein in an otherwise comparable cell not treated with the polynucleotide in an in vitro assay; wherein the target protein is selected from a protein at least partially encoded by a gene or a variant thereof recited in Table 7. In some cases, a fragment of a gene encodes for a peptide comprising a sequence having at least about 80% sequence homology to any one of the peptides of SEQ ID NO: 1-9489 or 9701. In some cases, a polynucleotide is comprised in a plasmid. In some cases, a polynucleotide or a plasmid can be transfected into a target cell. In some cases, at least a portion of a target protein comprises about 20 amino acids to about 50 amino acids. In some cases, a reduction of activity further comprises reduced cell growth.

Provided herein is a method of screening for at least partially reducing or at least partially increasing activity of a target protein, a protein downstream of a target protein in a cellular pathway, or both comprising: (a) expressing one or more fragments of a gene in a target cell, wherein each gene fragment is expressed from a polynucleotide, wherein the one or more gene fragments comprise at least a portion of the target protein and wherein the gene fragment is from about 60 nucleotides to about 300 nucleotides in length; and (b) measuring the at least partial reduction or the at least partial increase of activity by determining a change of a level of activity of the target protein in a cell treated with the polynucleotide relative to a level of activity of the target protein in an otherwise comparable cell not treated with the polynucleotide in an in vitro assay; wherein the target protein is selected from a protein encoded by a gene or a variant thereof recited in Table 7. In some cases, a fragment of a gene encodes for a peptide comprising a sequence having at least about 80% sequence homology to any one of peptides of SEQ ID Nos: 1-9489. In some cases, a polynucleotide is comprised in a plasmid. In some cases, a polynucleotide or a plasmid is transfected into a target cell. In some cases, at least a portion of a target protein comprises about 20 amino acids to about 50 amino acids.

The disclosure also provides a composition comprising a peptide fragment, wherein the peptide fragment consists of 35-45 amino acids from a protein selected from the group consisting of AKT1, AR, ARAF, BRAF, CASP8, CCND1, CDH1, CDKN2A, CHEK2, CTNNB1, DDX3X, DICER1, EGFR, EP300, ERBB2, ERBB3, ERBB4, FBXW7, FGFR2, FGFR3, FLT3, GFP, GNA11, GNAQ, HPRT1, HRAS, IDH1, IDH2, KEAP1, KIT, KMT2C, KRAS, KRAS4B, MAP2K1, MAX, MDM2, MDM4, MET, MTOR, MYC, MYCL, MYCN, NCOA3, NFE2L2, NKX2, NOTCH1, NRAS, OMOMYC, PIK3CA, PIK3R1, PPP2R1A, PTPN11, RAB25, RAC1, RAF1, RASA1, RB1, RHEB, RHOA, RRAS2, RUNX1, SETD2, SF3B1, SKP2, SMAD2, SMAD4, SPOP, TERT, TGFBR2, TP53, VHL, YAP1, ZFP36L2, ACE1, ACE2, DPP4, DPP8, DPP9, ANPEP, FAP, and Fibronectin, wherein the peptide fragment at least partially inhibits the biological activity of the protein from which it has greater than 98% identity and/or binds to a cognate of the protein. In one embodiment, the peptide fragment is identified by: synthesizing a library of overlapping gene fragments from a gene that expresses the protein, wherein each gene fragment of the library of overlapping gene fragments has a unique nucleotide sequence, wherein each gene fragment has a sequence which partial overlaps with the sequences of least two or more gene fragments having nucleotide sequences from the gene; pooling and cloning the gene fragments into vectors, wherein each vector overexpresses one gene fragment when transduced or transfected into a cell; transfecting or transducing cells with the vectors comprising gene fragments, wherein each transduced or transfected cell has only one vector that comprises a gene fragment; screening the transfected or transduced cells for cell growth over various time points; sequencing and quantifying gene fragment abundance from each of the time points; and mapping the sequenced gene fragments back to the gene that express the target protein and providing a depletion score for each codon, wherein the depletion score is defined as the mean depletion/enrichment of all overlapping sequenced gene fragments, and wherein codons of the gene fragments which have a depletion score below a p=0.05 significance threshold, indicates peptide sequences which inhibit functional regions of the protein expressed by the gene. In another embodiment, the peptide fragment consists essentially of or consists of a sequence of 35-45 amino acids selected from the group consisting of: (a) a sequence of 35-40 amino acids located between amino acid 6 and 466 of SEQ ID NO:9540 and optionally wherein the peptide has a mutation as referenced to SEQ ID NO:9540 of 17K or 52R; (b) a sequence of 35-40 amino acids of SEQ ID NO:9542; (c) a sequence of 35-40 amino acids of SEQ ID NO:9544; (d) a sequence of 35-40 amino acids of SEQ ID NO:9546 and optionally wherein the peptide has a mutation as referenced to SEQ ID NO:9546 of 464V, 466E, 467L, 468C, 469A/R, 568D, 575K, 581I, 594G/N, 596D/S, 597Q/V, and/or 600E; (e) a sequence of 35-40 amino acids of SEQ ID NO:9548 and optionally wherein the peptide has a mutation as referenced to SEQ ID NO:9548 of 363D, and/or 367G; (f) a sequence of 35-40 amino acids of SEQ ID NO:9550; (g) a sequence of 35-40 amino acids of SEQ ID NO:9552 and optionally wherein the peptide has a mutation as referenced to SEQ ID NO:9552 of 222G, 257G/N, and/or 290G; (h) a sequence of 35-40 amino acids of SEQ ID NO:9554 and optionally wherein the peptide has a mutation as referenced to SEQ ID NO:9554 of 118T and/or 84Y; (i) a sequence of 35-40 amino acids of SEQ ID NO:9556 and optionally wherein the peptide has a mutation as referenced to SEQ ID NO:9556 of 381R, 388L/Y, 389H, 415F, and/or 452G; (j) a sequence of 35-40 amino acids of SEQ ID NO:9558 and optionally wherein the peptide has a mutation as referenced to SEQ ID NO:9558 of 32V, 34R, 333F, 334K, 335T, 383C/G, 386G, 387I/K/Y, and/or 426D; (k) a sequence of 35-40 amino acids of SEQ ID NO:9560 and optionally wherein the peptide has a mutation as referenced to SEQ ID NO:9560 of 528C and/or 532A/M; (l) a sequence of 35-40 amino acids of SEQ ID NO:9562 and optionally wherein the peptide has a mutation as referenced to SEQ ID NO:9562 of 1703S, 1705K, 1709N, 1806N, 1809R, 1810Y/V, and/or 1813D/G; (m) a sequence of 35-40 amino acids of SEQ ID NO:9564 and optionally wherein the peptide has a mutation as referenced to SEQ ID NO:9564 of 85M, 108G/K, 252C, 270C, 289T/V, 596R/S, 598V, 628F, 719C/D, 724S, 759N, 836H, 858R, 861Q, and/or 891C; (n) a sequence of 35-40 amino acids of SEQ ID NO:9566 and optionally wherein the peptide has a mutation as referenced to SEQ ID NO:9566 of 1397D, 1398P, 1399N, 1400I, 1414C/D, 1446C, and/or 1451P; (o) a sequence of 35-40 amino acids of SEQ ID NO:9568 and optionally wherein the peptide has a mutation as referenced to SEQ ID NO:9568 of 310F and/or 755M/S; (p) a sequence of 35-40 amino acids of SEQ ID NO:9570 and optionally wherein the peptide has a mutation as referenced to SEQ ID NO:9570 of 103H and/or 232V; (q) a sequence of 35-40 amino acids of SEQ ID NO:9572 and optionally wherein the peptide has a mutation as referenced to SEQ ID NO:9572 of 785R/V; (r) a sequence of 35-40 amino acids of SEQ ID NO:9574 and optionally wherein the peptide has a mutation as referenced to SEQ ID NO:9574 of 426L, 465C/H, 479Q, 502V, 505G/L, 516N/R, 517E/R, 520N, and/or 545C; (s) a sequence of 35-40 amino acids of SEQ ID NO:9576 and optionally wherein the peptide has a mutation as referenced to SEQ ID NO:9576 of 251Q and/or 545Q; (t) a sequence of 35-40 amino acids of SEQ ID NO:9578 and optionally wherein the peptide has a mutation as referenced to SEQ ID NO:9578 of 248C and/or 249C; (u) a sequence of 35-40 amino acids of SEQ ID NO:9580 and optionally wherein the peptide has a mutation as referenced to SEQ ID NO:9580 of 617E and/or 618L; (v) a sequence of 35-40 amino acids of SEQ ID NO:9582; (w) a sequence of 35-40 amino acids of SEQ ID NO:9584 and optionally wherein the peptide has a mutation as referenced to SEQ ID NO:9584 of 183C and/or 209H; (x) a sequence of 35-40 amino acids of SEQ ID NO:9586 and optionally wherein the peptide has a mutation as referenced to SEQ ID NO:9586 of 48V, 209P, and/or 247G; (y) a sequence of 35-40 amino acids of SEQ ID NO:9588; (z) a sequence of 35-40 amino acids of SEQ ID NO:9590 and optionally wherein the peptide has a mutation as referenced to SEQ ID NO:9590 of 12V, 13R/V, 59T, 60S/V, 61K/L, and/or 117N/R; (aa) a sequence of 35-40 amino acids of SEQ ID NO:9592 and optionally wherein the peptide has a mutation as referenced to SEQ ID NO:9592 of 132C/H; (bb) a sequence of 35-40 amino acids of SEQ ID NO:9594 and optionally wherein the peptide has a mutation as referenced to SEQ ID NO:9594 of 137E, 140Q, and/or 172G/K/S; (cc) a sequence of 35-40 amino acids of SEQ ID NO:9596 and optionally wherein the peptide has a mutation as referenced to SEQ ID NO:9596 of 152A, 333D/S, 413H, 477S, 483C, 524C, 525C, and/or 571D; (dd) a sequence of 35-40 amino acids of SEQ ID NO:9598 and optionally wherein the peptide has a mutation as referenced to SEQ ID NO:9598 of 559G, 573Q, 576P, 636V, 637H, 642E, 812V, and/or 816V/Y; (ee) a sequence of 35-40 amino acids of SEQ ID NO:9600 and optionally wherein the peptide has a mutation as referenced to SEQ ID NO:9600 of 370Y and/or 385Y; (ff) a sequence of 35-40 amino acids of SEQ ID NO:9602 and optionally wherein the peptide has a mutation as referenced to SEQ ID NO:9602 of 12R/V, 14I, 19F, 20R, 21R, 34L, 59G/T, 61K/R, 62K, 63K, and/or 117N; (gg) a sequence of 35-40 amino acids of SEQ ID NO:9604; (hh) a sequence of 35-40 amino acids of SEQ ID NO:9606 and optionally wherein the peptide has a mutation as referenced to SEQ ID NO:9606 of 121R, 124L/S and/or 130C; (ii) a sequence of 35-40 amino acids of SEQ ID NO:9608; (jj) a sequence of 35-40 amino acids of SEQ ID NO:9610; (kk) a sequence of 35-40 amino acids of SEQ ID NO:9612; (ll) a sequence of 35-40 amino acids of SEQ ID NO:9614 and optionally wherein the peptide has a mutation as referenced to SEQ ID NO:9614 of 1110I, 1246H, and/or 1248C/H; (mm) a sequence of 35-40 amino acids of SEQ ID NO:9616 and optionally wherein the peptide has a mutation as referenced to SEQ ID NO:9616 of 1977R, 1981E, 2215F, 2230V, and/or 2406A/M; (nn) a sequence of 35-40 amino acids of SEQ ID NO:9618; (oo) a sequence of 35-40 amino acids of SEQ ID NO:9620; (pp) a sequence of 35-40 amino acids of SEQ ID NO:9622; (qq) a sequence of 35-40 amino acids of SEQ ID NO:9624; (rr) a sequence of 35-40 amino acids of SEQ ID NO:9626 and optionally wherein the peptide has a mutation as referenced to SEQ ID NO:9626 of 77G, 79G/Q, 80A/I, 81S/V, and/or 82D/V; (ss) a sequence of 35-40 amino acids of SEQ ID NO:9628; (tt) a sequence of 35-40 amino acids of SEQ ID NO:9630 and optionally wherein the peptide has a mutation as referenced to SEQ ID NO:9630 of 440R and/or 449Y; (uu) a sequence of 35-40 amino acids of SEQ ID NO:9632 and optionally wherein the peptide has a mutation as referenced to SEQ ID NO:9632 of 12D, 13D/R, 16N, 61H/K/R, and/or 62K; (vv) a sequence of 35-40 amino acids of SEQ ID NO:9634; (ww) a sequence of 35-40 amino acids of SEQ ID NO:9636 and optionally wherein the peptide has a mutation as referenced to SEQ ID NO:9636 of 344G/M, 345I/Y, 365V, 420R, 471L, 539R, 545A/K, 546R, and/or 956F; (xx) a sequence of 35-40 amino acids of SEQ ID NO:9638 and optionally wherein the peptide has a mutation as referenced to SEQ ID NO:9638 of 375W, 376R, 379E/N, 557P, 560G/Y, 565R, 567E, and/or 568T; (yy) a sequence of 35-40 amino acids of SEQ ID NO:9640 and optionally wherein the peptide has a mutation as referenced to SEQ ID NO:9640 of 144C, 179R, 182W, 183Q/W, 217K/R, 220M, 256Y, 257C, 258C/H and/or 260G; (zz) a sequence of 35-40 amino acids of SEQ ID NO:9642 and optionally wherein the peptide has a mutation as referenced to SEQ ID NO:9642 of 60V, 71L, 72D, 76A/K, 279C, 282M, 461G/T, 498W, 503V, 504I, 507K, and/or 510H/L; (aaa) a sequence of 35-40 amino acids of SEQ ID NO:9644; (bbb) a sequence of 35-40 amino acids of SEQ ID NO:9646 and optionally wherein the peptide has a mutation as referenced to SEQ ID NO:9646 of 15S, 18Y, 29L/S, 61R, 68H, 135N, 178V; (ccc) a sequence of 35-40 amino acids of SEQ ID NO:9648; (ddd) a sequence of 35-40 amino acids of SEQ ID NO:9650 and optionally wherein the peptide has a mutation as referenced to SEQ ID NO:9650 of 789L; (eee) a sequence of 35-40 amino acids of SEQ ID NO:9652 and optionally wherein the peptide has a mutation as referenced to SEQ ID NO:9652 of 563S; (fff) a sequence of 35-40 amino acids of SEQ ID NO:9654 and optionally wherein the peptide has a mutation as referenced to SEQ ID NO:9654 of 60V; (ggg) a sequence of 35-40 amino acids of SEQ ID NO:9656 and optionally wherein the peptide has a mutation as referenced to SEQ ID NO:9656 of 17A, 22R, 37I, 42C, 47K, 59G/Y, 60K, 61D, 62E/R, 63K, 70S, 73P, and/or 161T/V; (hhh) a sequence of 35-40 amino acids of SEQ ID NO:9658 and optionally wherein the peptide has a mutation as referenced to SEQ ID NO:9658 of 72H/L; (iii) a sequence of 35-40 amino acids of SEQ ID NO:9660 and optionally wherein the peptide has a mutation as referenced to SEQ ID NO:9660 of 107L and/or 110N; (jjj) a sequence of 35-40 amino acids of SEQ ID NO:9662 and optionally wherein the peptide has a mutation as referenced to SEQ ID NO:9662 of 1543Q, 1603R, 1625C/L, and/or 1628T; (kkk) a sequence of 35-40 amino acids of SEQ ID NO:9664 and optionally wherein the peptide has a mutation as referenced to SEQ ID NO:9664 of 622Q, 625C/H, 626Y, 662R, 663P, 666E/N/T, 700E, 741E, 746V, 862K, 902G/K, and/or 903P; (lll) a sequence of 35-40 amino acids of SEQ ID NO:9666; (mmm) a sequence of 35-40 amino acids of SEQ ID NO:9668 and optionally wherein the peptide has a mutation as referenced to SEQ ID NO:9668 of 450E/N; (nnn) a sequence of 35-40 amino acids of SEQ ID NO:9670 and optionally wherein the peptide has a mutation as referenced to SEQ ID NO:9670 of 339L, 351G/H, 352R/V, 353C/N, 355V/Y, 356L/S, 361C/H, 363S, 365D/R, 366K, 368C, 382D, 383R, 384D, 3865/V, 406V, 408L, 504R, 507N, 509G, 523W, and/or 524L/R; (ooo) a sequence of 35-40 amino acids of SEQ ID NO:9672 and optionally wherein the peptide has a mutation as referenced to SEQ ID NO:9672 of 87N and/or 131G; (ppp) a sequence of 35-40 amino acids of SEQ ID NO:9674; (qqq) a sequence of 35-40 amino acids of SEQ ID NO:9676 and optionally wherein the peptide has a mutation as referenced to SEQ ID NO:9676 of 553H; (rrr) a sequence of 35-40 amino acids of SEQ ID NO:9678 and optionally wherein the peptide has a mutation as referenced to SEQ ID NO:9678 of 105C/V, 109S/V, 110P, 111R, 113V, 120E, 121Y, 125M/P, 126D/S, 127P/Y, 130R/V, 131I, 132E/N, 134L, 135R, 136E/H, 137Q, 138T/V, 141R/Y, 143A/M, 144H/P, 145P, 147G, 151S/H, 152L/S, 155P, 156P, 157D, 158S, 159P, 161D/T, 162F/N, 163C/H, 164E, 171K, 172D/F, 173G/L, 176F/R, 177R/S, 178Q, 179D/Q/R, 180K, 181C/H, 190L, 192R, 193N/R, 194F/H, 195F/M/N, 196P, 197G/L, 205N/S, 208G, 211I, 213L, 214R, 215G/I, 216E/L, 218E, 220C/H, 230P, 232S, 234C/H, 236C/H, 237I/K/V, 238R/W/Y, 239D, 240R, 241F/P, 2425/Y, 243I, 244D/S, 245D/S, 246T/V, 247I, 248Q/W, 249G/M/S, 250R, 251F/N, 253A, 254S, 255T, 256I, 257R, 258D/G/K, 259V/Y, 262V, 265P, 266R/V, 267Q/W, 270S/V, 271K/V, 272G/M, 273C/H, 274G/L, 275G/Y, 276G/P, 277G/Y, 278R/S, 279E/R, 280K/S, 281E/H/V, 282Q/W, 283P, 284P, 285K/V, 286G/Q, 332F, 334V/W, 337H/S, and/or 348F/S; (sss) a sequence of 35-40 amino acids of SEQ ID NO:9680 and optionally wherein the peptide has a mutation as referenced to SEQ ID NO:9680 of 79G, 80R, 82P, 89H, 115N, 117C, 118P, 120G, 128H, 130D/F, 131Y, 136V, 151F/N, 153P, 158R/V, 161Q, 162R, 165D, 178P, 184P, and/or 188P; (ttt) a sequence of 35-40 amino acids of SEQ ID NO:9682; (uuu) a sequence of 35-40 amino acids of SEQ ID NO:9684 and optionally wherein the peptide has a mutation as referenced to SEQ ID NO:9684 of 159Y; (vvv) a sequence of 35-40 amino acids of SEQ ID NO:9688; (www) a sequence of 35-40 amino acids of SEQ ID NO:9686; (xxx) a sequence of 35-40 amino acids of SEQ ID NO:9696; (yyy) a sequence of 35-40 amino acids of SEQ ID NO:9700; (zzz) a sequence of 35-40 amino acids of SEQ ID NO:9690; (aaaa) a sequence of 35-40 amino acids of SEQ ID NO:9692; (bbbb) a sequence of 35-40 amino acids of SEQ ID NO:9694; and (cccc) a sequence of 35-40 amino acids of SEQ ID NO:9698. In another embodiment, the peptide of (a) has the sequence selected from the group consisting of SEQ ID NO:1-5, 5000-5009 and 5010. In another embodiment, the peptide of (b) has the sequence selected from the group consisting of SEQ ID NO: 3499, 3750-3759, 5011-5072 and 5073. In another embodiment, the peptide of (c) has the sequence selected from the group consisting of SEQ ID NO: 5074-5083 and 5084. In another embodiment, the peptide of (d) has the sequence selected from the group consisting of SEQ ID NO: 6-15, 350-489, 2555-2586, 2949-2974, 3500-3509, 3760-3792, 5086-5184 and 5185. In another embodiment, the peptide of (e) has the sequence selected from the group consisting of SEQ ID NO: 490-498, 2587-2588, 2975-2981, 3511, 3793-3804, 5186-5227 and 5228. In another embodiment, the peptide of (f) has the sequence selected from the group consisting of SEQ ID NO: 5229-5249 and 5250. In another embodiment, the peptide of (g) has the sequence selected from the group consisting of SEQ ID NO: 499-514, 2589-2591, 2982, 3511, 3805-3816, 5251-5309 and 5310. In another embodiment, the peptide of (h) has the sequence selected from the group consisting of SEQ ID NO: 515-516 and 517. In another embodiment, the peptide of (i) has the sequence selected from the group consisting of SEQ ID NO: 518-592, 2592-2609, 2983-3009, 3443-3444, 3512-3514, 3817-3859, 5311-5449 and 5450. In another embodiment, the peptide of (j) has the sequence selected from the group consisting of SEQ ID NO: 16-27, 593-636, 2610-2629, 3010-3039, 3860-3862, 5451-5501 and 5502. In another embodiment, the peptide of (k) has the sequence selected from the group consisting of SEQ ID NO: 637-645, 2630-2634, 3040-3042, 3863-3878, 5503-5581 and 5582. In another embodiment, the peptide of (l) has the sequence selected from the group consisting of SEQ ID NO: 28-32, 646-671, 2635-2639, 3043-3059, 3445-3447, 3515-3532, 3879-3941, 5583-5862 and 5863. In another embodiment, the peptide of (m) has the sequence selected from the group consisting of SEQ ID NO: 33-49, 672-725, 2640-2655, 3060-3082, 3448, 3533-3536, 3942-3973, 5864-5933 and 5934. In another embodiment, the peptide of (n) has the sequence selected from the group consisting of SEQ ID NO: 50-59, 726-736, 2656-2660, 3083-3104 and 3105. In another embodiment, the peptide of (o) has the sequence selected from the group consisting of SEQ ID NO: 60, 737-742, 2661-2662, 3106-3107, 3537-3538, 3974-3985, 5935-5979 and 5980. In another embodiment, the peptide of (p) has the sequence selected from the group consisting of SEQ ID NO: 743-745, 3539-3544, 3986-3998, 5981-6063 and 6064. In another embodiment, the peptide of (q) has the sequence selected from the group consisting of SEQ ID NO: 746-751, 2663, 3108-3110, 3449-3451, 3545-3548, 3999-4047, 6065-6179 and 6180. In another embodiment, the peptide of (r) has the sequence selected from the group consisting of SEQ ID NO: 752-812, 2664-2668, 3111-3125, 3549, 4048-4061, 6181-6250 and 6251. In another embodiment, the peptide of (s) has the sequence selected from the group consisting of SEQ ID NO: 813-819, 2669-2671, 3126-3130, 4062-4075, 6252-6309 and 6310. In another embodiment, the peptide of (t) has the sequence selected from the group consisting of SEQ ID NO: 820-824, 6311-6322 and 6323. In another embodiment, the peptide of (u) has the sequence selected from the group consisting of SEQ ID NO: 825-855, 2672-2678, 3131, 3550-3572, 4076-4106, 6324-6470 and 6471. In another embodiment, the peptide of (v) has the sequence selected from the group consisting of SEQ ID NO: 856-857 and 858. In another embodiment, the peptide of (w) has the sequence selected from the group consisting of SEQ ID NO: 859-863, 3132, 4107, 6472-6480 and 6481. In another embodiment, the peptide of (x) has the sequence selected from the group consisting of SEQ ID NO: 61-63, 864-866, 2679-2682, 3133-3136, 6482-6509 and 6510. In another embodiment, the peptide of (y) has the sequence selected from the group consisting of SEQ ID NO: 64-65, 867-875, 2683, 3137-3146, 4108, 6511-6524 and 6525. In another embodiment, the peptide of (z) has the sequence selected from the group consisting of SEQ ID NO: 876-894, 2684, 3147-3149, 6526 and 6527. In another embodiment, the peptide of (aa) has the sequence selected from the group consisting of SEQ ID NO: 895-905, 3150-3152, 4109, 6528-6556 and 6557. In another embodiment, the peptide of (bb) has the sequence selected from the group consisting of SEQ ID NO: 66-69, 899-905, 4110-4111, 6558-6570 and 6571. In another embodiment, the peptide of (cc) has the sequence selected from the group consisting of SEQ ID NO: 906-921, 2685, 3153-3156, 4112, 6572-6581 and 6582. In another embodiment, the peptide of (dd) has the sequence selected from the group consisting of SEQ ID NO: 70-73, 922-950, 2686-2703, 3157-3184, 3573-3574, 4113-4127, 6583-6706 and 6707. In another embodiment, the peptide of (ee) has the sequence selected from the group consisting of SEQ ID NO: 951-961, and 3185. In another embodiment, the peptide of (ff) has the sequence selected from the group consisting of SEQ ID NO: 962-1052, 2704-2721, 3186-3198, 3452, 3575-3579, 4128-4158, 6708-6752 and 6753. In another embodiment, the peptide of (gg) has the sequence selected from the group consisting of SEQ ID NO: 4159-4167, 6754-6804 and 6805. In another embodiment, the peptide of (hh) has the sequence selected from the group consisting of SEQ ID NO: 74, 1053-1059, 2722, 3199-3202, 3580, 4168-4180, 6806-6847 and 6848. In another embodiment, the peptide of (ii) has the sequence selected from the group consisting of SEQ ID NO: 6849-6850 and 6851. In another embodiment, the peptide of (jj) has the sequence selected from the group consisting of SEQ ID NO: 3453-3455, 3581-3588, 4181-4221, 6852-6938 and 6939. In another embodiment, the peptide of (kk) has the sequence selected from the group consisting of SEQ ID NO: 3589-3595, 4222-4262, 6940-7051 and 7052. In another embodiment, the peptide of (ll) has the sequence selected from the group consisting of SEQ ID NO: 75, 1060-1071, 2723-2729, 3203-3216, 3456-3457, 3596-3600, 4263-4297, 7053-7272 and 7273. In another embodiment, the peptide of (mm) has the sequence selected from the group consisting of SEQ ID NO: 76-77, 1072-1080, 3458, 3601, 4298-4311, 7274-7378 and 7379. In another embodiment, the peptide of (nn) has the sequence selected from the group consisting of SEQ ID NO: 4312-4317, 7380-7408 ad 7409. In another embodiment, the peptide of (oo) has the sequence selected from the group consisting of SEQ ID NO: 4318, 7410-7425 and 7426. In another embodiment, the peptide of (pp) has the sequence selected from the group consisting of SEQ ID NO: 3602, 4319-4327, 7427-7452 and 7453. In another embodiment, the peptide of (qq) has the sequence selected from the group consisting of SEQ ID NO: 3603, 4328-4378, 7454-7617 and 7618. In another embodiment, the peptide of (rr) has the sequence selected from the group consisting of SEQ ID NO: 1081-1183, 2730-2740, 3217-3221, 3459-3460, 3604-3634, 4379-4430, 7619-7693 and 7694. In another embodiment, the peptide of (ss) has the sequence selected from the group consisting of SEQ ID NO: 4431-4435, 7695-7711 and 7712. In another embodiment, the peptide of (tt) has the sequence selected from the group consisting of SEQ ID NO: 1184-1187, 4436, 7713-7751 and 7752. In another embodiment, the peptide of (uu) has the sequence selected from the group consisting of SEQ ID NO: 1188-1197, 2741-2747, 3222-3225, 4437-4444, 7753-7770 and 7771. In another embodiment, the peptide of (vv) has the sequence selected from the group consisting of SEQ ID NO: 4445-4447, 7772-7781 and 7782. In another embodiment, the peptide of (ww) has the sequence selected from the group consisting of SEQ ID NO: 78-111, 1198-1273, 2748-2788, 3226-3254, 3461-3463, 3635-3650, 4448-4565, 7783-8034 and 8035. In another embodiment, the peptide of (xx) has the sequence selected from the group consisting of SEQ ID NO: 112-151, 1274-1308, 2789-2825, 3255-3279, 3651-3655, 4566-4608, 8036-8179 and 8180. In another embodiment, the peptide of (yy) has the sequence selected from the group consisting of SEQ ID NO: 152-153, 1309-1329, 2826, 3280-3287, 3656, 8181-8200 and 8201. In another embodiment, the peptide of (zz) has the sequence selected from the group consisting of SEQ ID NO: 154-171, 1330-1385, 2827-2840, 3288-3301, 3464, 3657, 4609-4626, 8202-8309 and 8310. In another embodiment, the peptide of (aaa) has the sequence selected from the group consisting of SEQ ID NO: 4627, 8311-8212 and 8313. In another embodiment, the peptide of (bbb) has the sequence selected from the group consisting of SEQ ID NO: 172, 1386-1412, 2841-2845, 3302-3313, 3658-3661, 4628-4640, 8314-8338 and 8339. In another embodiment, the peptide of (ccc) has the sequence selected from the group consisting of SEQ ID NO: 3465-3467, 4641-4654, 8340-83402 and 8403. In another embodiment, the peptide of (ddd) has the sequence selected from the group consisting of SEQ ID NO: 1413-1417, 3314, 3468-3491, 3662-3674, 4655-4738, 8404-8619 and 8620. In another embodiment, the peptide of (eee) has the sequence selected from the group consisting of SEQ ID NO: 1418-1424, 2846-2856, 3315-3321, 3492-3494, 3675-3713, 4739-4823, 8621-8860 and 8861. In another embodiment, the peptide of (fff) has the sequence selected from the group consisting of SEQ ID NO: 1425-1432, 2857-2858, 3322-3329, 4824-4829, 8862-8900 and 8901. In another embodiment, the peptide of (ggg) has the sequence selected from the group consisting of SEQ ID NO: 173-175, 1433-1508, 2859-2872, 3330-3384, 4830-4833, 8902-8923 and 8924. In another embodiment, the peptide of (hhh) has the sequence selected from the group consisting of SEQ ID NO: 1509-1514, 3495, 3714-3725, 4834-4845, 8925-8948 and 8949. In another embodiment, the peptide of (iii) has the sequence selected from the group consisting of SEQ ID NO: 1515-1518, 2873, 4846-4850, 8950-8965 and 8966. In another embodiment, the peptide of (jjj) has the sequence selected from the group consisting of SEQ ID NO: 176-179, 1519-1532, 2874-2878, 3385-3392 and 3393. In another embodiment, the peptide of (kkk) has the sequence selected from the group consisting of SEQ ID NO: 180-204, 1533-1589, 2879-2891, 3394-3410, 3496-3498, 3726-3731, 4851-4922, 8967-9147 and 9148. In another embodiment, the peptide of (lll) has the sequence selected from the group consisting of SEQ ID NO: 4923-4931, 9149-9181 and 9182. In another embodiment, the peptide of (mmm) has the sequence selected from the group consisting of SEQ ID NO: 1590-1591, 2892, 3732-3733, 4932-4937, 9183-9227 and 9228. In another embodiment, the peptide of (nnn) has the sequence selected from the group consisting of SEQ ID NO: 205-207, 1592-1795, 2893-2911, 3411-3426, 3734-3745, 4938-4959, 9229-9287 and 9288. In another embodiment, the peptide of (000) has the sequence selected from the group consisting of SEQ ID NO: 208, 1796-1804, 2912-2913, and 3427. In another embodiment, the peptide of (ppp) has the sequence selected from the group consisting of SEQ ID NO: 4960-4976, 9289-9389 and 9390. In another embodiment, the peptide of (qqq) has the sequence selected from the group consisting of SEQ ID NO: 1805, 3746-3749, 4977-4988, 9391-9416 and 9417. In another embodiment, the peptide of (rrr) has the sequence selected from the group consisting of SEQ ID NO: 209-341, 1806-2482, 2914-2943, 3428-3439, 4989-4990, 9418-9431 and 9432. In another embodiment, the peptide of (sss) has the sequence selected from the group consisting of SEQ ID NO: 342-349, 2483-2553, 2944-2948, 3440-3442, 4991-4997, 9433-9439 and 9440. In another embodiment, the peptide of (ttt) has the sequence selected from the group consisting of SEQ ID NO: 4998-4999, 9441-9458 and 9459. In another embodiment, the peptide of (uuu) has the sequence of SEQ ID NO:2554. In another embodiment, the peptide of (vvv) has the sequence selected from the group consisting of SEQ ID NO: 9471-9472, and 9489. In another embodiment, the peptide of (www) has the sequence selected from the group consisting of SEQ ID NO: 9460-9469 and 9470. In another embodiment, the peptide of (xxx) has the sequence selected from the group consisting of SEQ ID NO: 9479-9480, and 9483. In another embodiment, the peptide of (yyy) has the sequence of SEQ ID NO:9487. In another embodiment, the peptide of (zzz) has the sequence selected from the group consisting of SEQ ID NO: 9473-9474, and 9488. In another embodiment, the peptide of (aaaa) has the sequence selected from the group consisting of SEQ ID NO: 9475-9476, and 9486. In another embodiment, the peptide of (bbbb) has the sequence selected from the group consisting of SEQ ID NO: 9477-9478, and 9485. In another embodiment, the peptide of (cccc) has the sequence selected from the group consisting of SEQ ID NO: 9481-9482, and 9484. In another or further embodiment of any of the foregoing embodiments, the peptide fragment is fused to a delivery peptide. In a further embodiment, the delivery peptide comprises a targeting peptide. In yet a further embodiment, the peptide fragment further comprises a cell penetrating peptide (CPP). In another embodiment, the delivery peptide comprises a cell penetrating peptide (CPP). In a further embodiment, the CPP is linked to the N-terminus or C-terminus of the peptide fragment. In a further embodiment, the fusion construct further comprises a peptide linker between the CPP and the peptide fragment. The disclosure also provide a peptide as described in any of the foregoing embodiments, wherein the peptide is linked to a nanoparticle. The disclosure also provides a polynucleotide or oligonucleotide encoding a peptide fragment of as describe above and herein. The disclosure further provides a vector comprising the polynucleotide or oligonucleotide. The vector can be a viral vector such as an adenoviral, gammaviral or lentiviral vector. The disclosure also provides a recombinant cell comprising an oligonucleotide, polynucleotide or vector of the disclosure.

The disclosure also provides a method of treating a cancer in a subject, comprising administering a composition comprising any one or more of (a)-(uuu) (above), wherein a peptide (a)-(uuu) has a dominant-negative effect and inhibits cancer growth, invasiveness or migration. In one embodiment, the cancer is selected from the group consisting of: adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), papillomas, actinic keratosis and keratoacanthomas, merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

The disclosure also provides a method of treating an infection by a betacoronavirus, the method comprising administering a composition of of any one or more of (vvv)-(cccc), wherein the composition inhibits the binding of a betacoronavirus to a receptor-ligand on a human cell.

The disclosure also provides a screening method to identify one or more peptide sequences that modulate functional regions of target protein(s), comprising: synthesizing a library of overlapping gene fragments from one or more genes that express the target protein(s), wherein each gene fragment has a unique nucleotide sequence, wherein each gene fragment from the same gene that express a target protein has a sequence which partial overlaps with the sequences of least two or more gene fragments having nucleotide sequences from the same gene; pooling and cloning the gene fragments into vectors, wherein each vector overexpresses one gene fragment when transduced or transfected into a cell; transfecting or transducing cells with the vectors comprising gene fragments, wherein each transduced or transfected cell has only one vector that comprises a gene fragment; screening the transfected or transduced cells for a phenotypic characteristic associated with target protein activity; sequencing and quantifying gene fragment abundance from cells exhibiting the phenotypic characteristic; and mapping the sequenced gene fragments back to the gene that express the target protein and providing a modulation score for each codon, wherein the modulation score is defined as the mean depletion/enrichment of all overlapping sequenced gene fragments, and wherein codons of the gene fragments which have a modulation score above or below a $p=0.05$ significance threshold, indicates peptide sequences which modulate functional regions of the target proteins. In one embodiment, the library of overlapping gene fragments is synthesized using pooled DNA oligonucleotide synthesis on a solid substrate. In another or further embodiment, the gene fragments are 60 nucleotides to 300 nucleotides in length. In another embodiment, the gene fragments are 120 nucleotides in length. In another embodiment, the target protein(s) are associated with a disease of disorder. In another embodiment, the disease or disorder is cancer, Alzheimer's disease or a neurodegenerative tauopathy disorder. In another embodiment, the genes expressing target proteins are tumor suppressor genes, pro-apoptotic genes or oncogenes. In another embodiment, the vectors are viral vectors. In another embodiment, the viral vectors are recombinant retroviral vectors, adenoviral vectors, adeno-associated viral vectors, alphaviral vectors, or lentiviral vectors. In another embodiment, the viral vectors are lentiviral vectors. In another embodiment, the phenotypic characteristic is cell growth. In another embodiment, the phenotypic characteristic is immunostimulatory/immunosuppressive activity. In another embodiment, the phenotypic characteristic is neurodegenerative tauopathy. In another embodiment, the modulation score is a depletion score indicating that the identified peptides inhibit or suppress the functional activity of target proteins. In another embodiment, the modulation score is an enrichment score indicating that the identified peptides enhance the functional activity of target proteins.

The disclosure also provides a screening method to identify one or more peptide sequences that inhibit functional regions of target protein(s) expressed by oncogenes, comprising: synthesizing a library of overlapping gene fragments from one or more oncogenes that express the target protein(s), wherein each gene fragment has a unique nucleotide sequence, wherein each gene fragment from the same gene that express a target protein has a sequence which partial overlaps with the sequences of least two or more gene fragments having nucleotide sequences from the same gene; pooling and cloning the gene fragments into vectors, wherein each vector overexpresses one gene fragment when transduced or transfected into a cell; transfecting or transducing cells with the vectors comprising gene fragments, wherein each transduced or transfected cell has only one vector that comprises a gene fragment; screening the transfected or transduced cells for cell growth over various time points; sequencing and quantifying gene fragment abundance from each of the time points; and mapping the sequenced gene fragments back to the oncogene that express the target protein and providing a depletion score for each codon, wherein the depletion score is defined as the mean depletion/enrichment of all overlapping sequenced gene fragments, and wherein codons of the gene fragments which have a depletion score below a $p=0.05$ significance threshold, indicates peptide sequences which inhibit functional regions of the target proteins expressed by the oncogenes. In another embodiment, the library of overlapping gene fragments is synthesized using pooled DNA oligonucleotide synthesis on a solid substrate. In another embodiment, the gene fragments are 60 nucleotides to 300 nucleotides in length. In another embodiment, the gene fragments are 120 nucleotides in length. In another embodiment, the vectors are viral vectors. In another embodiment, the viral vectors are recombinant retroviral vectors, adenoviral vectors, adeno-associated viral vectors, alphaviral vectors, or lentiviral vectors. In another embodiment, the viral vectors are lentiviral vectors. In another embodiment, the oncogenes includes one or more oncogenes selected from MCL-1, BCR, BRAF, JAK1, JAK2, VEGF, EGFR, ALK, CDK1, CDK2, CDK3, CDK3, CDK4, BRCA, PIK3CA, MEK, C-KIT, NRAS, ABCB11, ANTXR2, BCOR, CDKN1B, CYP27A1, EMD, FANCF, ABCC8, APC, BCORL1, CDKN2A, CYP27B1, EP300, FANCG, ABCC9, AR, BLM, CEP290, DAXX, EPCAM, FANCI, ABCD1, ARID1A, BMPR1A, CFTR, DBT, EPHAS, FANCL, ABL1, ARID2, RAF1, CHEK1, DCC, EPHB2, FANCM, ACADM, ARSA, BRCA1, CHEK2, DCX, ERBB2, FAS, CADS, ASAH1, BRCA2, CHM, DDB2, ERBB3, FAT3, ACADVL, ASCC1, BRIP1, CIC, DDR2, ERBB4, FBXO11, ACTC1, ASL, BTD, CLN3, DES, ERCC2, FBXO32, ACTN2, ASPA, BTK, CLNS, DHCR7, ERCC3, FBXW7, ACVR1B, ASS1, BUB1B, CLN6, DICER1, ERCC4, FGD4, ADA, ASXL1, CALR3, CLN8, DIS3L2, ERCC5, FGFR1, ADAMTS13, ATM, CARD11, COL1A2, DKC1, ERCC6, FGFR2, ADAMTS2, ATP4A, CASP8, COL4A3, DLD, ERRFI1, FGFR3, AGA, ATP6V0D2, CAV3, COL4A4, DMD, ESCO2, FH, AGL, ATP7A, CBFB, COL7A1, DNAJB2, ESR1, FKTN, AGPS, ATP7B, CBL, COX15, DNMT3A, ETV6, FLCN, AHI1, ATP8B1, CBLB, CREBBP, DSC2, EXOC2, FLT3, AIP, ATR, CBLC, CRLF2, DSE, EXT1, FMR1, AKAP9, ATRX, CBS, CRTAP, DSC2, EXT2, FUBP1, AKT1, AXIN1, CCDC178, CRYAB, DSP, EYA4, FZD3, AKT2, AXIN2, CCNE1, CSF1R, DTNA, EZH2, G6PC, ALB, BAG3, CD79A, CSMD3, ECT2L, F11, GAA, ALDH3A2, BAI3, CD79B, CSRP3, EDA, F5, GABRA6, ALDOB, BAP1, CD96, CTNNB1, EDN3, FAH, GALNT12, ALK, BARD1, CDC27, CTNS, EDNRB, FAM46C, GALT, ALS2, BAX, CDC73, CTSK, EED, FANCA, GATA1, AMER1, BAZ2B, CDH1, CUBN, EGFR, FANCB, GATA2, AMPD1, BCKDHA, CDH23, CYLD, EGR2, FANCC, GATA3, AMPH, BCKDHB, CDK12, CYP11A1, EHBP1, FANCD2, GATAD1, ANTXR1, BCL6, CDK4, CYP21A2, ELMO1, FANCE, GBA, GCDH, JAK1, MDM2, NEK2, PLOD1, ROS1, SMPD1, GJB2, JAK2, MECP2, NEXN, PLP1, RPGRIP1L, SOX10, GLA, JAK3, MED12, NF1, PMP22, RS1, SOX2, GLB1, JUP, MEFV, NF2, PMS2, RSPO1, SPEG, GLI1, KAT6A, MEN1, NFE2L2, POLD1, RTEL1, SPOP, GLI3, KCNQ1, MET, NFKBIA, POLE, RUNX1, SRC, GLMN, KDM4B, MFSD8, NIPA2, POLH, RUNX1T1, SSTR1, GNA11, KDM6A, MIER3, NKX3-1, POMGNT1, RYR2, STAG2, GNAQ, KDR, MITF, NOTCH1, POMT1, S1PR2, STAR, GNAS, KEAP1, MKS1, NOTCH2, POU1F1, SAMD9L, STK11, GNPTAB, KIF1B, MLH1, NPC1, POU6F2, SBDS, SUFU, GPC3, KIT, MLH3, NPC2, PPM1L, SCN11A, SUZ12, GPC6, KLF6, MMAB, NPHP1, PPP2R1A, SCN5A, SYNE3, GPR78, KLHDC8B, MPL, NPHP4, PPT1, SCNN1A, TAZ, GRIN2A, KMT2A, MPZ, NPM1, PRDM1, SCNN1B, TBX20, GRM8, KMT2C, MRE11A, PRKAG2, SCNN1G, TCAP, GXYLT1, KMT2D, MSH2, NRCAM, PRKAR1A, SCO2, TCERG1, H3F3A, KRAS, MSH3, NTRK1, PRKDC, SDHA, TCF7L2, HADHA, KREMEN1, MSH6, NUP62, PROC, SDHAF2, TERT, HADHB, L1CAM, MSMB, OR5L1, PROP1, SDHB, TET2, HBB, LAMA2, MSR1, OTC, PRPF40B, SDHC, TFG, HESX1, LAMA4, MTAP, OTOP1, PRX, SDHD, TGFB3, HEXA, LAMP2, MTHFR, PAH, PSAP, SEPT9, TGFBR1, HEXB, LDB3, MTM1, PALB2, PSEN1, SETBP1, TGFBR2, HFE, LEPRE1, MTOR, PALLD, PSEN2, SETD2, THSD7B, HGSNAT, LIG4, MUC16, PAX5, PTCH1, SF1, TINF2, HIST1H3B, LMNA, MUT, PAX6, PTCH2, SF3A1, TMC6, HNF1A, LPAR2, MUTYH, PBRM1, PTEN, SF3B1, TMC8, HRAS, LRP1B, MYBPC3, PCDH15, PTGFR, SGCD, TMEM127, HSPH1, LRPPRC, MYC, PCGF2, PTPN11, SGSH, TMEM43, IDH1, LRRK2, MYD88, PDE11A, PTPN12, SH2B3, TMEM67, IDH2, LYST, MYH6, PDGFRA, RAC1, SLC25A4, TMPO, IGF2R, MAP2K1, MYH7, PDHA1, RAD21, SLC26A2, TNFAIP3, IGHMBP2, MAP2K2, MYL2, PDZRN3, RAD50, SLC37A4, TNFRSF14, IGSF10, MAP2K4, MYL3, PEX1, RAD51B, SLC7A8, TNNC1, IKBKAP, MAP3K1, MYLK2, PEX7, RAD51C, SLC9A9, TNNI3, IKZF1, MAP4K3, MYO1B, PHF6, RAD51D, SLX4, TNNT1, IKZF4, MAP7, MYO7A, PIK3CA, RARB, SMAD2, TNNT2, IL2RG, MAPK10, MYOZ2, PIK3CG, RB1, SMAD4, TP53, IL6ST, MAS1L, MYPN, PIK3R1, RBM20, SMARCA4, TPM1, IL7R, MAX, NBN, PKHD1, RECQL4, SMARCB1, TPP1, INVS, MC1R, NCOA2, PKP2, RET, SMC1A, TRAF5, IRAK4, MCCC2, NCOR1, PLEKHG5, RHBDF2, SMC3, TRIO, ITCH, MCOLN1, NDUFA13, PLN, RNASEL, SMO, TRPV4, TRRAP, U2AF1, USH1C, WAS, WWP1, ZIC3, TSC1, U2AF2, USH1G, WBSCR17, XPA, ZNF2, TSC2, UBA1, USP16, WEE1, XPC, ZNF226, TSHB, UBR3, USP25, WNK2, XRCC3, ZNF473, TSHR, UROD, VCL, WRN, ZBED4, ZNF595, TTN, UROS, VHL, WT1, ZFHX3, HER2, and ZRSR2. In another embodiment, the one or more oncogenes are selected from KRAS, HRAS, NRAS, RAF1, BRAF, ARAF, Myc, Max, FBXW7, and EGFR. The disclosure also provides a peptide comprising a sequence that inhibits functional regions of target protein(s) expressed by oncogenes identified by the method of the disclosure. In another embodiment, the peptide inhibits the functional regions of EGFR and has the sequence of EGFR-697 or inhibits the function regions of RAF1 and has the sequence of RAF1-73.

The disclosure also provides an isolated polypeptide or peptide comprising, consisting essentially of or consisting of a sequence that is 85%, 87%, 90%, 92%, 94%, 95%, 98%, 99% or 100% identical to any one sequence as set forth SEQ ID NOs: 1-9489. In another embodiment, the peptide inhibits cancer cell growth, invasion, metastasis, and/or migration or inhibits the ability of a betacoronavirus to infect a cell. In another embodiment, the peptide further comprises a cell penetrating peptide (CPP) linked to the N-terminus or C-terminus of the isolated polypeptide or peptide. In another embodiment, the construct comprises a peptide linker between the CPP and the polypeptide or peptide. In still another embodiment, a nanoparticle can be linked to a polypeptide or peptide of the disclosure.

DESCRIPTION OF DRAWINGS

FIG. 6A-G shows overall analyses and extended metrics for expanded cancer driver screens: (A) Table detailing all the peptides assayed in the expanded wildtype driver screen.

Figure 1A:
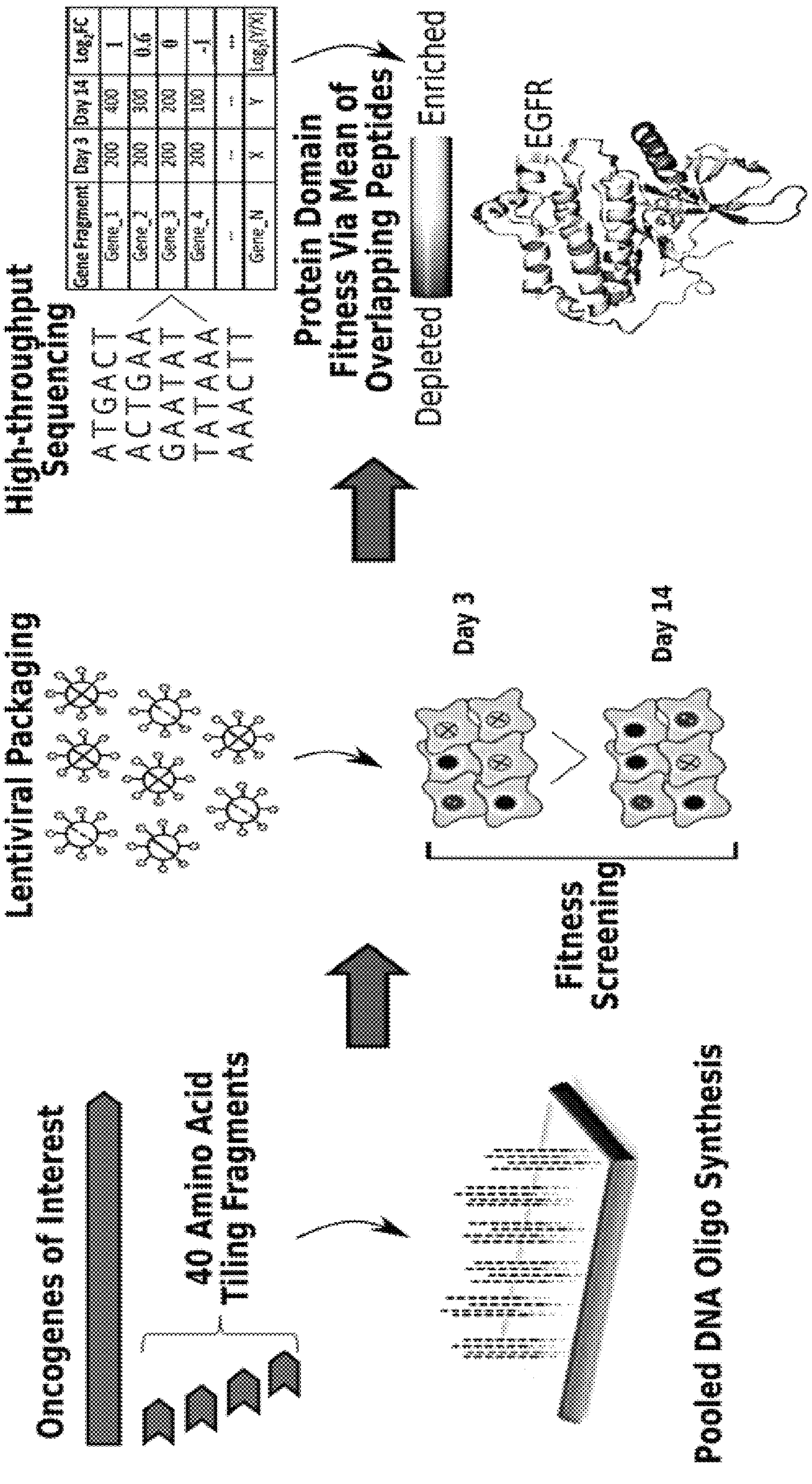
FIG. 1A-C shows an overview of experimental design and initial results: (A) Design of overlapping gene fragment library. Gene fragments coding for all possible overlapping 40 mer peptides were computed from target gene cDNA sequences. Gene fragment sequences were then generated via chip-based oligonucleotide synthesis and cloned into a lentiviral plasmid vector. This plasmid library was in turn used to generate lentiviral particles via transient transfection. The lentiviral particles were then used to infect target mammalian cell lines at a low MOI to ensure only one gene fragment was expressed per cell. The cells were then grown for two weeks, with genomic DNA extracted at day 3 and day 14. Next, gene fragments were PCR amplified from genomic DNA and sequenced to track fragment abundances and calculate $\log_2$ enrichment and depletion. Gene fragments were mapped back to target gene coding sequences, and each codon/amino acid was given a fitness score defined as the Z-normalized mean $\log_2$ fold change of all overlapping gene fragments. (B) Resulting amino acid level fitness scores. Screening data from Hs578T and MDA-MB-231 cells shows conserved regions of fitness dependencies, as well as cell line specific fitness dependencies. The heatmap shows the fitness score for each amino acid position (sorted in ascending order from top to bottom) across all proteins assayed in the screen. On the right, plots showing the statistical likelihood of depletion are shown for RAF1, EGFR, BRAF, and FBXW7. Peptides overlapping amino acid positions with known functional roles are significantly depleted over the course of cell growth. (C) The fitness effects of peptides derived from known pathogenic and dominant negative Ras mutants. KRASQ61K is significantly depleted in both cell lines, while HRAS S17N is depleted only in HRAS mutant Hs578T cells.

Genes comprising diverse cancer associated signaling pathways and processes. (B) Computed per position amino acid scores had good correlation between replicates (Pearson=0.917), with reproducibility exceeding that of the pilot screen. It was hypothesized the greater effect size of deleterious peptides contained in the larger library (see FIG. 2A) likely drives improved signal to noise ratio. As in the pilot screen the majority of amino acid positions in the full-length protein structures are not implicated in cell fitness, consistent with accepted understanding that protein-protein interactions directly driving oncogenic proliferation are rare. (C) The fitness score for the most deleterious residue in each full-length protein is plotted for each gene. GFP and HPRT1 controls show little effect on cell fitness across protein structure. (D) Per position fitness scores for RASA1, RRAS2, FLT3, DICER1, RB1, and ERBB4. Select PPIs are annotated on the plots, corresponding to regions of significant depletion. (E) Replicate correlation for mutant peptide screen. Screen shows high degree of reproducibility (Pearson correlation=0.859). As in the previously presented screens, the majority of mutant amino acid motifs assayed have no effect on cell fitness. (F) Table detailing all the peptides assayed in the mutant screen. Mutant genes cover a wide range of signaling pathways and molecular functions. (G) Plot of wild type (gray bars) and mutant amino acid fitness scores (points) for PIK3CA, BRAF, and SMAD4. Points labeled in red were significantly (BH adjusted P value <0.05) depleted in the pooled screen.

FIG. 7A-E shows individual validations of antiproliferative peptides: (A-B) Plots showing the correlation between peptide depletion versus charge and hydrophobicity. There is little correlation between charge/hydrophobicity and peptide log fold change, indicating that gross physiochemical factors do not mediate peptide effects on fitness. (C) Growth kinetics in Hs578T for individual peptide variants shown in FIG. 3A. Cell growth was quantified via the WST-8 proliferation assay. Results are from the same experiment split into multiple plots for ease of visualization, hence identical GFP controls for each peptide group. Arrayed validation of lentivirally delivered gene fragments derived from KRAS mutants is also shown. KRAS61K mutant peptides predicted to be deleterious to cell growth significantly inhibited growth (P<0.05, as measured at the 7 day time point). (D) Growth kinetics in MDA-MB-231 for individual peptide variants shown in FIG. 3A. Cell growth was quantified via the WST-8 proliferation assay. Results are from the same experiment split into multiple plots for ease of visualization, hence identical GFP controls for each peptide group. Arrayed validation of lentivirally delivered gene fragments derived from KRAS mutants is also shown. KRAS61K mutant peptides predicted to be deleterious to cell growth significantly inhibited growth (P<0.05, as measured at the 7 day time point). (E) Validation of peptide expression via immunofluorescence. Peptides were transduced with lentivirus 72 hours before immunostaining and imaging.

Figure 8A:
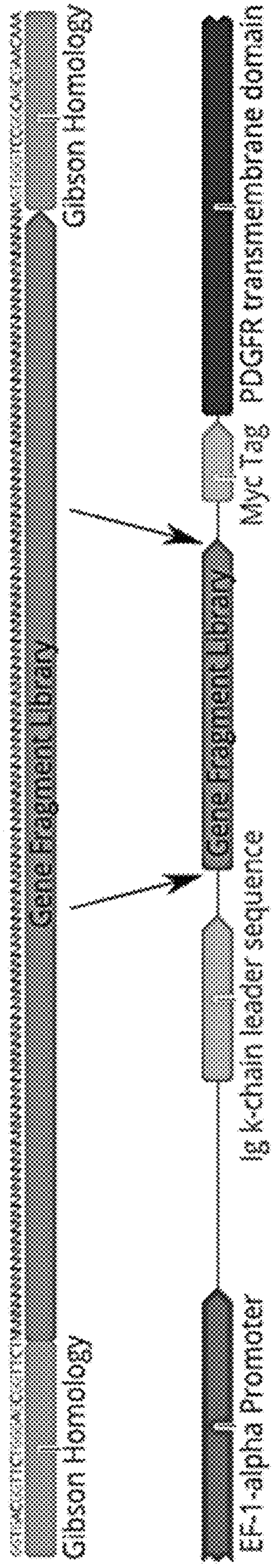
Figure 8B:
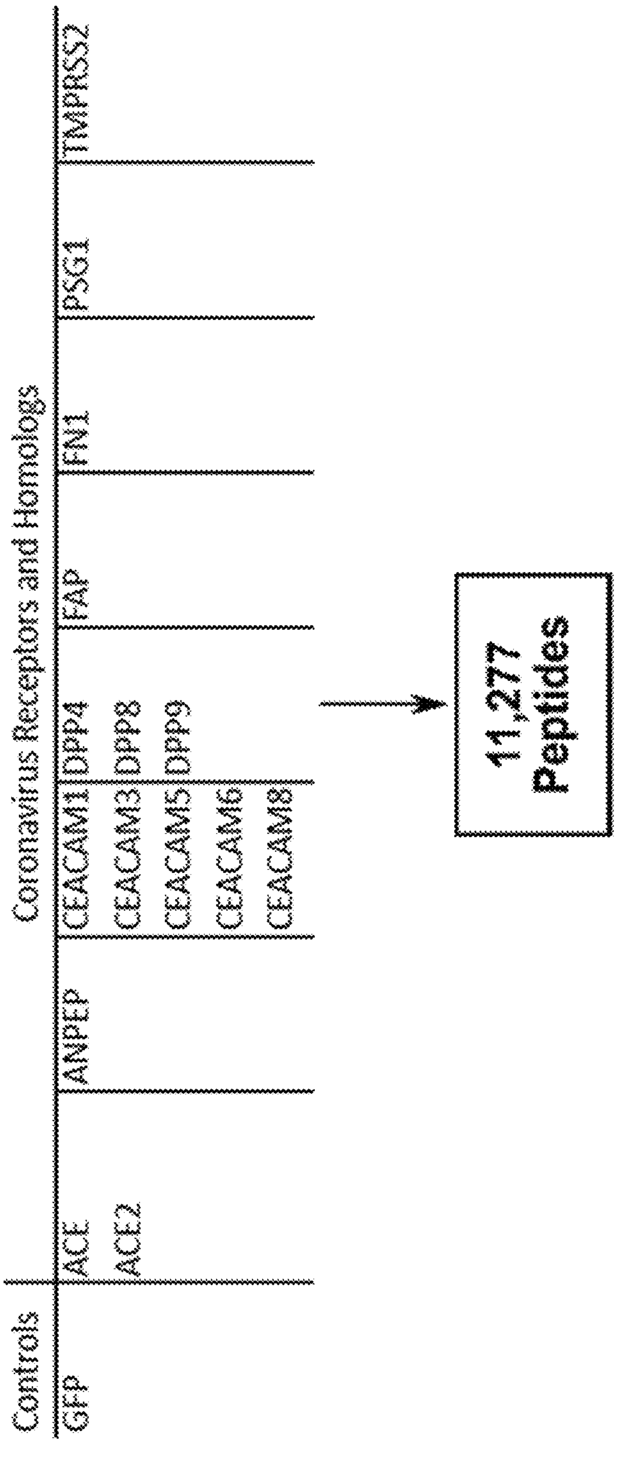

FIG. 8A-C shows Betacoronavirus peptide library cloning strategy and computational validation: (A) Cloning strategy and vector design for cell surface PepTile. Gene fragment libraries were synthesized as single stranded oligonucleotides and converted to double stranded DNA via PCR (depicted is SEQ ID NO: 9720). This library was then cloned into a cell surface expression vector via Gibson Assembly. Cell surface expression was obtained by cloning the gene fragment library between an N-terminal Ig Kappa leader peptide (to ensure secretion), and the PDGFR transmembrane domain (to provide anchoring on the cell membrane). (B) Genes from which peptide library was derived. Genes were chosen based on involvement in SARS-COV-2, SARS-COV, and/or MERS-COV cell entry. (C) Structural justification for ACE2 peptide inhibition: X-ray crystallography and Cryo-EM structures of SARS-COV2 spike protein receptor binding domain (RBD) complexed with ACE2 reveal that the binding interface stretches along two antiparallel alpha helices in the N-terminal domain of the protein (PDB structures 6M17, 6LZG, and 6M0J) 86-88. As specific examples, peptides covering each of these two helices and homologous ones from related proteins are shown sequentially below the structures (SEQ ID Nos: 9702-9718).

DETAILED DESCRIPTION

As used herein and in the appended claims, the singular forms "a," "an," and "the" include plural referents unless the context clearly dictates otherwise. Thus, for example, reference to "a cell" includes a plurality of such cells and reference to "the fragment" includes reference to one or more fragments and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

It should be understood that this disclosure is not limited to the particular methodology, protocols, and reagents, etc., described herein and as such may vary. The terminology used herein is for the purpose of describing particular embodiments or aspects only and is not intended to limit the scope of the present disclosure.

Other than in the operating examples, or where otherwise indicated, all numbers expressing quantities of ingredients or reaction conditions used herein should be understood as modified in all instances by the term "about." The term "about" when used to described the present invention, in connection with percentages means±1%. The term "about," as used herein can mean within an acceptable error range for the particular value as determined by one of ordinary skill in the art, which can depend in part on how the value is measured or determined, e.g., the limitations of the measurement system. Alternatively, "about" can mean a range of plus or minus 20%, plus or minus 10%, plus or minus 5%, or plus or minus 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value can be assumed. Also, where ranges and/or subranges of values are provided, the ranges and/or subranges can include the endpoints of the ranges and/or subranges. In some cases, variations can include an amount or concentration of 20%, 10%, 5%, 1%, 0.5%, or even 0.1% of the specified amount.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and o-phosphoserine. In some embodiments, an amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. In some embodiments, an amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature. In certain instances one or more D-amino acids can be used in various peptide compositions of the disclosure. The disclosure provides various peptides that are useful for treating various diseases and infections. These peptides can comprise naturally occurring amino acid. In other embodiments, the peptides can comprise non-natural amino acids. The use of non-natural amino acids can improve the peptides stability, decrease degradation and/or improve biological activity. For example, in some embodiments, one or more D-amino acids. In other embodiments, retroinverso peptides are contemplated using various amino acid configurations.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

For purposes of the disclosure the term "cancer" will be used to encompass cell proliferative disorders, neoplasms, precancerous cell disorders and cancers, unless specifically delineated otherwise. Thus, a "cancer" refers to any cell that undergoes aberrant cell proliferation that can lead to metastasis or tumor growth. Exemplary cancers include but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), papillomas, actinic keratosis and keratoacanthomas, merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In a particular embodiment, the cancer can be selected from the group consisting of melanoma, colorectal cancer, pancreatic cancer, bladder cancer, breast cancer, triple negative breast cancer, ovarian cancer and lung cancer.

"Cells" according to the disclosure include any cell into which foreign gene fragments can be introduced and expressed as described herein or into which a drug-like peptide of the disclosure can be delivered. It is to be understood that the basic concepts of the disclosure described herein are not limited by cell type. Foreign gene fragments (i.e., those which are not part of a cell's natural nucleic acid composition) may be introduced into a cell using any method known to those skilled in the art for such introduction. Such methods include transfection, transduction, infection (e.g., viral transduction), injection, microinjection, gene gun, nucleofection, nanoparticle bombardment, transformation, conjugation, by application of the nucleic acid in a gel, oil, or cream, by electroporation, using lipid-based transfection reagents, or by any other suitable transfection method. One of skill in the art will readily understand and adapt such methods using readily identifiable literature sources.

The term "contacting" can mean direct or indirect binding or interaction between two or more entities. An example of direct interaction is binding. An example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

As used herein, the term "detectable marker" or "selectable marker" can refer to at least one marker capable of directly or indirectly, producing a detectable signal. A non-exhaustive list of this marker includes enzymes which produce a detectable signal, for example by colorimetry, fluorescence, luminescence, such as horseradish peroxidase, alkaline phosphatase, β-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection can be accomplished by optical methods such as diffraction, surface plasmon resonance, surface variation, the contact angle change or physical methods such as atomic force spectroscopy, tunnel effect, or radioactive molecules such as 32 P, 35 S or 125 I.

As used herein, the term "domain" can refer to a particular region of a protein or polypeptide, which can be associated with a particular function. For example, "a domain which binds to a cognate" can refer to the domain of a protein that binds one or more receptors or other protein moieties and (i) block the biological effect of a molecule that typically binds to the same receptor or protein or modulate the effect (i.e., increase or decrease) the biological activity of the naturally occurring binding partner of the protein or receptor.

As used herein the term "dominant-negative activity" can refer to the ability of a peptide or polypeptide of the disclosure to act as an inhibitor by binding to the wild type protein from which it is derived (i.e., from which it shares identity) or by titrating an essential ligand that binds with the protein from which the peptide is derived.

As used herein a "drug-like peptide" can refer to a polymer of amino acids comprising amide bonds that form a peptide, which does not occur in nature and which can be delivered to a cell, tissue or subject such that the biological effect results in a treatment of a disease, disorder infection or inhibits the progression of a disease, disorder or infection or which can prevent getting the disease, disorder or infection. In one embodiment, a drug-like peptide is a peptide having the sequence of any one of SEQ ID Nos: 1-9489. In another embodiment, a drug-like peptide is a peptide that is at least 95%, 96%, 97%, 98%, or 99% identical to a peptide having the sequence of any of SEQ ID Nos: 1-9489. In still another embodiment, a drug-like peptide has the sequence of any one of SEQ ID Nos: 1-9489, wherein one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40) of the amino acids is substitute with a non-naturally occurring or D-amino acid and which has the same biological activity (not necessarily to the same degree) as a peptide of the same sequence having all L-amino acids. A drug-like peptide can be formulated for suitable routes of delivery as a pharmaceutical composition and/or linked to a second domain having a similar or different biological activity. In some instances, a drug-like peptide can be fused to a peptide that functions to assist in delivery and/or uptake by a cell (e.g., a protein transduction domain).

The term "encode" as it is applied to polynucleotides can refer to a polynucleotide which is said to "encode" a polypeptide if, in its native state or when manipulated by methods well known to those skilled in the art, it can be transcribed and/or translated to produce the mRNA for the polypeptide and/or a fragment thereof. In some cases the antisense strand is the complement of such a nucleic acid, and the encoding sequence can be deduced therefrom.

The terms "equivalent" or "biological equivalent" are used interchangeably when referring to a particular molecule, biological, or cellular material and intend those having minimal homology while still maintaining desired structure or functionality.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. One example of a membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

As used herein, "expression" can refer to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell.

"Homology" or "identity" or "similarity" can refer to sequence similarity between two peptides or between two nucleic acid molecules. Homology can be determined by comparing a position in each sequence which can be aligned for purposes of comparison. For example, when a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the disclosure.

Homology refer to a percent (%) identity of a sequence to a reference sequence. As a practical matter, whether any particular sequence can be at least 50%, 60%, 70%, 80%, 85%, 90%, 92%, 95%, 96%, 97%, 98% or 99% identical to any sequence described herein, such particular peptide, polypeptide or nucleic acid sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence, the parameters can be set such that the percentage of identity is calculated over the full length of the reference sequence and that gaps in homology of up to 5% of the total reference sequence are allowed.

For example, in a specific embodiment the identity between a reference sequence (query sequence, i.e., a sequence of the disclosure) and a subject sequence, also referred to as a global sequence alignment, can be determined using the FASTDB computer program based on the algorithm of Brutlag et al. (Comp. App. Biosci. 6:237-245 (1990)). In some cases, parameters for a particular embodiment in which identity is narrowly construed, used in a FASTDB amino acid alignment, can include: Scoring Scheme=PAM (Percent Accepted Mutations) 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject sequence, whichever is shorter. According to this embodiment, if the subject sequence is shorter than the query sequence due to N- or C-terminal deletions, not because of internal deletions, a manual correction can be made to the results to take into consideration the fact that the FASTDB program does not account for N- and C-terminal truncations of the subject sequence when calculating global percent identity. For subject sequences truncated at the N- and C-termini, relative to the query sequence, the percent identity can be corrected by calculating the number of residues of the query sequence that are lateral to the N- and C-terminal of the subject sequence, which are not matched/aligned with a corresponding subject residue, as a percent of the total bases of the query sequence. A determination of whether a residue is matched/aligned can be determined by results of the FASTDB sequence alignment. This percentage can be then subtracted from the percent identity, calculated by the FASTDB program using the specified parameters, to arrive at a final percent identity score. This final percent identity score can be used for the purposes of this embodiment. In some cases, only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence are considered for this manual correction. For example, a 90 residue subject sequence can be aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity can be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for.

"Hybridization" can refer to a reaction in which one or more polynucleotides react to form a complex that is stabilized via hydrogen bonding between the bases of the nucleotide residues. The hydrogen bonding can occur by Watson-Crick base pairing, Hoogstein binding, or in any other sequence-specific manner. The complex can comprise two strands forming a duplex structure, three or more strands forming a multi-stranded complex, a single self-hybridizing strand, or any combination of these. A hybridization reaction can constitute a step in a more extensive process, such as the initiation of a PC reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1x SSC to about 0.1× SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

The term "isolated" as used herein can refer to molecules or biologicals or cellular materials being substantially free from other materials. In one aspect, the term "isolated" can refer to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also can refer to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and may not be found in the natural state. In some cases, the term "isolated" is also used herein to refer to polypeptides which are isolated from other cellular proteins and is meant to encompass both purified and recombinant polypeptides. In some cases, the term "isolated" is also used herein to refer to cells or tissues that are isolated from other cells or tissues and is meant to encompass both cultured and engineered cells or tissues.

"Messenger RNA" or "mRNA" is a nucleic acid molecule that is transcribed from DNA and then processed to remove non-coding sections known as introns. In some cases, the resulting mRNA is exported from the nucleus (or another locus where the DNA is present) and translated into a protein. The term "pre-mRNA" can refer to the strand prior to processing to remove non-coding sections.

The term "microorganism" or "microbe" refers to a microscopic organism, especially a bacterium, virus, or fungus.

The term "protein", "peptide" and "polypeptide" are used interchangeably and in their broadest sense to refer to a compound of two or more subunit amino acids, amino acid analogs or peptidomimetics. The subunits can be linked by peptide bonds. In another embodiment, the subunit can be linked by other bonds, e.g., ester, ether, etc. A protein or peptide can contain at least two amino acids and no limitation is placed on the maximum number of amino acids which can comprise a protein's or peptide's sequence. As mentioned above, the term "amino acid" can refer to either natural and/or unnatural or synthetic amino acids, including glycine and both the D and L optical isomers, amino acid analogs and peptidomimetics. As used herein, the term "fusion protein" can refer to a protein comprised of domains from more than one naturally occurring or recombinantly produced protein, where generally each domain serves a different function. In this regard, the term "linker" can refer to a peptide fragment that is used to link these domains together—optionally to preserve the conformation of the fused protein domains and/or prevent unfavorable interactions between the fused protein domains which can compromise their respective functions.

The terms "polynucleotide" and "oligonucleotide" are used interchangeably and refer to a polymeric form of nucleotides of any length, either deoxyribonucleotides or ribonucleotides or analogs thereof. Polynucleotides can have any three dimensional structure and can perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also can refer to both double and single stranded molecules. Unless otherwise specified or required, any embodiment of this disclosure that is a polynucleotide can encompass both the double stranded form and each of two complementary single stranded forms known or predicted to make up the double stranded form.

The term "polynucleotide sequence" can be the alphabetical representation of a polynucleotide molecule. This alphabetical representation can be input into databases in a computer having a central processing unit and used for bioinformatics applications such as functional genomics and homology searching.

Similarly, the term "polypeptide sequence", "peptide sequence" or "protein sequence" can be the alphabetical representation of a polypeptide molecule. This alphabetical representation can be input into databases in a computer having a central processing unit and used for bioinformatics applications such as functional proteomics and homology searching.

As used herein, the term "recombinant expression system" refers to a genetic construct or constructs for the expression of certain genetic material formed by recombination.

As used herein, the term "recombinant protein" can refer to a polypeptide or peptide which is produced by recombinant DNA techniques, wherein generally, DNA encoding the polypeptide or peptide is inserted into a suitable expression vector which is in turn used to transform a host cell to produce the heterologous polypeptide or peptide.

The term "sample" as used herein, generally refers to any sample of a subject (such as a blood sample or a tissue sample). A sample can comprise a tissue, a cell, serum, plasma, exosomes, a bodily fluid, or any combination thereof. A bodily fluid can comprise urine, blood, serum, plasma, saliva, mucus, spinal fluid, tears, semen, bile, amniotic fluid, or any combination thereof. A sample or portion thereof can comprise an extracellular fluid obtained from a subject. A sample or portion thereof can comprise cell-free nucleic acid, DNA or RNA. A sample can be a sample removed from a subject via a non-invasive technique, a minimally invasive technique, or an invasive technique. A sample or portion thereof can be obtained by a tissue brushing, a swabbing, a tissue biopsy, an excised tissue, a fine needle aspirate, a tissue washing, a cytology specimen, a surgical excision, or any combination thereof. A sample or portion thereof can comprise tissues or cells from a tissue type. For example, a sample can comprise a nasal tissue, a trachea tissue, a lung tissue, a pharynx tissue, a larynx tissue, a bronchus tissue, a pleura tissue, an alveoli tissue, breast tissue, bladder tissue, kidney tissue, liver tissue, colon tissue, thyroid tissue, cervical tissue, prostate tissue, heart tissue, muscle tissue, pancreas tissue, anal tissue, bile duct tissue, a bone tissue, brain tissue, spinal tissue, kidney tissue, uterine tissue, ovarian tissue, endometrial tissue, vaginal tissue, vulvar tissue, uterine tissue, stomach tissue, ocular tissue, sinus tissue, penile tissue, salivary gland tissue, gut tissue, gallbladder tissue, gastrointestinal tissue, bladder tissue, brain tissue, spinal tissue, a blood sample, or any combination thereof.

The term "sequencing" as used herein, can comprise bisulfite-free sequencing, bisulfite sequencing, TET-assisted bisulfite (TAB) sequencing, ACE-sequencing, high-throughput sequencing, Maxam-Gilbert sequencing, massively parallel signature sequencing, Polony sequencing, 454 pyrosequencing, Sanger sequencing, Illumina sequencing, SOLiD sequencing, Ion Torrent semiconductor sequencing, DNA nanoball sequencing, Heliscope single molecule sequencing, single molecule real time (SMRT) sequencing, nanopore sequencing, shot gun sequencing, RNA sequencing, Enigma sequencing, or any combination thereof.

The term "subject" as used herein, refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein. For example, a mammalian subject can refer to a human patient.

As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, CA), LIPOFECTAMINE® (Invitrogen), FUGENE® (Roche Applied Science, Basel, Switzerland), JETPEI™ (Polyplus-transfection Inc., New York, NY), EFFECT-ENE® (Qiagen, Valencia, CA), DREAMFECT™ (OZ Biosciences, France) and the like), or electroporation. Suitable methods for transforming or transfecting host cells can be found in Sambrook, et al. (Molecular Cloning: A Laboratory Manual. 2nd, ed., Cold Spring harbor Laboratory, Cold Spring Harbor Laboratory Press, Cold Spring Harbor, N.Y., 1989), and other laboratory manuals. Standard recombinant DNA and molecular cloning techniques used herein are well known in the art and are described in Sambrook, J., Fritsch, E. F. and Maniatis, T., Molecular Cloning: A Laboratory Manual, $2^{nd}$ ed.; Cold Spring Harbor Laboratory: Cold Spring Harbor, N.Y., (1989) and by Silhavy, T. J., Bennan, M. L. and Enquist, L. W., Experiments with Gene Fusions; Cold Spring Harbor Laboratory: Cold Spring Harbor, N.Y., (1984); and by Ausubel, F. M. et. al., Current Protocols in Molecular Biology, Greene Publishing and Wiley-Interscience (1987) each of which are hereby incorporated by reference in its entirety. Additional useful methods are described in manuals including Advanced Bacterial Genetics (Davis, Roth and Botstein, Cold Spring Harbor Laboratory, 1980), Experiments with Gene Fusions (Silhavy, Berman and Enquist, Cold Spring Harbor Laboratory, 1984), Experiments in Molecular Genetics (Miller, Cold Spring Harbor Laboratory, 1972) Experimental Techniques in Bacterial Genetics (Maloy, in Jones and Bartlett, 1990), and A Short Course in Bacterial Genetics (Miller, Cold Spring Harbor Laboratory 1992) each of which are hereby incorporated by reference in its entirety.

The terms “treat”, “treating” and “treatment”, as used herein, refers to ameliorating symptoms associated with a disease or disorder (e.g., cancer, Covid-19 etc.), including preventing or delaying the onset of the disease or disorder symptoms, and/or lessening the severity or frequency of symptoms of the disease or disorder.

As used herein, the term “vector” can refer to a nucleic acid construct deigned for transfer between different hosts, including but not limited to a plasmid, a virus, a cosmid, a phage, a BAC, a YAC, etc. In some embodiments, a “viral vector” is defined as a recombinantly produced virus or viral particle that comprises a polynucleotide to be delivered into a host cell, either in vivo, ex vivo or in vitro. In some embodiments, plasmid vectors can be prepared from commercially available vectors. In other embodiments, viral vectors can be produced from baculoviruses, retroviruses, adenoviruses, AAVs, etc. according to techniques known in the art. In one embodiment, the viral vector is a lentiviral vector. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct can refer to the polynucleotide comprising the retroviral genome or part thereof, and a gene of interest. Further details as to modern methods of vectors for use in gene transfer can be found in, for example, Kotterman et al. (2015) Viral Vectors for Gene Therapy: Translational and Clinical Outlook Annual Review of Biomedical Engineering 17. Vectors that contain both a promoter and a cloning site into which a polynucleotide can be operatively linked are well known in the art. Such vectors are capable of transcribing RNA in vitro or in vivo and are commercially available from sources such as Agilent Technologies (Santa Clara, Calif.) and Promega Biotech (Madison, Wis.). In one aspect, the promoter is a pol III promoter.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as “expression vectors.” In general, expression vectors of utility in recombinant DNA techniques are often in the form of plasmids. In the present specification, “plasmid” and ‘Vector” can be used interchangeably. However, the disclosure is intended to include such other forms of expression vectors, such as viral vectors (e.g., replication defective retroviruses, adenoviruses and adeno-associated viruses), which serve equivalent functions. Typically, the vector or plasmid contains sequences directing transcription and translation of a relevant gene or genes, a selectable marker, and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host.

Typically, the vector or plasmid contains sequences directing transcription and translation of a gene fragment, a selectable marker, and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, IPL, IPR, T7, tac, and trc (useful for expression in Escherichia coli and Pseudomonas); the amy, apr, npr promoters and various phage promoters useful for expression in *Bacillus subtilis*, and *Bacillus licheniformis*; nisA (useful for expression in gram positive bacteria, Eichenbaum et al. Appl. Environ. Microbiol. 64(8):2763-2769 (1998)); and the synthetic P11 promoter (useful for expression in *Lactobacillus plantarum*, Rud et al., Microbiology 152:1011-1019 (2006)). Termination control regions may also be derived from various genes native to the preferred hosts.

Genetic screening has rapidly become a ubiquitous tool to probe protein function and accelerate drug discovery. Libraries of genetically encoded perturbations (CRISPR-Cas9 sgRNA, siRNA, etc.) enable high throughput identification of proteins essential to cancer cells fitness, disease progression and infectivity. However, existing screens typically fail to capture how proteins function biologically and provide little information on how to target hits therapeutically. Transposon mediated fragmentation and overexpression of cDNA has been used to identify peptide inhibitors of essential proteins in *Saccharomyces cerevisiae*. However, these libraries randomly generate gene fragments of various lengths hindering control of library composition, feature many out of frame fragments, and are limited in their translational relevance due to the choice of model organism. To overcome these challenges, provided herein is a platform-based screening methodology that uses overexpressed libraries of overlapping synthesized gene fragments that can be used to identify protein functional regions associated with an abnormal or disease cell fitness (e.g., cancer cell fitness), as well as dominant negative inhibitors of abnormal or disease cell growth (e.g., cancer cell growth) and as inhibitors of infectious agents.

Inhibitory peptides have immense potential as both research tools and therapeutics. Direct inhibition of protein activity without genetic alteration opens unique screening avenues with which to probe protein function. For example, protein-protein interaction networks could be more precisely perturbed via inhibitory peptides contacting a specific protein surface in contrast to complete genetic knockdown. The ability to identify protein regions associated with cell fitness can also serve to complement traditional drug development efforts, such as through determining critical residues for inhibition via small molecules or antibodies. Additionally, this screening method identifies inhibitory peptides that are immediately translatable, bypassing the need for additional high-throughput screens to identify candidate molecules.

Many proteins can be inhibited in a dominant negative fashion by short peptides/proteins derived from their own wild type coding sequence. Leveraging this fact, the disclosure provides compositions and methods that use a comprehensive lentiviral library of gene fragments tiling key oncogenes via a highly modular oligonucleotide synthesis protocol. This library was then used to conduct a pooled fitness screen, mining novel peptide motifs which selectively reduce cellular proliferation in breast cancer cell lines dependent on Ras/Myc signaling. Furthermore, by mapping peptides to their parent oncogenes (see, e.g., Table 1), conserved regions of depletion which revealed protein domains essential for cell fitness were identified. Coupling of cell penetrating motifs or other peptide delivery compositions to these peptides provides a drug-like function. Using the screening methods described herein, drugable peptide compositions were developed, such as for example, from EGFR and RAF1 which were able to inhibiting cell growth at $IC_{50}$s of 30-60 μM. Taken together, this approach enabled rapid discovery of potentially translatable peptide therapeutics, as well as de novo mapping of essential protein domains.

The screening strategy presented herein can probe protein functional regions with single amino acid resolution and can be readily scalable due to the ease of array-based oligonucleotide synthesis. In the exemplary studies presented herein, the platform-based screening methodology disclosed can identify peptide inhibitors of known oncogenes, including proteins, such as KRAS, that are a challenge to target using small molecule therapeutics. In addition, the screening methods of the disclosure were used to develop anti-infectivity agents that inhibit, e.g., viral infection such as infection by betaviruses (e.g., SARS-Cov2). As such, the screening methodology disclosed herein enables rapid discovery of potentially translatable peptide therapeutics and can be easily adaptable to diverse target genes and pathogenic contexts. These pathogenic contexts are not limited to cancer cell fitness. This methodology can be compatible with screening for higher level phenotypes via FACS, scRNAseq, as well as functional assays.

In a particular embodiment, the screening methodology described herein comprises providing a plurality of gene fragments which code for potentially inhibiting peptides for a targeted gene or genes (e.g., oncogenes, cell surface receptors, viral binding ligands etc.). The plurality of gene fragments may be generated by in silico pooled oligonucleotide synthesis technologies to generate large gene fragment libraries for use in the screening methods disclosed herein. Concepts from screening methodologies for CRISPR-based technologies can be used with the screening methodologies disclosed herein, including the CRISPR based screening methods found in Wang, T., Wei, J. J., Sabatini, D. M. & Lander, E. S., *Science* 343, 80-84 (2014); Gilbert, L. A. et al., *Cell* 159, 647-661 (2014); Shalem, O., Sanjana, N. E. & Zhang, F., *Nat Rev Genet* 16:299-311 (2015); Shalem, O. et al., *Science* 343, 84-87 (2014) each of which is hereby incorporated by reference in its entirety.

The disclosure provides synthesis of a gene fragment library using methods known to those of skill in the art. Gene fragments are then delivered to cells, using methods known to those in the art, including viral and non-viral methods. In a particular embodiment, the gene fragments are delivered to cells using lentiviral transduction. The disclosure provides that the cells may be cultured, such as under selective pressure and lysed and sequenced, such as deep-sequencing may be performed, to identify one or more nucleic acids from the library that are introduced into the cells using methods known to those of skill in the art, such as those described in Shalem, O., Sanjana, N. E. & Zhang, F., *Nat Rev Genet* 16:299-311 (2015); Shalem, O. et al., *Science* 343, 84-87 (2014); Agrotis, A. & Ketteler, R.,. *Front Genet* 6:300, each of which is hereby incorporated by reference in its entirety. Statistically-overrepresented nucleic acids may be determined using methods associated with pooled and arrayed screens (See Agrotis, A. & Ketteler, R. A new age in functional genomics using CRISPR/Cas9 in arrayed library screening. Front Genet 6, 300 (201S) hereby incorporated by reference in its entirety).

In a particular embodiment, a gene fragment library coding for potentially inhibitor peptides are synthesized via pooled oligonucleotide synthesis using solid-phase synthesis. Solid-phase synthesis is typically carried out on a solid support held between filters, in columns that enable all reagents and solvents to pass through freely. Solid-phase synthesis has a number of advantages over solution synthesis, including, large excesses of solution-phase reagents can be used to drive reactions quickly to completion; impurities and excess reagents are washed away and no purification may be required after each step; and the process is amenable to automation on computer-controlled solid-phase synthesizers. Solid supports (also called resins) are the insoluble particles, typically 50-200 μm in diameter, to which the oligonucleotide can be bound during synthesis. Many types of solid support have been used, but controlled pore glass (CPG) and polystyrene have proved to be the most useful.

The phosphoramidite method, pioneered by Marvin Caruthers in the early 1980s, and enhanced by the application of solid-phase technology and automation, is typically used. Phosphoramidite oligo synthesis proceeds in the 3'- to 5'-direction (opposite to the 5'- to 3'-direction of DNA biosynthesis in DNA replication). One nucleotide can be added per synthesis cycle. At the beginning of oligonucleotide synthesis, the first protected nucleoside can be pre-attached to the resin and the operator selects an A, G, C or T synthesis column depending on the nucleoside at the 3'-end of the desired oligonucleotide. The support-bound nucleoside has a 5'-DMT protecting group (DMT=4,4'-dimethoxytrityl), the role of which is to prevent polymerization during resin functionalization, and this protecting group must be removed (detritylation) from the support-bound nucleoside before oligonucleotide synthesis can proceed. Following detritylation, the support-bound nucleoside is ready to react with the next base, which can be added in the form of a nucleoside phosphoramidite monomer. A large excess of the appropriate nucleoside phosphoramidite can be mixed with an activator (tetrazole or a derivative), both of which are dissolved in acetonitrile (a good solvent for nucleophilic displacement reactions). The diisopropylamino group of the nucleoside phosphoramidite can be protonated by the activator, and can be thereby converted to a good leaving group. It can be rapidly displaced by attack of the 5'-hydroxyl group of the support-bound nucleoside on its neighboring phosphorus atom, and a new phosphorus-oxygen bond can be formed, creating a support-bound phosphite trimester. Nucleoside phosphoramidites are reasonably stable in an inert atmosphere and can be prepared in large quantities, shipped around the world and stored as dry solids for several months prior to use. Only upon protonation do nucleoside phosphoramidites become reactive.

It may not be unreasonable to expect a yield of 99.5% during each coupling step, but even with the most efficient chemistry and the purest reagents it may not be possible to achieve 100% reaction of the support-bound nucleoside with the incoming phosphoramidite. This means that there will be a few unreacted 5'-hydroxyl groups on the resin-bound nucleotide; if left unchecked, these 5'-hydroxyl groups would be available to partake in the next coupling step, reacting with the incoming phosphoramidite. The resulting oligonucleotide would lack one base. Deletion mutations are avoided by introducing a "capping" step after the coupling reaction, to block the unreacted 5'-hydroxyl groups. Two capping solutions are used on the synthesizer: acetic anhydride and N-methylimidazole (NMI). These two reagents (dissolved in tetrahydrofuran with the addition of a small quantity of pyridine) are mixed on the DNA synthesizer prior to delivery to the synthesis column. The electrophilic mixture rapidly acetylates alcohols, and the pyridine ensures that the pH remains basic to prevent detritylation of the nucleoside phosphoramidite by the acetic acid formed by reaction of acetic anhydride with NMI. Acetylation of the 5'-hydroxyl groups renders them inert to subsequent reactions.

After phosphoramidite coupling, capping and oxidation, the DMT protecting group at the 5'-end of the resin-bound DNA chain are removed so that the primary hydroxyl group can react with the next nucleotide phosphoramidite. Deprotection with trichloroacetic acid in dichloromethane can be rapid and quantitative. An orange color can be produced by cleaved DMT carbocation, which absorbs in the visible region at 495 nm. The intensity of this absorbance is used to determine the coupling efficiency. Most commercially available DNA synthesizers have hardware to measure and record the trityl yield for each cycle so that the efficiency of synthesis can be monitored in real time. The cycle can be repeated, once for each base, to produce the required oligonucleotide. The linker can be a chemical entity that attaches the 3'-end of the oligonucleotide to the solid support. It must be stable to all the reagents used in solid-phase oligonucleotide assembly, but cleavable under specific conditions at the end of the synthesis. The cleavage reaction can be carried out automatically on some synthesizers, and the ammoniacal solution containing the oligonucleotide can be delivered to a glass vial. Alternatively, the cleavage can be carried out manually by taking the column off the synthesizer and washing it with syringes containing ammonium hydroxide. The oligonucleotide, now dissolved in concentrated aqueous ammonia, can be heated to remove the protecting groups from the heterocyclic bases and phosphates. The aqueous solution can then removed by evaporation and the oligonucleotides are ready for purification.

Gene fragment libraries can be generated by splitting target gene(s) or relevant protein interaction partners into defined size fragments (e.g., 100 to 150 nt fragments). Several different commercial platforms exist for producing pooled oligonucleotides (e.g., CustomArray, Twist Bioscience, Agilent Technologies). Site directed mutagenesis can also be performed to optimize gene fragments for particular applications. Additionally, computational structure guided library design can be used to construct de novo gene fragment libraries which have predicted binding to target genes. The gene oligonucleotides are synthesized as gene fragment library which includes a plurality of gene fragments having more than 50, 100, 200, 300, 400, 500, 600, 700, 800, 1000, 1500, 2000, 5000, 10000 different sequences based from one or more target genes. Examples of target genes includes genes associated with a disease or disorder condition, such as oncogenes, or targets of infectious agents. The screening methodology of the disclosure can be agnostic to the disease model chosen. In theory, peptide inhibitors (drug-like peptides) of any protein target can be identified using the screening methods disclosed herein. The method can be assisted by having an in vitro assay to select for the phenotype of interest when contacted with a drug-like peptide. Alternatively, novel dominant negative inhibitors of protein function could be produced and sold as scientific reagents. Peptides across a wide size range (5-60 AA) can be screened via the screening methods disclosed herein, highlighting the broad utility of the screening methods of the disclosure as a platform technology.

In a particular embodiment, the gene fragments used in the screening methods disclosed herein are gene fragments of one or more oncogenes. Examples of oncogenes, include are but not limited to, MCL-1, BCR, BRAF, JAK1, JAK2, VEGF, EGFR, ALK, CDK1, CDK2, CDK3, CDK3, CDK4, BRCA, PIK3CA, MEK, C-KIT, NRAS, ABCB11, ANTXR2, BCOR, CDKN1B, CYP27A1, EMD, FANCF, ABCC8, APC, BCORL1, CDKN2A, CYP27B1, EP300, FANCG, ABCC9, AR, BLM, CEP290, DAXX, EPCAM, FANCI, ABCD1, ARID1A, BMPR1A, CFTR, DBT, EPHAS, FANCL, ABL1, ARID2, RAF1, CHEK1, DCC, EPHB2, FANCM, ACADM, ARSA, BRCA1, CHEK2, DCX, ERBB2, FAS, CADS, ASAH1, BRCA2, CHM, DDB2, ERBB3, FAT3, ACADVL, ASCC1, BRIP1, CIC, DDR2, ERBB4, FBXO11, ACTC1, ASL, BTD, CLN3, DES, ERCC2, FBXO32, ACTN2, ASPA, BTK, CLNS, DHCR7, ERCC3, FBXW7, ACVR1B, ASS1, BUB1B, CLN6, DICER1, ERCC4, FGD4, ADA, ASXL1, CALR3, CLN8, DIS3L2, ERCC5, FGFR1, ADAMTS13, ATM, CARD11, COL1A2, DKC1, ERCC6, FGFR2, ADAMTS2, ATP4A, CASP8, COL4A3, DLD, ERRFI1, FGFR3, AGA, ATP6V0D2, CAV3, COL4A4, DMD, ESCO2, FH, AGL, ATP7A, CBFB, COL7A1, DNAJB2, ESR1, FKTN, AGPS, ATP7B, CBL, COX15, DNMT3A, ETV6, FLCN, AHI1, ATP8B1, CBLB, CREBBP, DSC2, EXOC2, FLT3, AIP, ATR, CBLC, CRLF2, DSE, EXT1, FMR1, AKAP9, ATRX, CBS, CRTAP, DSC2, EXT2, FUBP1, AKT1, AXIN1, CCDC178, CRYAB, DSP, EYA4, FZD3, AKT2, AXIN2, CCNE1, CSF1R, DTNA, EZH2, G6PC, ALB, BAG3, CD79A, CSMD3, ECT2L, F11, GAA, ALDH3A2, BAI3, CD79B, CSRP3, EDA, F5, GABRA6, ALDOB, BAP1, CD96, CTNNB1, EDN3, FAH, GALNT12, ALK, BARD1, CDC27, CTNS, EDNRB, FAM46C, GALT, ALS2, BAX, CDC73, CTSK, EED, FANCA, GATA1, AMER1, BAZ2B, CDH1, CUBN, EGFR, FANCB, GATA2, AMPD1, BCKDHA, CDH23, CYLD, EGR2, FANCC, GATA3, AMPH, BCKDHB, CDK12, CYP11A1, EHBP1, FANCD2, GATAD1, ANTXR1, BCL6, CDK4, CYP21A2, ELMO1, FANCE, GBA, GCDH, JAK1, MDM2, NEK2, PLOD1, ROS1, SMPD1, GJB2, JAK2, MECP2, NEXN, PLP1, RPGRIP1L, SOX10, GLA, JAK3, MED12, NF1, PMP22, RS1, SOX2, GLB1, JUP, MEFV, NF2, PMS2, RSPO1, SPEG, GLI1, KAT6A, MEN1, NFE2L2, POLD1, RTEL1, SPOP, GLI3, KCNQ1, MET, NFKBIA, POLE, RUNX1, SRC, GLMN, KDM4B, MFSD8, NIPA2, POLH, RUNX1T1, SSTR1, GNA11, KDM6A, MIER3, NKX3-1, POMGNT1, RYR2, STAG2, GNAQ, KDR, MITF, NOTCH1, POMT1, S1PR2, STAR, GNAS, KEAP1, MKS1, NOTCH2, POU1F1, SAMD9L, STK11, GNPTAB, KIF1B, MLH1, NPC1, POU6F2, SBDS, SUFU, GPC3, KIT, MLH3, NPC2, PPM1L, SCN11A, SUZ12, GPC6, KLF6, MMAB, NPHP1, PPP2R1A, SCN5A, SYNE3, GPR78, KLHDC8B, MPL, NPHP4, PPT1, SCNN1A, TAZ, GRIN2A, KMT2A, MPZ, NPM1, PRDM1, SCNN1B, TBX20, GRM8, KMT2C, MRE11A, PRKAG2, SCNN1G, TCAP, GXYLT1, KMT2D, MSH2, NRCAM, PRKAR1A, SCO2, TCERG1, H3F3A, KRAS, MSH3, NTRK1, PRKDC, SDHA, TCF7L2, HADHA, KREMEN1, MSH6, NUP62, PROC, SDHAF2, TERT, HADHB, L1CAM, MSMB, OR5L1, PROP1, SDHB, TET2, HBB, LAMA2, MSR1, OTC, PRPF40B, SDHC, TFG, HESX1, LAMA4, MTAP, OTOP1, PRX, SDHD, TGFB3, HEXA, LAMP2, MTHFR, PAH, PSAP, SEPT9, TGFBR1, HEXB, LDB3, MTM1, PALB2, PSEN1, SETBP1, TGFBR2, HFE, LEPRE1, MTOR, PALLD, PSEN2, SETD2, THSD7B, HGSNAT, LIG4, MUC16, PAX5, PTCH1, SF1, TINF2, HIST1H3B, LMNA, MUT, PAX6, PTCH2, SF3A1, TMC6, HNF1A, LPAR2, MUTYH, PBRM1, PTEN, SF3B1, TMC8, HRAS, LRP1B, MYBPC3, PCDH15, PTGFR, SGCD, TMEM127, HSPH1, LRPPRC, MYC, PCGF2, PTPN11, SGSH, TMEM43, IDH1, LRRK2, MYD88, PDE11A, PTPN12, SH2B3, TMEM67, IDH2, LYST, MYH6, PDGFRA, RAC1, SLC25A4, TMPO, IGF2R, MAP2K1, MYH7, PDHA1, RAD21, SLC26A2, TNFAIP3, IGHMBP2, MAP2K2, MYL2, PDZRN3, RAD50, SLC37A4, TNFRSF14, IGSF10, MAP2K4, MYL3, PEX1, RAD51B, SLC7A8, TNNC1, IKBKAP, MAP3K1, MYLK2, PEX7, RAD51C, SLC9A9, TNNI3, IKZF1, MAP4K3, MYO1B, PHF6, RAD51D, SLX4, TNNT1, IKZF4, MAP7, MYO7A, PIK3CA, RARB, SMAD2, TNNT2, IL2RG, MAPK10, MYOZ2, PIK3CG, RB1, SMAD4, TP53, IL6ST, MAS1L, MYPN, PIK3R1, RBM20, SMARCA4, TPM1, IL7R, MAX, NBN, PKHD1, RECQL4, SMARCB1, TPP1, INVS, MC1R, NCOA2, PKP2, RET, SMC1A, TRAF5, IRAK4, MCCC2, NCOR1, PLEKHG5, RHBDF2, SMC3, TRIO, ITCH, MCOLN1, NDUFA13, PLN, RNASEL, SMO, TRPV4, TRRAP, U2AF1, USH1C, WAS, WWP1, ZIC3, TSC1, U2AF2, USH1G, WBSCR17, XPA, ZNF2, TSC2, UBA1, USP16, WEE1, XPC, ZNF226, TSHB, UBR3, USP25, WNK2, XRCC3, ZNF473, TSHR, UROD, VCL, WRN, ZBED4, ZNF595, TTN, UROS, VHL, WT1, ZFHX3, HER2, and ZRSR2. In a further embodiment, the oncogenes includes oncogenes selected from KRAS, HRAS, NRAS, RAF1, BRAF, ARAF, Myc, Max, FBXW7, and EGFR. In another embodiment, the gene fragments used in the screening methods disclosed herein are gene fragments of one or more receptors used as ligands for viruses. Examples of such receptor, include but are not limited to, CD4, poliovirus receptor, ICAM-1, Integrin (VLA-2), Coxsackievirus-adenovirus receptor (CAR), HAVcr-1, VACM-1, laminin receptor, angiotensin-converting enzyme 1 or 2 (ACE-1 or -2), MCP (CD46), SLAM, nectin-1, nectin-2, TNFR family, dipeptidyl peptidase-4 or -8 or -9, and CD21. The sequences of the oncogene/oncoproteins identified herein and above as well as the receptor identified herein have sequences that are known, as well as characterized biological activity. For example, AKT1 encodes RAC-alpha serine/threonine-protein kinase. This enzyme belongs to the AKT subfamily of serine/threonine kinases that contain SH2 (Src homology 2-like) domains. In some cases, it is commonly referred to as PKB, or by both names as "Akt/PKB". AKT1 was originally identified as the oncogene in the transforming retrovirus, AKT8. In some cases, "BRAF" is a human gene that encodes a protein called B-Raf. The gene can also be referred to as proto-oncogene B-Raf and v-Raf murine sarcoma viral oncogene homolog B, while the protein can be more formally known as serine/threonine-protein kinase B-Raf. In some cases, the B-Raf protein is involved in sending signals inside cells which are involved in directing cell growth. In some cases, the mammalian target of rapamycin (mTOR), sometimes also referred to as the mechanistic target of rapamycin and FK506-binding protein 12-rapamycin-associated protein 1 (FRAP1), is a kinase that in humans is encoded by the MTOR gene. mTOR is a member of the phosphatidylinositol 3-kinase-related kinase family of protein kinases. mTOR links with other proteins and serves as a core component of two distinct protein complexes, mTOR complex 1 and mTOR complex 2, which regulate different cellular processes. In particular, as a core component of both complexes, mTOR functions as a serine/threonine protein kinase that regulates cell growth, cell proliferation, cell motility, cell survival, protein synthesis, autophagy, and transcription. mTOR also functions as a tyrosine protein kinase that promotes the activation of insulin receptors and insulin-like growth factor 1 receptors. Over-activation of mTOR signaling significantly contributes to the initiation and development of tumors and mTOR activity was found to be deregulated in many types of cancer including breast, prostate, lung, melanoma, bladder, brain, and renal carcinomas. Various oncogenes and receptors coding sequence as well as the expressed polypeptides are described in Table 1.

Once synthesized, oligonucleotides are cloned into the appropriate vector for the biological model and planned screening study. In a particular embodiment, the gene fragments are packaged into viral vectors for delivery of gene fragments to target cells for overexpression. Viral vectors are introduced at a low multiplicity of infection (MOI) in order to ensure that cells receive only a single gene fragment from the library pool. Examples of viral vectors, include, but are not limited to, recombinant retroviral vectors, adenoviral vectors, adeno-associated viral vector, alphaviral vectors, and lentiviral vectors. In a particular embodiment, the viral vector is a lentiviral vector. Because lentiviruses integrate into the genome, the viral integrant serves as a tag for readout of which sgRNA construct can be delivered to a particular cell. Lentivirus is unique in its ability to infect non-dividing cells, and therefore has a wider range of potential applications. In some cases, the lentiviral genome in the form of RNA is reverse-transcribed when the virus enters the cell to produce DNA, which is then inserted into the genome at a position determined by the viral integrase enzyme. For safety reasons lentiviral vectors never carry the genes required for their replication.

In another embodiment, the viral vector is an adeno-associated virus (AAV). AAV is a tiny non-enveloped virus having a 25 nm capsid. In some cases, no disease is known or has been shown to be associated with the wild type virus. AAV has a single-stranded DNA (ssDNA) genome. AAV has been shown to exhibit long-term episomal transgene expression, and AAV has demonstrated excellent transgene expression in the brain, particularly in neurons. Vectors containing as little as 300 base pairs of AAV can be packaged and can integrate. Space for exogenous DNA can be limited to about 4.7 kb. An AAV vector such as that described in Tratschin et al., *Mol. Cell. Biol.* 5:3251-3260 (1985) can be used to introduce DNA into cells. A variety of nucleic acids have been introduced into different cell types using AAV vectors (see for example Hermonat et al., *Proc. Natl. Acad. Sci. USA* 81:6466-6470 (1984); Tratschin et al., *Mol. Cell. Biol.* 4:2072-2081 (1985); Wondisford et al., *Mol. Endocrinol.* 2:32-39 (1988); Tratschin et al., *J. Virol.* 51:611-.619 (1984); and Flotte et al., *J. Biol. Chem.* 268:3781-.3790 (1993). There are numerous alternative AAV variants (over 100 have been cloned), and AAV variants have been identified based on desirable characteristics. For example, AAV9 has been shown to efficiently cross the blood-brain barrier. Moreover, the AAV capsid can be genetically engineered to increase transduction efficient and selectivity, e.g., biotinylated AAV vectors, directed molecular evolution, self-complementary AAV genomes and so on. Modified AAV have also been described, including AAV based on ancestral sequences; see, e.g., U.S. Pat. No. 7,906,111; WO/2005/033321; WO2008/027084, WO2014/124282; WO2015/054653; and WO2007/127264. Other modified AAVs that have been described include chimeric nanoparticles (ChNPs) that have an AAV core that expresses a transgene that is surrounded by layer(s) of acid labile polymers that have embedded antisense oligonucleotides (e.g., see Hong et al., ACS Nano 10:8705-8716 (2016)) and Cho et al., *Biomaterials* 2012, 33, 3316-3323). The compositions and methods disclosed herein, in some embodiments, provide a platform technology, and as such the composition and methods disclosed herein can be used with all known AAVs, including the modified AAVs described in the literature, such as ChNPs.

Alternatively, retrovirus vectors and adeno-associated viral vectors can be used as a recombinant gene delivery system for the transfer of gene fragments. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for viral gene therapy, and defective retroviruses are characterized for use in gene transfer for viral gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al, eds., Current Protocols in Molecular Biology, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include Ψ& ιρ, Ψ&ε, Ψ2 and ΨΑΠι. Retroviruses have been used to introduce a variety of genes into many different cell types, including epithelial cells, in vitro and/or in vivo (see for example Eglitis, et al. (1985) *Science* 230: 1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254: 1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89: 10892-10895; Hwu et al. (1993) *J. Immunol.* 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the methods of the disclosure utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., *BioTechniques* 6:616 (1988); Rosenfeld et al., Science 252:431-434 (1991); and Rosenfeld et al., *Cell* 68: 143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle can be relatively stable and amenable to purification and concentration, and as above, can be modified so as to affect the spectrum of infectivity. Additionally, in some cases, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA can be large (up to 8 kilobases) relative to other gene delivery vectors (Berkner et al., supra; Haj-Ahmand and Graham, J. Virol. 57:267 (1986). Alphaviruses can also be used.

Alphaviruses are enveloped single stranded RNA viruses that have a broad host range, and when used in the methods disclosed herein alphaviruses can provide high-level transient gene fragment expression. Exemplary alphaviruses include the Semliki Forest virus (SFV), Sindbis virus (SIN) and Venezuelan Equine Encephalitis (VEE) virus, all of which have been genetically engineered to provide efficient replication-deficient and -competent expression vectors. Alphaviruses exhibit significant neurotropism, and so are useful for CNS-related diseases. See, e.g., Lundstrom, Viruses. 2009 June; 1(1): 13-25; Lundstrom, Viruses. 2014 June; 6(6): 2392-2415; Lundstrom, *Curr Gene Ther.* 2001 May; 1(1): 19-29; Rayner et al., Rev Med Virol. 2002 September-October; 12(5):279-96.

Gamma-retroviral vectors (replication competent or defective) can also be used (e.g., MLV). Typical constructs include viruses with a viral genome comprising viral genes (e.g., gag, pol, env) having an expression cassette located in the LTRs or downstream of the envelope gene.

The frequency of observing any particular tag (gene fragment) before and after phenotypic selection can be a parameter measured using the screening methods disclosed herein. After cloning, the distribution of cloned oligos in the pooled library can be assessed using Next-Generation Sequencing (NGS). In some cases, high throughput sequencing is then used to track the abundance of each gene fragment as the target cells grow. Gene fragments which significantly deplete over the course of cell growth are deleterious to cell fitness and can then be synthesized individually to measure their performance in additional assays, such as cell proliferation, RNA-Seq, Mass Spec, etc.

As exemplified in the studies presented herein, the screening methodology of the disclosure allowed for the identification of highly effective dominant negative inhibitors of oncogene mediated cancer cell proliferation and viral entry. Because the library of gene fragments can be user defined and custom synthesized, the screening methods disclosed herein are easily adaptable to diverse projects where a selection strategy can be devised to enrich or deplete cells with the phenotype of interest. Technologies which can partition cells based on unique phenotypic features such as Flow Activated Cell Sorting (FACS), or magnetic bead pull down will play a key role in expanding this methodology beyond proliferation. This combined with the decreasing cost of single cell RNA sequencing allows for investigation of increasingly more complex phenotypes, such as cellular differentiation and regeneration. Dominant negative peptides have immense potential as both research tools and therapeutics. Direct inhibition of protein activity without genetic alteration opens unique screening avenues with which to probe protein function. For example, one of the dominant negative fragments identified in the studies presented herein appears selective to a specific KRAS mutation, potentially allowing for mutant allele specific inhibition in a functional screen. Furthermore, with minimal engineering, a dominant negative peptide EGFR inhibitor opposed TNBC cell growth in vitro as effectively as FDA approved small molecules. Because one of the key limitations of dominant negative peptide inhibitors can be the intracellular location of the target proteins, it is expected that advances in biologics delivery can improve the translational relevance this strategy.

In concert with direct oncological applications, the screening methodologies disclosed herein could be potentially used to identify peptides which are immunostimulatory/immunosuppressive via FACS based screening of immune effector cells. The design of the experiment could be tailored specifically to the pathogenic context (e.g., screening in regulatory T cells to identify immunosuppressive peptides to treat autoimmune disorders). Furthermore, the screening methodologies disclosed herein could also be adapted to inhibiting pathogenic protein-protein interactions directly, such as neurodegenerative tauopathies.

As such, the disclosure further provides the following applications which can utilize the screening methodologies described herein, including, but not limited to, profiling MHC binding peptides; disrupting pathogenic protein aggregation relevant to tauopathies, amyloid plaques etc.; cytokine/receptor engineering or profiling relevant to cancer immunotherapy as well as autoimmune disorders; identifying peptides mediating regenerative phenotypes such as angiogenesis; discovering anti-aging therapeutics; and discovering pain modulating peptides.

The disclosure provides a number of drug-like peptides in the accompanying sequence listing (incorporated herein by reference) that can have biological activity in various cancer and disease models. The disclosure thus provides peptides comprising, consisting essentially of or consisting of sequences that are at least 85, 87, 90, 92, 94, 95, 98, 99 or 100% identical to any one of the sequences set forth in the accompanying sequence listing at SEQ ID NOs:1-9488 or 9489). Moreover, it should be recognized that the peptides of the disclosure can have 1-30 additional amino acids appended to the N- or C-terminal end of the peptide (e.g., CPPs, linkers, purification sequences etc.). These drug-like peptide can be delivered to a subject or cell to treat cancer or disease progression by inhibiting the biological activity of the corresponding full length polypeptide from which the peptides are derived. For example, two drug-like peptides (RAF1_73 and EGFR_697) are exemplified that opposed triple-negative breast cancer cell growth in vitro as effectively as some FDA approved small molecules. Because peptide drugs are often limited by the intracellular location of the target proteins, advances in biologics delivery will drastically improve the translational relevance of this strategy.

The disclosure provides drug-like peptides (e.g., dominant negative peptides) as set forth in Table 1. The dominant negative peptides can be used to treat cell proliferative disorders (e.g., such as those in the same row as the peptide sequence) where the cell proliferative disorder can be caused by or associated with the biological activity of the gene product.

TABLE 1

| Parental Gene/Protein Name | Exemplary Disease/Disorder/Cancer | Parental (SEQ ID NO) * | Drug-like peptides (SEQ ID NOs) |
|---|---|---|---|
| AKT1 (synonyms: PKB-ALPHA, RAC, PRKBA, PKB, RAC-ALPHA, CWS 6) | ductal carcinoma, lung adenocarcinoma, colon adenocarcinoma, endometrial endometrioid adenocarcinoma, and invasive breast carcinoma | 9540 | 1-5, 5000-5010 |
| AR (androgen receptor; synonyms: KD, NR3C4, DHTR, AR8, HYSP1, TFM, AIS, SMAX1, SBMA, HUMARA) | prostate adenocarcinoma, lung adenocarcinoma, colon adenocarcinoma, endometrial endometrioid adenocarcinoma, and breast invasive ductal carcinoma | 9542 | 3499, 3750-3759, 5011-5073 |
| ARAF (synonyms: RAFA1, A-RAF, ARAF1, PKS2) | lung adenocarcinoma, colon adenocarcinoma, endometrial endometrioid adenocarcinoma, breast invasive | 9544 | 5074-5084 |

TABLE 1-continued

| Parental Gene/Protein Name | Exemplary Disease/Disorder/Cancer | Parental (SEQ ID NO) * | Drug-like peptides (SEQ ID NOs) |
|---|---|---|---|
| | ductal carcinoma, and high grade ovarian serous adenocarcinoma | | |
| BRAF (synonyms: RAFB1, BRAF1, NS7, B-raf, B-RAF1) | colon adenocarcinoma, cutaneous melanoma, lung adenocarcinoma, melanoma, and thyroid gland papillary carcinoma, colorectal adenocarcinoma, breast invasive ductal carcinoma, melanoma, prostate adenocarcinoma | 9546 | 6-15, 350-489, 2555-2586, 2949-2974, 3500-3509, 3760-3792, 5086-5185 |
| CASP8 | Breast and ovarian cancer | 9548 | 490-498, 2587-2588, 2975-2981, 3511, 3793-3804, 5186-5228 |
| CCND1 (synonyms: BCL1, D11S287E, U21B31, PRAD1) | breast invasive ductal carcinoma, invasive breast carcinoma, bladder urothelial carcinoma, breast invasive lobular carcinoma, and lung adenocarcinoma | 9550 | 5229-5250 |
| CDH1 (cadherin-1; synonyms: CAM120/80, E-cadherin, uvomorulin) | lobular breast carcinoma | 9552 | 499-514, 2589-2591, 2982, 3511, 3805-3816, 5251-5310 |
| CDKN2A (cyclin-dependent kinase inhibitor 2A; synonyms: MLM, P19, CDK4I, MTS1, P19ARF, CDKN2, P16, CMM2, P14, TP16, P16INK4A, P16INK4, ARF, MTS-1, INK4, INK4A, P16-INK4A, P14ARF) | lung adenocarcinoma, conventional glioblastoma multiforme, pancreatic adenocarcinoma, cutaneous melanoma, and bladder urothelial carcinoma | 9554 | 515-517 |
| CHEK2 (checkpoint kinase 2; synonyms: CDS1, CHK2, LFS2, RAD53, hCds1, HuCds1, PP1425) | Breast cancer, ovarian cancer, colorectal cancer, prostate cancer, thyroid cancer, osteosarcoma | 9556 | 518-592, 2592-2609, 2983-3009, 3443-3444, 3512-3514, 3817-3859, 5311-5450 |
| CTNNB1 (catenin beta-1; synonyms: armadillo, EVR7, CTNNB, MRD19) | lung adenocarcinoma, endometrial endometrioid adenocarcinoma, colon adenocarcinoma, hepatocellular carcinoma, and prostate adenocarcinoma | 9558 | 16-27, 593-636, 2610-2629, 3010-3039, 3860-3862, 5451-5502 |
| DDX3X (DEAD-box helicase 3 X-linked; synonyms: DBX, DDX3, HLP2, DDX14, CAP-Rf, MRX102) | Liver cancer, medulloblastoma | 9560 | 637-645, 2630-2634, 3040-3042, 3863-3878, 5503-5582 |
| DICER1 (synonyms: DCR1, GLOW, MNG1, Dicer, HERNA, RMSE2, Dicerle, K12H4.8-LIKE) | Ovarian cancer, lung cancer, testicular cancer, thyroid cancer, Wilms tumour, stomach cancer, bladder cancer, skin cancer, lung cancer, eye cancer | 9562 | 28-32, 646-671, 2635-2639, 3043-3059, 3445-3447, 3515-3532, 3879-3941, 5583-5863 |
| EGFR (epithelial growth factor receptor; synonyms: ERBB, HER1, mENA, NISBD2, PIG61, ERBB1) | lung adenocarcinoma, conventional glioblastoma multiforme, breast invasive ductal carcinoma, glioblastoma, and colon adenocarcinoma | 9564 | 33-49, 672-725, 2640-2655, 3060-3082, 3448, 3533-3536, 3942-3973, 5864-5934 |
| EP300 (histone acetyltransferase p300; synonyms: KAT3B, RSTS2, p300) | lung adenocarcinoma, colon adenocarcinoma, bladder urothelial carcinoma, breast invasive ductal carcinoma, and endometrial endometrioid adenocarcinoma | 9566 | 50-59, 726-736, 2656-2660, 3083-3105 |
| ERBB2 (receptor tyrosine-protein kinase erbB-2; synonyms: HER-2, CD340, NEU, “MLN 19”, NGL, TKR1, HER-2/neu, HER2) | breast invasive ductal carcinoma, lung adenocarcinoma, colon adenocarcinoma, bladder urothelial carcinoma, and invasive breast carcinoma | 9568 | 60, 737-742, 2661-2662, 3106-3107, 3537-3538, 3974-3985, 5935-5980 |
| ERBB3 (receptor tyrosine-protein kinase erbB-3; synonyms: erbB3-S, LCCS2, p85-sErbB3, c-erbB3, HER3, MDA-BF-1, p180-ErbB3, ErbB-3, c-erbB-3, p45-sErbB3) | colon adenocarcinoma, breast invasive ductal carcinoma, bladder urothelial carcinoma, lung adenocarcinoma, and endometrial endometrioid adenocarcinoma | 9570 | 743-745, 3539-3544, 3986-3998, 5981-6064 |
| ERBB4 (ERBB4 intracellular domain; synonyms: p180erbB4, ALS19, HER4) | lung adenocarcinoma, colon adenocarcinoma, cutaneous melanoma, melanoma, and breast invasive ductal carcinoma | 9572 | 746-751, 2663, 3108-3110, 3449-3451, 3545-3548, 3999-4047, 6065-6180 |

TABLE 1-continued

| Parental Gene/Protein Name | Exemplary Disease/Disorder/Cancer | Parental (SEQ ID NO) * | Drug-like peptides (SEQ ID NOs) |
|---|---|---|---|
| FBXW7 (F-box/WD repeat-containing protein 7; synonyms: SEL-10, FEW6, hAgo, CDC4, FBX30, FBW7, FBXO30, hCdc4, SEL10, FBXW6, AGO) | colon adenocarcinoma, rectal adenocarcinoma, lung adenocarcinoma, colorectal adenocarcinoma, and endometrial endometrioid adenocarcinoma | 9574 | 752-812, 2664-2668, 3111-3125, 3549, 4048-4061, 6181-6251 |
| FGFR2 (fibroblast growth factor receptor 2; synonyms: BEK, CFD1, TK25, KGFR, BBDS, TK14, BFR-1, JWS, CEK3, K-SAM, ECT1, CD332) | endometrial endometrioid adenocarcinoma, breast invasive ductal carcinoma, colon adenocarcinoma, lung adenocarcinoma, and cutaneous melanoma | 9576 | 813-819, 2669-2671, 3126-3130, 4062-4075, 6252-6310 |
| FGFR3 (fibroblast growth factor receptor 3; synonyms: CD333, HSFGFR3EX, JTK4, CEK2, ACH) | bladder urothelial carcinoma, colon adenocarcinoma, lung adenocarcinoma, breast invasive ductal carcinoma, and infiltrating renal pelvis and ureter urothelial carcinoma | 9578 | 820-824, 6311-6323 |
| FLT3 (receptor-type tyrosine-protein kinase FLT3; synonyms: FLK-2, FLK2, CD135, STK1) | colon adenocarcinoma, acute myeloid leukemia, lung adenocarcinoma, breast invasive ductal carcinoma, and cutaneous melanoma | 9580 | 825-855, 2672-2678, 3131, 3550-3572, 4076-4106, 6324-6471 |
| GFP | | 9582 | 856-858 |
| GNA11 (guanine nucleotide-bindign protein subunit alpha-11; synonyms: FBH, GNA-11, FBH2, HYPOC2, HHC2, FHH2) | uveal melanoma, colon adenocarcinoma, lung adenocarcinoma, breast invasive ductal carcinoma, and high grade ovarian serous adenocarcinoma | 9584 | 859-863, 3132, 4107, 6472-6481 |
| GNAQ (guanine nucleotide-bindign protein G (q) subunit alpha; synonyms: GAQ, G-ALPHA-q, CMC1, SWS) | uveal melanoma, lung adenocarcinoma, colon adenocarcinoma, melanoma, and bladder urothelial carcinoma | 9586 | 61-63, 864-866, 2679-2682, 3133-3136, 6482-6510, |
| HPRT1 (hypoxanthine-guanine phosphoribosyltransferase; synonyms: HPRT, HGPRT) | Skin cancer, bladder cancer, cervical cancer, Wilms Tumour | 9588 | 64-65, 867-875, 2683, 3137-3146, 4108, 6511-6525, |
| HRAS (GTPase HRas, N-terminally processed; synonyms: HRAS1, C-H-RAS, C-BAS/HAS, H-RASIDX, CTLO, RASH1, p21ras, HAMSV, C-HA-RAS1) | bladder urothelial carcinoma, myelodysplastic syndromes, breast invasive ductal carcinoma, acute myeloid leukemia, and lung adenocarcinoma | 9590 | 876-894, 2684, 3147-3149, 6526-6527, |
| IDH1 (isocitrate dehydrogenase (NADP) cytoplasmic; synonyms: IDP, IDCD, HEL-216, IDE, HEL-S-26, PICD, IDPC) | oligodendroglioma, anaplastic astrocytoma, astrocytoma, acute myeloid leukemia, and conventional glioblastoma multiforme | 9592 | 895-905, 3150-3152, 4109, 6528-6557 |
| IDH2 (isocitrate dehydrogenase (NADP), mitochondrial; synonyms: IDP, IDEM, IDE, ICD-M, mNADP-IDH, IDPM, D2HGA2) | acute myeloid leukemia, breast invasive ductal carcinoma, colon adenocarcinoma, lung adenocarcinoma, and myelodysplastic syndromes | 9594 | 66-69, 899-905, 4110-4111, 6558-6571 |
| KEAP1 (Kelch-like ECH-associated protein 1; synonyms: INrf2, KLHL19) | lung adenocarcinoma, squamous cell lung carcinoma, non-small cell lung carcinoma, cancer of unknown primary, and colon adenocarcinoma | 9596 | 906-921, 2685, 3153-3156, 4112, 6572-6582 |
| KIT (mast/stem cell growth factor receptor Kit; synonyms: SCFR, C-Kit, MASTC, PBT, CD117) | gastrointestinal stromal tumor, lung adenocarcinoma, colon adenocarcinoma, conventional glioblastoma multiforme, and melanoma | 9598 | 70-73, 922-950, 2686-2703, 3157-3184, 3573-3574, 4113-4127, 6583-6707 |
| KMT2C (histone-lysine N-methyltransferase 2C; synonyms: HALR, KLEFS2, MLL3) | breast invasive ductal carcinoma, lung adenocarcinoma, colon adenocarcinoma, prostate adenocarcinoma, and cutaneous melanoma | 9600 | 951-961, 3185 |
| KRAS (MAP kinase signaling) | lung adenocarcinoma, colon adenocarcinoma, pancreatic adenocarcinoma, colorectal adenocarcinoma, and rectal adenocarcinoma | 9602 | 962-1052, 2704-2721, 3186-3198, 3452, 3575-3579, 4128-4158, 6708-6753 |

TABLE 1-continued

| Parental Gene/Protein Name | Exemplary Disease/Disorder/Cancer | Parental (SEQ ID NO) * | Drug-like peptides (SEQ ID NOs) |
|---|---|---|---|
| KRAS4B (MAP kinase signaling 4B) | lung adenocarcinoma, colon adenocarcinoma, pancreatic adenocarcinoma, colorectal adenocarcinoma, and rectal adenocarcinoma | 9604 | 4159-4167, 6754-6805 |
| MAP2K1 (dual specificity mitgen-activated protein kinase kinase 1; synonyms: MAPKK1, PRKMK1, CFC3, MEK1, MKK1) | cutaneous melanoma, colon adenocarcinoma, lung adenocarcinoma, bladder urothelial carcinoma, and breast invasive ductal carcinoma | 9606 | 74, 1053-1059, 2722, 3199-3202, 3580, 4168-4180, 6806-6848 |
| MAX (MYC associated factor X) | Colorectal cancer, breast cancer, prostate cancer, lung cancer, liver cancer | 9608 | 6849-6851 |
| MDM2 (E3 ubiquitin-protien ligase Mdm2; synonyms: HDMX, ACTFS, hdm2) | lung adenocarcinoma, breast invasive ductal carcinoma, dedifferentiated liposarcoma, bladder urothelial carcinoma, and conventional glioblastoma multiforme | 9610 | 3453-3455, 3581-3588, 4181-4221, 6852-6939 |
| MDM4 (synonyms: HDMX, MRP1, MDMX) | breast invasive ductal carcinoma, lung adenocarcinoma, conventional glioblastoma multiforme, glioblastoma, and prostate adenocarcinoma | 9612 | 3589-3595, 4222-4262, 6940-7052 |
| MET (hepatocyte growth factor receptor; synonyms: c-Met, DFNB97, RCCP2, HGFR, AUTS9) | lung adenocarcinoma, colon adenocarcinoma, cutaneous melanoma, melanoma, and conventional glioblastoma multiforme | 9614 | 75, 1060-1071, 2723-2729, 3203-3216, 3456-3457, 3596-3600, 4263-4297, 7053-7273 |
| MTOR (serine/threonine-protein kinase mTOR; synonyms: RAPT1, FRAP2, FRAP, FRAP1, RAFT1, SKS) | lung adenocarcinoma, colon adenocarcinoma, endometrial endometrioid adenocarcinoma, breast invasive ductal carcinoma, and bladder urothelial carcinoma | 9616 | 76-77, 1072-1080, 3458, 3601, 4298-4311, 7274-7379 |
| MYC (Myc prot-oncogene protein; synonyms: MRTL, MYCC, bHLHe39, c-Myc) | breast invasive ductal carcinoma, lung adenocarcinoma, prostate adenocarcinoma, colon adenocarcinoma, and high grade ovarian serous adenocarcinoma | 9618 | 4312-4317, 7380-7409 |
| MYCL (synonyms: bHLHe38, LMYC, L-Myc, MYCL1) | bladder urothelial carcinoma, breast invasive ductal carcinoma, high grade ovarian serous adenocarcinoma, small cell lung carcinoma, and lung adenocarcinoma | 9620 | 4318, 7410-7426 |
| MYCN (N-myc proto-oncogene protein; synonyms: N-myc, ODED, MODED, bHLHe37, NMYC) | neuroblastoma, conventional glioblastoma multiforme, breast invasive ductal carcinoma, bladder urothelial carcinoma, and anaplastic astrocytoma | 9622 | 3602, 4319-4327, 7427-7453 |
| NCOA3 (nuclear receptor coactivator 3) | breast invasive ductal carcinoma, colon adenocarcinoma, rectal adenocarcinoma, lung adenocarcinoma, and mixed lobular and ductal breast carcinoma | 9624 | 3603, 4328-4378, 7454-7618 |
| NFE2L2 (nuclear factor erythroid 2-related factor 2; synonyms: HEBP1, NRF2, IMDDHH) | squamous cell lung carcinoma, lung adenocarcinoma, endometrial endometrioid adenocarcinoma, bladder urothelial carcinoma, and colon adenocarcinoma | 9626 | 1081-1183, 2730-2740, 3217-3221, 3459-3460, 3604-3634, 4379-4430, 7619-7694 |
| NKX2 | Lung cancer, adenocarcinomas, thyroid cancer | 9628 | 4431-4435, 7695-7712 |
| NOTCH1 (synonyms: AOVD1, TAN1, AOS5, hN1) | colon adenocarcinoma, lung adenocarcinoma, breast invasive ductal carcinoma, endometrial endometrioid adenocarcinoma, and bladder urothelial carcinoma | 9630 | 1184-1187, 4436, 7713-7752 |
| NRAS (GTPase NRas; synonyms: ALPS4, NRAS1, NS6, CMNS, NCMS, N-ras) | cutaneous melanoma, melanoma, colon adenocarcinoma, acute myeloid leukemia, and lung adenocarcinoma | 9632 | 1188-1197, 2741-2747, 3222-3225, 4437-4444, 7753-7771 |
| OMOMYC (dominant negative of Myc) | breast invasive ductal carcinoma, lung adenocarcinoma, prostate adenocarcinoma, colon adenocarcinoma, and high grade ovarian serous adenocarcinoma | 9634 | 4445-4447, 7772-7782 |

TABLE 1-continued

| Parental Gene/Protein Name | Exemplary Disease/Disorder/Cancer | Parental (SEQ ID NO) * | Drug-like peptides (SEQ ID NOs) |
|---|---|---|---|
| PIK3CA (Phosphatidylinositol 4,5-bisphosphate 3-kinase catalytic subunit alpha isoform; Synonyms: PI3K, MCM, p110-alpha, MCAP, CLOVE, MCMTC, PI3K-alpha, CWS5) | breast invasive ductal carcinoma, colon adenocarcinoma, lung adenocarcinoma, endometrial endometrioid adenocarcinoma, and breast invasive lobular carcinoma | 9636 | 78-111, 1198-1273, 2748-2788, 3226-3254, 3461-3463, 3635-3650, 4448-4565, 7783-8035 |
| PIK3R1 (phosphatidylinositol 3-kinase regulatory subunit alpha; synonyms: IMD36, AGM7, GRB1, p85-ALPHA, p85) | endometrial endometrioid adenocarcinoma, colon adenocarcinoma, breast invasive ductal carcinoma, conventional glioblastoma multiforme, and lung adenocarcinoma | 9638 | 112-151, 1274-1308, 2789-2825, 3255-3279, 3651-3655, 4566-4608, 8036-8180 |
| PPP2R1A (Serine/threonine-protein phosphatase 2A 65 kDa regulatory subunit A alpha isoform; synonyms: MRD36, PP2A-Aalpha, PP2AA, PP2AAALPHA, PR65A) | endometrial serous adenocarcinoma, breast invasive ductal carcinoma, colon adenocarcinoma, lung adenocarcinoma, and endometrial endometrioid adenocarcinoma | 9640 | 152-153, 1309-1329, 2826, 3280-3287, 3656, 8181-8201 |
| PTPN11 (Tyrosine-protein phosphatase non-receptor type 11; synonyms: SH-PTP3, JMML, SHP2, PTP-1D, BPTP3, CFC, NS1, SH-PTP2, PTP2C, METCDS) | acute myeloid leukemia, lung adenocarcinoma, conventional glioblastoma multiforme, colon adenocarcinoma, and glioblastoma | 9642 | 154-171, 1330-1385, 2827-2840, 3288-3301, 3464, 3657, 4609-4626, 8202-8310 |
| RAB25 (Ras-related protein 25) | Breast cancer, colorectal adenocarcinoma and esophageal cancer | 9644 | 4627, 8311-8313 |
| RAC1 (Ras-related C3 botulinum toxin substrate 1) | Melanoma and non-small cell lung cancer | 9646 | 172, 1386-1412, 2841-2845, 3302-3313, 3658-3661, 4628-4640, 8314-8339 |
| RAF1 (RAF proto-oncogene serine/threonine-protein kinase; synonyms: Raf-1, C-Raf, NS5, CMD1NN, CRAF) | colon adenocarcinoma, bladder urothelial carcinoma, lung adenocarcinoma, cutaneous melanoma, and breast invasive ductal carcinoma | 9648 | 3465-3467, 4641-4654, 8340-8403 |
| RASA1 (RAS p21 protein activator 1) | Basal cell carcnoma | 9650 | 1413-1417, 3314, 3468-3491, 3662-3674, 4655-4738, 8404-8620 |
| RB1 (retinoblastoma-associated protein; synonyms: PPP1R130, pRb, OSRC, RB, p105-Rb, pp110) | lung adenocarcinoma, breast invasive ductal carcinoma, small cell lung carcinoma, bladder urothelial carcinoma, and colon adenocarcinoma | 9652 | 1418-1424, 2846-2856, 3315-3321, 3492-3494, 3675-3713, 4739-4823, 8621-8861 |
| RHEB (GTP-bindign protein Rheb; RHEB2) | lung adenocarcinoma, colon adenocarcinoma, breast invasive ductal carcinoma, prostate adenocarcinoma, and endometrial endometrioid adenocarcinoma | 9654 | 1425-1432, 2857-2858, 3322-3329, 4824-4829, 8862-8901 |
| RHOA (Ras homolog family member A; synonyms: ARHA, ARH12, RHO12, RHOH12) | Breast cancer, lung cancer, liver cancer, ovarian cancer, bladder cancer | 9656 | 173-175, 1433-1508, 2859-2872, 3330-3384, 4830-4833, 8902-8924 |
| RRAS2 (related RAS viral oncogene homolog 2) | Oral cancer, esophageal cancer, stomach cancer, skin cancer, breast cancer, lymphomas | 9658 | 1509-1514, 3495, 3714-3725, 4834-4845, 8925-8949 |
| RUNX1 (runt-related transcription factor 1; synonyms: AML1-EVI-1, CBFA2, CBF2alpha, PEBP2alpha, AML1, AMLCR1, PEBP2aB, EVI-1) | breast invasive ductal carcinoma, acute myeloid leukemia, myelodysplastic syndromes, lung adenocarcinoma, and breast invasive lobular carcinoma | 9660 | 1515-1518, 2873, 4846-4850, 8950-8966 |
| SETD2 (histone-lysine N-methyltransferase SETD2; synonyms: LLS, HIP-1, HIF-1, HYPB, p231HBP, KMT3A, HSPC069, SET2, HBP231) | lung adenocarcinoma, clear cell renal cell carcinoma, colon adenocarcinoma, breast invasive ductal carcinoma, and endometrial endometrioid adenocarcinoma | 9662 | 176-179, 1519-1532, 2874-2878, 3385-3393 |
| SF3B1 (splicing factor 3B subunit 1; synonyms: SF3b155, PRP10, Hsh155, SAP155, PRPF10, MDS) | breast invasive ductal carcinoma, lung adenocarcinoma, colon adenocarcinoma, myelodysplastic syndromes, and bladder urothelial carcinoma | 9664 | 180-204, 1533-1589, 2879-2891, 3394-3410, 3496-3498, 3726-3731, 4851-4922, 8967-9148 |

TABLE 1-continued

| Parental Gene/Protein Name | Exemplary Disease/Disorder/Cancer | Parental (SEQ ID NO) * | Drug-like peptides (SEQ ID NOs) |
|---|---|---|---|
| SKP2 (S-phase kinase associate d protein 2; synonyms: p45, FBL1, FLB1, FBXL1) | Breast cancer, lung cancer, prostate cancer, liver cancer, Ewing's Sarcoma, skin cancer | 9666 | 4923-4931, 9149-9182 |
| SMAD2 (SMAD family member 2; synonyms: JV18, MADH2, MADR2, JV18-1, hMAD-2, hSMAD2) | Colorectal cancer, breast cancer, lung cancer, pancreatic cancer, uterine sarcoma, bladder cancer, eye cancer | 9668 | 1590-1591, 2892, 3732-3733, 4932-4937, 9183-9228 |
| SMAD4 (SMAD family member 4; synonyms: JIP, DPC4, MADH4, MYHRS) | Pancreatic cancer, colorectal cancer, breast cancer, stomach cancer, lung cancer, liver cancer, adenomatous polyposis coli, cervical cancer | 9670 | 205-207, 1592-1795, 2893-2911, 3411-3426, 3734-3745, 4938-4959, 9229-9288 |
| SPOP (Speckle-type BTB/POZ; synonyms: BTBD32, TEF2, speckle type BTB/POZ protein, NEDMIDF, NSDVS1, NSDVS2, NEDMACE) | prostate, lung, colon, gastric, kidney and liver cancers | 9672 | 208, 1796-1804, 2912-2913, 3427 |
| TERT (telomerase reverse transcriptase; synonyms: PFBMFT1, TCS1, hTRT, hEST2, CMM9, DKCB4, DKCA2, EST2, TRT, TP2) | lung adenocarcinoma, colon adenocarcinoma, breast invasive ductal carcinoma, cutaneous melanoma, and conventional glioblastoma multiforme | 9674 | 4960-4976, 9289-9390 |
| TGFBR2 | colon adenocarcinoma, lung adenocarcinoma, pancreatic adenocarcinoma, cutaneous melanoma, and breast invasive ductal carcinoma | 9676 | 1805, 3746-3749, 4977-4988, 9391-9417 |
| TP53 (cellular tumor antigen p53; synonyms: BCC7, TRP53, P53, LFS1) | lung adenocarcinoma, breast invasive ductal carcinoma, colon adenocarcinoma, pancreatic adenocarcinoma, and colorectal adenocarcinoma | 9678 | 209-341, 1806-2482, 2914-2943, 3428-3439, 4989-4990, 9418-9432 |
| VHL (von Hippel-Lindau disease tumor suppressor; synonyms: RCA1, VHL1, HRCA1, pVHL) | clear cell renal cell carcinoma, renal cell carcinoma, lung adenocarcinoma, breast invasive ductal carcinoma, and bladder urothelial carcinoma | 9680 | 342-349, 2483-2553, 2944-2948, 3440-3442, 4991-4997, 9433-9440 |
| YAP1 (transcription coactivator YAP1; synonyms: YAP, YAP2, YAP65, COB1, YKI) | breast invasive ductal carcinoma, lung adenocarcinoma, bladder urothelial carcinoma, cutaneous melanoma, and head and neck squamous cell carcinoma | 9682 | 4998-4999, 9441-9459 |
| ZFP36L2 (zinc finger protein 36 ring finger protein-like 2) | Colorectal cancer, ovarian cancer, endometrial cancer, skin cancer, testicular cancer, urothelial cancer, pancreatic cancer and liver cancer | 9684 | 2554 |
| ACE2 (angiotensin-converting enzyme 2) | serves as the entry point for some coronaviruses, including HCoV-NL63, SARS-CoV, and SARS-CoV-2 | 9686 | 9460-9470 |
| ACE1 (angiotensin-converting enzyme 1) | serves as the entry point for some coronaviruses, including HCoV-NL63, SARS-CoV, and SARS-CoV-2 | 9688 | 9471-9472, 9489 |
| DPP9 (dipeptidyl peptidase 9) | serves as the entry point for some coronaviruses | 9690 | 9473-9474, 9488 |
| ANPEP (alanine aminopeptidase N) | serves as the entry point for some coronaviruses | 9692 | 9475-9476, 9486 |
| FAP (prolyl endopeptidase FAP) | serves as the entry point for some coronaviruses | 9694 | 9477-9478, 9485 |
| DPP4 (dipeptidyl peptidase 4) | serves as the entry point for some coronaviruses | 9696 | 9479-9480, 9483 |
| Fibronectin | serves as the entry point for some coronaviruses | 9698 | 9481-9482, 9484 |
| DPP8 (dipeptidyl peptidase 8) | serves as the entry point for some coronaviruses | 9700 | 9487 |

* Mutants are also contemplated. As used herein, e.g., "289T" refers to a mutation at position 289, wherein position 289 can be T. Similarly, "782R/V" refers to a mutation at position 782, wherein position 782 can be R or V.

The disclosure provides, in one embodiment, a comprehensive screening platform which enables the identification of peptide inhibitors of pathological processes. This methodology can be scalable due to the ease of oligonucleotide synthesis, simple to perform, and highly precise, allowing users to interrogate proteins with single amino acid resolution. Because the library of peptide coding gene fragments can be user defined and custom synthesized, this strategy can be easily adaptable to diverse studies where a selection strategy can be devised to enrich or deplete cells with the phenotype of interest. Inhibitory peptides have immense potential as both research tools and therapeutics. Direct inhibition of protein activity without genetic alteration opens unique screening avenues with which to probe protein function. For example, protein-protein interaction networks could be more precisely perturbed via inhibitory peptides contacting a specific protein surface than by complete genetic knockdown. The ability to identify protein regions associated with cell fitness can also serve to complement traditional drug development efforts, such as determining critical residues for inhibition via small molecules or antibodies. Additionally, this screening resource identifies inhibitory peptides that are immediately translatable, bypassing the need for additional high-throughput screens to identify candidate molecules. Functionally, peptides can be: 1) readily made cell permeable via coupling of cell penetrating motifs to enable drug-like function; or alternatively, 2) coupled to chemical moieties such as poly-ethylene glycol (PEG) or protein domains with naturally long serum half-life such as Fc, transferrin or albumin to improve persistence in circulation. For example, using the methods of the disclosure drug-like peptides were generated that opposed triple-negative breast cancer cell growth in vitro as effectively as some FDA approved small molecules targeting the same proteins. Advances in biologics delivery will further improve the translational relevance of this strategy. We anticipate a future role for this method of peptide inhibitor screening in both basic research and drug development.

The peptides of the disclosure (see, e.g., SEQ ID NOs: 1-9489) can be delivered to cells or subjects in a number of different ways known to those of skill in the art. For example, the peptides themselves may be formulated for delivery directly or they maybe engineered to comprise delivery molecules to assist in their targeting or uptake. For example, suitable delivery molecules include protein transduction domains (PTDs) (sometimes referred to as cell penetrating peptides (CPPs)), nanoparticles, liposomes etc.

In other embodiments, the polynucleotide encoding the peptides of the disclosure can be delivered to a cell such that they are "expressed" in the cell and provide their biological effect via the expression of the polynucleotide. Typically such polynucleotides will be operably linked to an expression control sequence (e.g., promoter, enhancer etc.). Depending upon the cell expressing the polynucleotide suitable promoters and/or vectors can be selected such that delivery and expression occur. In some embodiments, the vector used to deliver a polynucleotide encoding a peptide of the disclosure is a viral vector. Such viral vectors can be replication competent or replication defective. The viral vectors whether replication competent or replication defective can be "derived" (e.g., engineered from) any number of viral vector systems known in the art. For example, suitable viral vectors that can be engineered to contain a polynucleotide of the disclosure comprise gammaretroviruses (e.g., MLV), lentivirus, adenoviruses, alphaviruses etc. In some cases, where the viral vector is replication defective a suitable helper cell system is used.

Replication competent retroviral systems will typically comprise a viral capsid comprising GAG, POL and ENV proteins and a viral genome comprising sequences encoding GAG, POL and ENV as well as factors necessary for the integration and packaging of the viral genome. A cassette is typically engineered into the viral genome, wherein the cassette comprises an IRES, promoter or other regulatory factor upstream of the coding sequence of a peptide of the disclosure. The cassette is typically integrated into the viral genome in a location that does not disrupt expression of necessary viral genes and is typically located downstream of the env coding sequence or in the LTRs of the viral genome.

As described herein, the disclosure provides peptides that have dominant negative activity and have, for example, anticancer effects. In one embodiment, the peptides inhibit the biological activity of the molecule from which they are derived. By "anticancer effect" means that the molecule inhibits, for example, aberrant proliferative activity, invasiveness, cell growth, migration and any combinations thereof. The disclosure contemplates that the peptides of the disclosure can be delivered in a number of ways.

Cellular delivery can be accomplished by fusion of "cargo" biological agents (in this case the peptides of the disclosure) to a cationic Peptide Transduction Domain (PTD; also termed Cell Penetrating Peptide (CPP)) such as TAT or ($Arg_8$) (Snyder and Dowdy, 2005, *Expert Opin. Drug Deliv.* 2, 43-51). PTDs can be used to deliver a wide variety of macromolecular cargo, including the peptides described herein. Cationic PTDs enter cells by macropinocytosis, a specialized form of fluid phase uptake that all cells perform.

The discovery of several proteins which could efficiently pass through the plasma membrane of eukaryotic cells has led to the identification of a class of proteins from which peptide transduction domains have been derived. The best characterized of these proteins are the Drosophila homeoprotein antennapedia transcription protein (AntHD) (Joliot et al., *New Biol.* 3:1121-34, 1991; Joliot et al., *Proc. Natl. Acad. Sci. USA,* 88:1864-8, 1991; Le Roux et al., *Proc. Natl. Acad. Sci. USA,* 90:9120-4, 1993), the herpes simplex virus structural protein VP22 (Elliott and O'Hare, *Cell* 88:223-33, 1997), the HIV-1 transcriptional activator TAT protein (Green and Loewenstein, *Cell* 55:1179-1188, 1988; Frankel and Pabo, *Cell* 55:1189-1193, 1988), and more recently the cationic N-terminal domain of prion proteins. Exemplary PTD sequences are provided in Table 2. The disclosure further provides for one or more of the PTDs listed in Table 2 or other PTDs known in the art (see, e.g., Joliot et al., *Nature Cell Biology,* 6(3):189-196, 2004) to be conjugated to the peptides disclosed herein. Strategies for conjugation include the use of a bifunctional linker that includes a functional group that can be cleaved by the action of an intracellular enzyme.

TABLE 2

| PTD | Sequence | SEQ ID NO. |
|---|---|---|
| TAT | RKKRRQRRR | SEQ ID NO: 9490 |
| Penetratin | RQIKIWFQNRRMK WKK | SEQ ID NO: 9491 |
| Buforin II | TRSSRAGLQFPVG RVHRLLRK | SEQ ID NO: 9492 |
| Transportan | GWTLNSAGYLLGKI NKALAALAKKIL | SEQ ID NO: 9493 |
| MAP (model amphipathic peptide) | KLALKLALKALKA ALKLA | SEQ ID NO: 9494 |
| K-FGF | AAVALLPAVLLAL LAP | SEQ ID NO: 9495 |
| Ku70 | VPMLK - PMLKE | SEQ ID NO: 9496 |
| Prion | MANLGYWLLALFVT MWTDVGLCKKRPKP | SEQ ID NO: 9497 |
| pVEC | LLIILRRRIRKQAH AHSK | SEQ ID NO: 9498 |
| Pep-1 | KETWWETWWTEWS QPKKKRKV | SEQ ID NO: 9499 |

TABLE 2-continued

| PTD | Sequence | SEQ ID NO. |
|---|---|---|
| SynB1 | RGGRLSYSRRRFST STGR | SEQ ID NO: 9500 |
| Pep-7 (phage display) | SDLWEMMMVSLACQY | SEQ ID NO: 9501 |
| HN-1 (phage display) | TSPLNIHNGQKL | SEQ ID NO: 9502 |

Exemplary auxiliary moieties that can be conjugated to any of the constructs described herein are provided in Table 3.

TABLE 3

| Sequence (N' to C') (PTD = protein transduction domain) |
|---|
| PEG-(PTD) |
| GG-(PTD)-PEG-(PTD) |
| PEG-(PTD)-PEG-(PTD) |
| GG-(PTD)-PEG-PEG-PEG-(PTD) |
| PEG-(PTD)-PEG-PEG-PEG-(PTD) |
| GG-(PTD)-PEG-(PTD)-PEG-(PTD) |
| GG-(PTD)-PEG-PEG-PEG-(PTD)-PEG-PEG-PEG-(PTD) |

PEG = poly(ethyleneglycol) linker having two-six repeat units

In one embodiment, a PTD useful in the methods and compositions of the disclosure comprises a peptide or polypeptide featuring substantial alpha-helicity. It has been discovered that transfection can be optimized when the PTD exhibits significant alpha-helicity. In another embodiment, the PTD comprises a sequence containing basic amino acid residues that are substantially aligned along at least one face of the peptide or polypeptide. A PTD domain useful in the disclosure may be a naturally occurring peptide or polypeptide or a synthetic peptide or polypeptide.

In another embodiment, the PTD comprises an amino acid sequence comprising a strong alpha helical structure with arginine (Arg) residues down the helical cylinder.

In yet another embodiment, the PTD domain comprises a peptide represented by the following general formula: $B_{P1}$-$X_{P1}$-$X_{P2}$-$X_{P3}$-$B_{P2}$-$X_{P4}$-$X_{P5}$-$B_{P3}$ (SEQ ID NO:9503) wherein $B_{P1}$, $B_{P2}$, and $B_{P3}$ are each independently a basic amino acid, the same or different; and $X_{P1}$, $X_{P2}$, $X_{P3}$, $X_{P4}$, and $X_{P5}$ are each independently an alpha-helix enhancing amino acid, the same or different.

In another embodiment, the PTD domain is represented by the following general formula: $B_{P1}$-$X_{P1}$-$X_{P2}$-$B_{P2}$-$B_{P3}$-$X_{P3}$-$X_{P4}$-$B_{P4}$ (SEQ ID NO:9504) wherein $B_{P1}$, $B_{P2}$, $B_{P2}$, and $B_{P4}$ are each independently a basic amino acid, the same or different; and $X_{P1}$, $X_{P2}$, $X_{P3}$, and $X_{P4}$ are each independently an alpha-helix enhancing amino acid the same or different.

Additionally, PTD domains comprise basic residues, e.g., lysine (Lys) or arginine (Arg), and further can include at least one proline (Pro) residue sufficient to introduce "kinks" into the domain. Examples of such domains include the transduction domains of prions. For example, such a peptide comprises KKRPKPG (SEQ ID NO:9505).

In another embodiment the PTD is cationic and consists of between 7 and 10 amino acids. An example of such a peptide comprises RKKRRQRRR (SEQ ID NO:9490). In another example, the PTD is a cationic peptide sequence having 5-10 arginine (and/or lysine) residues over 5-15 amino acids.

Additional delivery domains in accord with this disclosure include a TAT fragment that comprises at least amino acids 49 to 56 of TAT up to about the full-length TAT sequence (see, e.g., SEQ ID NO:9490). A TAT fragment may include one or more amino acid changes sufficient to increase the alpha-helicity of the fragment. In some instances, the amino acid changes introduced will involve adding a recognized alpha-helix enhancing amino acid. Alternatively, the amino acid changes will involve removing one or more amino acids from the TAT fragment that impede alpha helix formation or stability. In a more specific embodiment, the TAT fragment will include at least one amino acid substitution with an alpha-helix enhancing amino acid. Typically the TAT fragment will be made by standard peptide synthesis techniques although recombinant DNA approaches may be used in some cases. In one embodiment, the substitution is selected so that at least two basic amino acid residues in the TAT fragment are substantially aligned along at least one face of that TAT fragment. In a more specific embodiment, the substitution is chosen so that at least two basic amino acid residues in the TAT 49-56 sequence are substantially aligned along at least one face of that sequence.

Additional transduction proteins (PTDs) that can be used in the compositions and methods of the disclosure include the TAT fragment in which the TAT 49-56 sequence has been modified so that at least two basic amino acids in the sequence are substantially aligned along at least one face of the TAT fragment. Illustrative TAT fragments include at least one specified amino acid substitution in at least amino acids 49-56 of TAT which substitution aligns the basic amino acid residues of the 49-56 sequence along at least one face of the segment and typically the TAT 49-56 sequence.

Thus, PTDs that can be conjugated to a peptide of the disclosure include, but are not limited to, AntHD, TAT, VP22, cationic prion protein domains, and functional fragments thereof. Not only can these peptides pass through the plasma membrane, but the attachment of other peptide or polypeptides are sufficient to stimulate the cellular uptake of these complexes. Such chimeric peptides/polypeptide are present in a biologically active form within the cytoplasm and nucleus. Characterization of this process has shown that the uptake of these fusion polypeptides can be rapid, often occurring within minutes, in a receptor independent fashion. Moreover, the transduction of these proteins does not appear to be affected by cell type, and these proteins can efficiently transduce ~100% of cells in culture with no apparent toxicity (Nagahara et al., *Nat. Med.* 4:1449-52, 1998).

In a particular embodiment, the disclosure therefore provides methods and compositions that combine the use of PTDs, such as TAT and poly-Arg, with a drug-like peptide disclosed herein to facilitate the uptake of the construct into and/or release within targeted cells. The drug-like peptides disclosed herein can be delivered into cells using one or more PTDs linked to the drug-like peptide.

In general, the delivery domain that is linked to a drug-like peptide disclosed herein can be nearly any synthetic or naturally-occurring amino acid sequence which assists in the intracellular delivery of a construct disclosed herein into targeted cells. For example, delivery of a drug-like peptide (see, Table 1) in accordance with the disclosure can be accomplished by use of a peptide transduction domain, such as an HIV TAT protein or fragment thereof, that is covalently linked to a drug-like peptide of the disclosure. Alternatively, the peptide transduction domain can comprise the Antennapedia homeodomain or the HSV VP22 sequence, the N-terminal fragment of a prion protein or suitable transducing fragments thereof such as those known in the art.

The type and size of the PTD will be guided by several parameters including the extent of transfection desired. Typically the PTD will be capable of transfecting at least about 20%, 25%, 50%, 75%, 80% or 90%, 95%, 98% and up to, and including, about 100% of the cells. Transfection efficiency, typically expressed as the percentage of transfected cells, can be determined by several conventional methods.

PTDs will manifest cell entry and exit rates (sometimes referred to as $k_1$ and $k_2$, respectively) that favor at least picomolar amounts of a construct disclosed herein into a targeted cell. The entry and exit rates of the PTD and any cargo can be readily determined or at least approximated by standard kinetic analysis using detectably-labeled fusion molecules. Typically, the ratio of the entry rate to the exit rate will be in the range of between about 5 to about 100 up to about 1000.

Also included are chimeric PTD domains. Such chimeric PTDs include parts of at least two different transducing proteins. For example, chimeric PTDs can be formed by fusing two different TAT fragments, e.g., one from HIV-1 and the other from HIV-2 or one from a prion protein and one from HIV.

Peptide linkers that can be used in the constructs and methods of the disclosure will typically comprise up to about 20 or 30 amino acids, commonly up to about 10 or 15 amino acids, and still more often from about 1 to 5 amino acids. The linker sequence is generally flexible so as not to hold the fusion molecule in a single rigid conformation. The linker sequence can be used, e.g., to space the PTD domain from a drug-like peptide to be delivered. For example, the peptide linker sequence can be positioned between the peptide transduction domain and the therapeutic drug-like peptide domain, e.g., to provide molecular flexibility. The length of the linker moiety can be chosen to optimize the biological activity of the peptide or polypeptide comprising, for example, a PTD domain fusion construct and can be determined empirically without undue experimentation. Examples of linker moieties are -Gly-Gly-, GGGGS (SEQ ID NO:9506), wherein SEQ ID NO:19 can be repeated 1 or more times, GKSSGSGSESKS (SEQ ID NO:9507), GSTSGSGKSSEGKG (SEQ ID NO:9508), GSTSGSGKSSEGSGSTKG (SEQ ID NO:9509), GSTSGSGKPGSGEGSTKG (SEQ ID NO:9510), or EGKSSGSGSESKEF (SEQ ID NO:9511). Peptide or polypeptide linking moieties are described, for example, in Huston et al., *Proc. Nat'l Acad. Sci.* 85:5879, 1988; Whitlow et al., Protein Engineering 6:989, 1993; and Newton et al., *Biochemistry* 35:545, 1996. Other suitable peptide or polypeptide linkers are those described in U.S. Pat. Nos. 4,751,180 and 4,935,233, which are hereby incorporated by reference.

The amino acid sequences of the various oncogenic and receptor proteins described herein are provided and known in the art (see, Table 1). The drug-like peptides of the disclosure (see, Table 1), may be synthesized by solid-phase peptide synthesis methods using procedures similar to those described by Merrifield et al., J. Am. Chem. Soc., 85:2149-2156 (1963); Barany and Merrifield, Solid-Phase Peptide Synthesis, in The Peptides: Analysis, Synthesis, Biology Gross and Meienhofer (eds.), Academic Press, N.Y., vol. 2, pp. 3-284 (1980); and Stewart et al., Solid Phase Peptide Synthesis 2nd ed., Pierce Chem. Co., Rockford, Ill. (1984). During synthesis, N-α-protected amino acids having protected side chains are added stepwise to a growing polypeptide chain linked by its C-terminal and to a solid support, e.g., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. A commonly used N-α-protecting groups include Boc, which is acid labile, and Fmoc, which is base labile.

Materials suitable for use as the solid support are well known to those of skill in the art and include, but are not limited to: halomethyl resins, such as chloromethyl resin or bromomethyl resin; hydroxymethyl resins; phenol resins, such as 4-(α[2,4-dimethoxyphenyl]-Fmoc-aminomethyl) phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid can be first attached to the solid support. The N-α-protecting group can then be removed. The deprotected α-amino group can be coupled to the activated a-carboxylate group of the next N-α-protected amino acid. The process can be repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., Solid Phase Peptide Synthesis: A Practical Approach, IRL Press (1989), and Bodanszky, Peptide Chemistry, A Practical Textbook, 2nd Ed., Springer-Verlag (1993)).

Following verification of the coding sequence, a peptide of interest (e.g., a drug-like peptide of the disclosure) can be produced using routine techniques in the field of recombinant molecular biology, relying on the polynucleotide sequences encoding the peptide. The coding sequence of the peptide can be easily deduced using the degeneracy of the genetic code and a codon table.

To obtain high level expression of a nucleic acid encoding a peptide of interest, one typically subclones the polynucleotide coding sequence into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al. Bacterial expression systems for expressing recombinant polypeptides are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. In some embodiments, the promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the desired peptide in host cells. A typical expression cassette thus contains a promoter operably linked to the nucleic acid sequence encoding the peptide and signals required for efficient polyadenylation of the transcript, ribosome binding sites, and translation termination. The nucleic acid sequence encoding the desired peptide is typically linked to a cleavable signal peptide sequence to promote secretion of the recombinant polypeptide by the transformed cell. Such signal peptides include, among others, the signal peptides from tissue plasminogen activator, insulin, and neuron growth factor, and juvenile hormone esterase of Heliothis virescens. If, however, a recombinant polypeptide is intended to be expressed on the host cell surface, an appropriate anchoring sequence is used in concert with the coding sequence. Additional elements of the cassette may include enhancers and, if genomic DNA is used as the structural gene, introns with functional splice donor and acceptor sites.

In addition to a promoter sequence, the expression cassette should also contain a transcription termination region downstream of the structural peptide coding sequence to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/$A^+$, pMTO10/$A^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the desired peptide under the direction of the polyhedrin promoter or other strong baculovirus promoters.

When periplasmic expression of a recombinant polypeptide is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the peptide to be expressed. This signal sequence directs the recombinant peptide produced in the cytoplasm through the cell membrane into the periplasmic space. The expression vector may further comprise a coding sequence for signal peptidase 1, which is capable of enzymatically cleaving the signal sequence when the recombinant peptide is entering the periplasmic space. More detailed description for periplasmic production of a recombinant protein can be found in, e.g., Gray et al., Gene 39: 247-254 (1985), U.S. Pat. Nos. 6,160,089 and 6,436,674.

Standard transfection methods are used to produce bacterial, mammalian, yeast, insect, or plant cell lines that express large quantities of a recombinant peptide or polypeptide, which are then purified using standard techniques (see, e.g., Colley et al., J. Biol. Chem. 264: 17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132: 349-351 (1977); Clark-Curtiss & Curtiss, Methods in Enzymology 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell. In some embodiments, it is only necessary that the particular genetic engineering procedure used be capable of successfully introducing at least one gene into the host cell capable of expressing the recombinant polypeptide.

In some embodiments, once the expression of a recombinant peptide in transfected host cells is confirmed, e.g., by an immunological assay, activity assay or sequencing, the host cells are then cultured in an appropriate scale for the purpose of purifying the recombinant peptide.

When desired polypeptides are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that can be both a strong hydrogen acceptor and a strong hydrogen donor (or a combination of solvents each having one of these properties). The peptides that formed the inclusion bodies may then be renatured by dilution or dialysis with a compatible buffer.

Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming peptides, such as SDS (sodium dodecyl sulfate) and 70% formic acid, may be inappropriate for use in this procedure due to the possibility of irreversible denaturation of the peptides, accompanied by a lack of immunogenicity and/or activity. Although guanidine hydrochloride and similar agents are denaturants, this denaturation may not be irreversible and renaturation may occur upon removal (by dialysis, for example) or dilution of the denaturant, allowing re-formation of the immunologically and/or biologically active protein of interest. After solubilization, the peptide can be separated from other bacterial proteins by standard separation techniques. For further description of purifying recombinant peptides from bacterial inclusion body, see, e.g., Patra et al., Protein Expression and Purification 18: 182-190 (2000).

Alternatively, it is possible to purify recombinant peptides from bacterial periplasm. In some cases, where the recombinant peptide is exported into the periplasm of the bacteria, the periplasmic fraction of the bacteria can be isolated by cold osmotic shock in addition to other methods known to those of skill in the art (see e.g., Ausubel et al., supra). To isolate recombinant peptides from the periplasm, the bacterial cells can be centrifuged to form a pellet. The pellet is resuspended in a buffer containing 20% sucrose. To lyse the cells, the bacteria can be centrifuged and the pellet can then be resuspended in ice-cold 5 mM $MgSO_4$ and kept in an ice bath for approximately 10 minutes. The cell suspension can be centrifuged and the supernatant decanted and saved. The recombinant peptides present in the supernatant can be separated from the host proteins by standard separation techniques well known to those of skill in the art.

When a recombinant polypeptide or peptide is expressed in host cells in a soluble form, its purification can follow the standard protein purification procedure described below. This standard purification procedure can also be suitable for purifying polypeptides obtained from chemical synthesis.

In some embodiments, as an initial step, and if the protein mixture is complex, an initial salt fractionation can separate many of the unwanted host cell proteins (or proteins derived from the cell culture media) from the recombinant peptide of interest. A typical salt is ammonium sulfate. Ammonium sulfate precipitates polypeptides by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. In some cases, this will precipitate the most hydrophobic proteins. The precipitate can be discarded (unless the protein of interest is hydrophobic) and ammonium sulfate can be added to the supernatant to a concentration known to precipitate the protein of interest. The precipitate can then be solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

The drug-like peptides of the disclosure can also be separated from other proteins on the basis of their size, net surface charge, hydrophobicity, or affinity for ligands.

For delivery to a cell or organism, a nucleic acid encoding a drug-like peptide of the disclosure can be incorporated into a vector. Examples of vectors used for such purposes include expression plasmids capable of directing the expression of the drug-like peptide in the target cell. In other instances, the vector can be a viral vector system wherein the nucleic acid encoding the drug-like peptide is incorporated into a viral genome that is capable of transfecting the target cell.

As used herein, "gene delivery system" refers to any means for the delivery of a nucleic acid encoding a drug-like peptide of the disclosure to a target cell. Viral vector systems useful in the introduction and expression of a nucleic acid include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the nucleic acid is inserted into such vectors to allow packaging of the gene construct, typically with accompanying viral DNA, followed by infection of a sensitive host cell and expression of the gene of interest.

Similarly, viral envelopes used for packaging gene constructs that include the nucleic acid can be modified by the addition of receptor ligands or antibodies specific for a receptor to permit receptor-mediated endocytosis into specific cells.

Retroviral vectors may also be useful for introducing the nucleic acid into target cells or organisms. Retroviral vectors are produced by genetically manipulating retroviruses. The viral genome of retroviruses is RNA. Upon infection, this genomic RNA is reverse transcribed into a DNA copy that is integrated into the chromosomal DNA of transduced cells with a high degree of stability and efficiency. The integrated DNA copy is referred to as a provirus and is inherited by daughter cells as is any other gene. The wild type retroviral genome and the proviral DNA comprise three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: Experimental Manipulation of Gene Expression, Inouye (ed), 155-173 (1983); Mann et al., Cell 33:153-159 (1983); Cone and Mulligan, Proceedings of the National Academy of Sciences, U.S.A., 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa Biotechniques 4:504-512 (1986); Mann et al., Cell 33:153-159 (1983); Cone and Mulligan Proc. Natl. Acad. Sci. USA 81:6349-6353 (1984); Eglitis et al. Biotechniques 6:608-614 (1988); Miller et al. Biotechniques 7:981-990 (1989); Miller (1992) supra; Mulligan (1993), supra; and WO 92/07943.

The retroviral vector particles are prepared by recombinantly inserting the desired nucleic acid sequence encoding a drug-like peptide of the disclosure into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence.

Delivery of a drug-like peptide of the disclosure can be achieved by contacting a cell with a nucleic acid construct or using direct delivery of the drug-like peptide or fusion peptide. In a particular embodiment, a drug-like peptide of the disclosure (e.g., a therapeutic peptide) can be formulated with various carriers, dispersion agents and the like, as are described more fully elsewhere herein.

A pharmaceutical composition according to the disclosure can be prepared to include a drug-like peptide as disclosed herein, into a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, and The National Formulary, 30th ed., the contents of which are hereby incorporated by reference. The pH and exact concentration of the various components of the pharmaceutical composition are adjusted according to routine skills in the art. See Goodman and Gilman's, The Pharmacological Basis for Therapeutics.

The pharmaceutical compositions according to the disclosure may be administered locally or systemically. The therapeutically effective amounts will vary according to factors, such as the degree of infection in a subject, the age, sex, and weight of the individual. Dosage regimes can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (e.g., subcutaneous, intravenous, intraorbital, and the like), oral administration, ophthalmic application, inhalation, transdermal application, topical application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically, the composition will be stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the subject's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit. The tablets, troches, pills, capsules, and the like can also contain the following: a binder, such as gum tragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

Thus, a pharmaceutically acceptable carrier can include solvents, dispersion media, coatings, antibacterial and antifungal agents, isotonic and absorption delaying agents, and the like. In some cases, the use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

In some embodiments, it can be especially advantageous to formulate parenteral compositions in dosage unit form for ease of administration and uniformity of dosage. Dosage unit form as used herein, refers to physically discrete units suited as unitary dosages for the subject to be treated; each unit containing a predetermined quantity of pharmaceutical composition can be calculated to produce the desired therapeutic effect in association with the required pharmaceutical carrier. The specification for the dosage unit forms of the disclosure are related to the characteristics of the pharmaceutical composition and the particular therapeutic effect to be achieve. The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

For topical formulations, the base composition can be prepared with any solvent system, such as those Generally Regarded as Safe (GRAS) by the U.S. Food & Drug Administration (FDA). GRAS solvent systems include many short chain hydrocarbons, such as butane, propane, n-butane, or a mixture thereof, as the delivery vehicle, which are approved by the FDA for topical use. The topical compositions can be formulated using any dermatologically acceptable carrier. Exemplary carriers include a solid carrier, such as alumina, clay, microcrystalline cellulose, silica, or talc; and/or a liquid carrier, such as an alcohol, a glycol, or a water-alcohol/glycol blend. The compounds may also be administered in liposomal formulations that allow compounds to enter the skin. Such liposomal formulations are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; and PCT Publication No. WO 96/40061. Examples of other appropriate vehicles are described in U.S. Pat. Nos. 4,877,805, 4,980,378, 5,082,866, 6,118,020 and EP Publication No. 0586106A1. Suitable vehicles of the disclosure may also include mineral oil, petrolatum, polydecene, stearic acid, isopropyl myristate, polyoxyl 40 stearate, stearyl alcohol, or vegetable oil.

Topical compositions can be provided in any useful form. For example, the compositions of the disclosure may be formulated as solutions, emulsions (including microemulsions), suspensions, creams, foams, lotions, gels, powders, balm, or other typical solid, semi-solid, or liquid compositions used for application to the skin or other tissues where the compositions may be used. Such compositions may contain other ingredients typically used in such products, such as colorants, fragrances, thickeners, antimicrobials, solvents, surfactants, detergents, gelling agents, antioxidants, fillers, dyestuffs, viscosity-controlling agents, preservatives, humectants, emollients (e.g., natural or synthetic oils, hydrocarbon oils, waxes, or silicones), hydration agents, chelating agents, demulcents, solubilizing excipients, adjuvants, dispersants, skin penetration enhancers, plasticizing agents, preservatives, stabilizers, demulsifiers, wetting agents, sunscreens, emulsifiers, moisturizers, astringents, deodorants, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

In some formulations, the composition can be formulated for ocular application. For example, a pharmaceutical formulation for ocular application can include a polynucleotide construct as described herein in an amount that is, e.g., up to 99% by weight mixed with a physiologically acceptable ophthalmic carrier medium such as water, buffer, saline, glycine, hyaluronic acid, mannitol, and the like. For ophthalmic delivery, a polynucleotide construct as described herein may be combined with ophthalmologically acceptable preservatives, co-solvents, surfactants, viscosity enhancers, penetration enhancers, buffers, sodium chloride, or water to form an aqueous, sterile ophthalmic suspension or solution. Ophthalmic solution formulations may be prepared by dissolving the polynucleotide construct in a physiologically acceptable isotonic aqueous buffer. Further, the ophthalmic solution may include an ophthalmologically acceptable surfactant to assist in dissolving the inhibitor. Viscosity building agents, such as hydroxymethyl cellulose, hydroxyethyl cellulose, methylcellulose, polyvinylpyrrolidone, or the like may be added to the compositions of the disclosure to improve the retention of the compound.

Topical compositions can be delivered to the surface of the eye, e.g., one to four times per day, or on an extended delivery schedule such as daily, weekly, bi-weekly, monthly, or longer, according to the routine discretion of a skilled clinician. The pH of the formulation can range from about pH 4-9, or about pH 4.5 to pH 7.4.

For nucleic acid constructs of the disclosure, suitable pharmaceutically acceptable salts include (i) salts formed with cations such as sodium, potassium, ammonium, magnesium, calcium, polyamines such as spermine and spermidine, etc.; (ii) acid addition salts formed with inorganic acids, for example hydrochloric acid, hydrobromic acid, sulfuric acid, phosphoric acid, nitric acid and the like; (iii) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (iv) salts formed from elemental anions such as chlorine, bromine, and iodine.

The disclosure provides methods for treating a subject with a cancer or suspected of having a cancer comprising administering a drug-like peptide of the disclosure (see, Table 1) comprising a therapeutically effective amount of one or more drug-like peptide and optionally one or more anticancer agents disclosed herein. A therapeutically effective amount can be measured as the amount sufficient to prevent cancer cells from dividing, metastasizing and/or growing, ultimately killing the cancer cells or reducing the metastatic potential of the cancer cell. Generally, the optimal dosage of will depend upon the type and stage of the cancer and factors such as the weight, sex, and condition of the subject. Nonetheless, suitable dosages can readily be determined by one skilled in the art. Typically, dosages used in vitro may provide useful guidance in the amounts useful for in situ administration of the pharmaceutical composition, and animal models may be used to determine effective dosages for treatment of specific cancers. Various considerations are described, e.g., in Langer, Science, 249: 1527, (1990); Gilman et al. (eds.) (1990), each of which is herein incorporated by reference. Typically, a suitable dosage can be 1 to 1000 mg/kg body weight, e.g., 10 to 500 mg/kg body weight. In a particular embodiment, a drug-like peptide disclosed herein can be administered at dosage of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 210 mg/kg, 220 mg/kg, 230 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 100 mg/kg, or a range that includes or is between any two of the foregoing dosages, including fractional dosages thereof.

Examples, of anticancer agents that can be used with the drug-like peptides disclosed herein include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; vinca alkaloids; epipodophyllotoxins; antibiotics such as the enediyne antibiotics (e.g., calicheamicin, especially calicheamicin gammall and calicheamicin omegall; L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2 2"-trichlorotiiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® (docetaxel) (Rhone-Poulenc Rorer, Antony, France); chloranbucil; GEMZAR® (gemcitabine); 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids such as retinoic acid; capecitabine; leucovorin (LV); irenotecan; adrenocortical suppressant; adrenocorticosteroids; progestins; estrogens; androgens; gonadotropin-releasing hormone analogs; and pharmaceutically acceptable salts, acids or derivatives of any of the above. Also included anticancer agents are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASL® exemestane, formestanie, fadrozole, RIVISOR® vorozole, FEMARA® letrozole, and ARTMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF-A expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rJL-2; LURTOTECAN® topoisomerase 1 inhibitor; ABARELLX® rmRH; antibodies such as trastuzumab and pharmaceutically acceptable salts, acids or derivatives of any of the above. In a particular embodiment, the disclosure provides for combined therapy comprising one or more drug-like peptides disclosed herein used in combination with a tyrosine kinase inhibitor (TKI). Examples of protein kinase inhibitors, include but are not limited to, adavosertib, afatinib, axitinib, bosutinib, cetuximab, cobimetinib, crizotinib, cabozantinib, dasatinib, entrectinib, erdafitinib, erlotinib, fostamatinib, gefitinib, ibrutinib, imatinib, lapatinib, lenvatinib, mubritinib, nilotinib, pazopanib, pegaptanib, ruxolitinib, sorafenib, sunitinib, SU6656, vandetanib, and vemurafenib. In another embodiment, the disclosure provides for combined therapy comprising one or more drug-like peptides disclosed herein used in combination with an angiogenesis inhibitor. Examples of angiogenesis inhibitors, include but are not limited to, axitinib, bevacizumab, cabozantinib, everolimus, lenalidomide, lenvatinib mesylate, pazopanib, ramucirumab, regorafenib, sorafenib, sunitinib, thalidomide, vandetanib, and Ziv-aflibercept. In another embodiment, the disclosure provides for combined therapy comprising one or more drug-like peptides disclosed herein used in combination with a PARP inhibitor. Examples of PARP inhibitors, include but are not limited to, olaparib, niraparib, rucaparib, and talzoparib. The anticancer agent may be administered, by a route and in an amount commonly used therefore, simultaneously (at the same time or in the same formulation) or sequentially with a drug-like peptide as disclosed herein. When a drug-like peptide as disclosed herein is used contemporaneously with one or more anticancer agents, a pharmaceutical composition containing the one or more anticancer agents in addition to a drug-like peptide disclosed herein may be utilized but may not be required. Accordingly, the pharmaceutical compositions disclosed herein include those that also contain one or more anticancer agents in addition to a drug-like peptide disclosed herein.

Provided herein can be peptides or salts thereof and compositions comprising the same. Peptides can be of any length. In some cases, a peptide can have a sequence length from: about 5 amino acids to about 80 amino acids, about 5 amino acids to about 20 amino acids, about 10 amino acids to about 40 amino acids, about 20 amino acids to about 60 amino acids, about 20 amino acids to about 50 amino acids, or about 40 amino acids to about 80 amino acids. In some cases, a peptide or salt thereof can have a sequence length of less than about: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids. In some cases, a peptide can have a sequence length of more than about: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acids.

In some cases, peptides provided herein can comprise at least partial sequence identity to wildtype proteins. In some cases, peptides provided herein can comprise mutations as compared to a wildtype peptide sequence. In some cases, a peptide provided herein can comprise a continuous sequence having from about 7-17, 7-15, 7-10, 8-17, 8-15, 8-10, 9-17, 9-15, or 9-10 residues identical to a sequence provided in any one of SEQ ID NO: 1-9489 or a polypeptide recited in SEQ ID NO: 9521, 9522, 9526, 9530, or 9531. In some cases, at least a contiguous portion of the peptide or salt thereof can comprise a sequence with at least about: 70%, 75%, 80%, 85%, 90%, 91%, 92%, 93%, 94%, 95%, 96%, 97%, 98%, 99%, or 100% sequence identity to a polypeptide recited in SEQ ID NO: 1-9489. In some cases, a peptide or salt thereof can comprise a sequence with at least about: 70%, 75%, 80%, 85%, 90%, 91%, 92%, 93%, 94%, 95%, 96%, 97%, 98%, 99%, or 100% sequence identity to a polypeptide recited in SEQ ID NO: 9521, 9522, 9526, 9530, 9531 or 9701. In some cases, a peptide provided herein comprises less than about 10, 9, 8, 7, 6, 5, 4, 3, 2, or 1 residue difference to a polypeptide provided in any one of SEQ ID NO: 1-9489. In some cases, a peptide comprises 70%, 75%, 80%, 85%, 90%, 91%, 92%, 93%, 94%, 95%, 96%, 97%, 98%, 99%, or 100% sequence identity to the polypeptide of SEQ ID NO 9530.

In some embodiments, a peptide or salt thereof can modulate expression level of a target protein. In some cases, a target protein can be implicated in a disease or condition. Non-limiting examples of suitable genes that can encode a target protein are provided in Table 7.

In some instances, a target protein can comprise an enzyme or fragment thereof. In some instances, a target protein can comprise, a kinase, a phosphatase, a signaling peptide, a transcription factor, or any combination thereof. In some cases, a target protein can comprise an oxidoreductase, a hydrolase, a transferase, a lyase, an isomerase, or a ligase. In some cases, a target protein can be encoded by a gene in Table 7 or a variant of a gene in Table 7 or a fragment of any of these. Table 7 comprises non-limiting exemplary genes that can encode for a target protein.

In some cases, a peptide or salt thereof can modulate a target protein. Modulation of a target protein by a peptide or salt thereof can comprise at least a partial inhibition, reduction, or total elimination of activity. In some cases, modulation can comprise at least a partial increase in activity. In some cases, modulation can be achieved by at least partially inhibiting or activating protein to protein interaction. In some cases, a protein to protein interaction can comprise a ligand to receptor interaction. In some instances, a protein to protein interaction can comprise a regulatory protein complex. In some cases, a peptide or salt thereof can at least partially reduce a protein to nucleic acid interaction.

TABLE 7

| Exemplary genes that encode exemplary target proteins: | | | |
|---|---|---|---|
| MCL-1 | CRLF2 | PCDH15 | POMGNT1 |
| BCR | DSE | PTGFR | RYR2 |
| BRAF | EXT1 | SGCD | STAG2 |
| JAK1 | FMR1 | TMEM127 | GNAQ |
| JAK2 | AKAP9 | HSPH1 | KDR |
| VEGF | ATRX | LRPPRC | MITF |
| EGFR | CBS | MYC | NOTCH1 |
| ALK | CRTAP | PCGF2 | POMT1 |
| CDK1 | DSG2 | PTPN11 | S1PR2 |
| CDK2 | EXT2 | SGSH | STAR |
| CDK3 | FUBP1 | TMEM43 | GNAS |
| CDK3 | AKT1 | IDH1 | KEAP1 |
| CDK4 | AXIN1 | LRRK2 | MKS1 |
| BRCA | CCDC178 | MYD88 | NOTCH2 |
| PIK3CA | CRYAB | PDE11A | POU1F1 |
| MEK | DSP | PTPN12 | SAMD9L |
| C-KIT | EYA4 | SH2B3 | STK11 |
| NRAS | FZD3 | TMEM67 | GNPTAB |
| ABCB11 | AKT2 | IDH2 | KIF1B |
| ANTXR2 | AXIN2 | LYST | MLH1 |
| BCOR | CCNE1 | MYH6 | NPC1 |
| CDKN1B | CSF1R | PDGFRA | POU6F2 |
| CYP27A1 | DTNA | RAC1 | SBDS |
| EMD | EZH2 | SLC25A4 | SUFU |
| FANCF | G6PC | TMPO | GPC3 |
| ABCC8 | ALB | IGF2R | KIT |
| APC | BAG3 | MAP2K1 | MLH3 |
| BCORL1 | CD79A | MYH7 | NPC2 |

TABLE 7-continued

| Exemplary genes that encode exemplary target proteins: | | | |
|---|---|---|---|
| CDKN2A | CSMD3 | PDHA1 | PPM1L |
| CYP27B1 | ECT2L | RAD21 | SCN11A |
| EP300 | F11 | SLC26A2 | SUZ12 |
| FANCG | GAA | TNFAIP3 | GPC6 |
| ABCC9 | ALDH3A2 | IGHMBP2 | KLF6 |
| AR | BAI3 | MAP2K2 | MMAB |
| BLM | CD79B | MYL2 | NPHP1 |
| CEP290 | CSRP3 | PDZRN3 | PPP2R1A |
| DAXX | EDA | RAD50 | SCN5A |
| EPCAM | F5 | SLC37A4 | SYNE3 |
| FANCI | GABRA6 | TNFRSF14 | GPR78 |
| ABCD1 | ALDOB | IGSF10 | KLHDC8B |
| ARID1A | BAP1 | MAP2K4 | MPL |
| BMPR1A | CD96 | MYL3 | NPHP4 |
| CFTR | CTNNB1 | PEX1 | PPT1 |
| DBT | EDN3 | RAD51B | SCNN1A |
| EPHA5 | FAH | SLC7A8 | TAZ |
| FANCL | GALNT12 | TNNC1 | GRIN2A |
| ABL1 | ALK | IKBKAP | KMT2A |
| ARID2 | BARD1 | MAP3K1 | MPZ |
| RAFI | CDC27 | MYLK2 | NPM1 |
| CHEK1 | CTNS | PEX7 | PRDM1 |
| DCC | EDNRB | RAD51C | SCNN1B |
| EPHB2 | FAM46C | SLC9A9 | TBX20 |
| FANCM | GALT | TNNI3 | GRM8 |
| ACADM | ALS2 | IKZF1 | KMT2C |
| ARSA | BAX | MAP4K3 | MRE11A |
| BRCA1 | CDC73 | MYO1B | PRKAG2 |
| CHEK2 | CTSK | PHF6 | SCNN1G |
| DCX | EED | RAD51D | TCAP |
| ERBB2 | FANCA | SLX4 | GXYLT1 |
| FAS | GATA1 | TNNT1 | KMT2D |
| CADS | AMER1 | IKZF4 | MSH2 |
| ASAH1 | BAZ2B | MAP7 | NRCAM |
| BRCA2 | CDH1 | MYO7A | PRKAR1A |
| CHM | CUBN | PIK3CA | SCO2 |
| DDB2 | EGFR | RARB | TCERG1 |
| ERBB3 | FANCB | SMAD2 | H3F3A |
| FAT3 | GATA2 | TNNT2 | KRAS |
| ACADVL | AMPD1 | IL2RG | MSH3 |
| ASCC1 | BCKDHA | MAPK10 | NTRK1 |
| BRIP1 | CDH23 | MYOZ2 | PRKDC |
| CIC | CYLD | PIK3CG | SDHA |
| DDR2 | EGR2 | RB1 | TCF7L2 |
| ERBB4 | FANCC | SMAD4 | HADHA |
| FBXO11 | GATA3 | TP53 | KREMEN1 |
| ACTC1 | AMPH | IL6ST | MSH6 |
| ASL | BCKDHB | MAS1L | NUP62 |
| BTD | CDK12 | MYPN | PROC |
| CLN3 | CYP11A1 | PIK3R1 | SDHAF2 |
| DES | EHBP1 | RBM20 | TERT |
| ERCC2 | FANCD2 | SMARCA4 | HADHB |
| FBXO32 | GATAD1 | TPM1 | L1CAM |
| ACTN2 | ANTXR1 | IL7R | MSMB |
| ASPA | BCL6 | MAX | OR5L1 |
| BTK | CDK4 | NBN | PROP1 |
| CLN5 | CYP21A2 | PKHD1 | SDHB |
| DHCR7 | ELMO1 | RECQL4 | TET2 |
| ERCC3 | FANCE | SMARCB1 | HBB |
| FBXW7 | GBA | TPP1 | LAMA2 |
| ACVR1B | GCDH | INVS | MSR1 |
| ASS1 | JAK1 | MC1R | OTC |
| BUB1B | MDM2 | NCOA3 | PRPF40B |
| CLN6 | NEK2 | PKP2 | SDHC |
| DICER1 | PLOD1 | RET | TFG |
| ERCC4 | ROS1 | SMC1A | HESX1 |
| FGD4 | SMPD1 | TRAF5 | LAMA4 |
| ADA | GJB2 | IRAK4 | MTAP |
| ASXL1 | JAK2 | MCCC2 | OTOP1 |
| CALR3 | MECP2 | NCOR1 | PRX |
| CLN8 | NEXN | PLEKHG5 | SDHD |
| DIS3L2 | PLP1 | RHBDF2 | TGFB3 |
| ERCC5 | RPGRIP1L | SMC3 | HEXA |
| FGFR1 | SOX10 | TRIO | LAMP2 |
| ADAMTS13 | GLA | ITCH | MTHFR |
| ATM | JAK3 | MCOLN1 | PAH |
| CARD11 | MED12 | NDUFA13 | PSAP |
| COL1A2 | NF1 | PLN | SEPT9 |

TABLE 7-continued

| Exemplary genes that encode exemplary target proteins: | | | |
|---|---|---|---|
| DKC1 | PMP22 | RNASEL | TGFBR1 |
| ERCC6 | RS1 | SMO | HEXB |
| FGFR2 | SOX2 | TRPV4 | LDB3 |
| ADAMTS2 | GLB1 | TRRAP | MTM1 |
| ATP4A | JUP | U2AF1 | PALB2 |
| CASP8 | MEFV | USH1C | PSEN1 |
| COL4A3 | NF2 | WAS | SETBP1 |
| DLD | PMS2 | WWP1 | TGFBR2 |
| ERRFI1 | RSPO1 | ZIC3 | HFE |
| FGFR3 | SPEG | TSC1 | LEPRE1 |
| AGA | GLI1 | U2AF2 | MTOR |
| ATP6V0D2 | KAT6A | USH1G | PALLD |
| CAV3 | MEN1 | WBSCR17 | PSEN2 |
| COL4A4 | NFE2L2 | XPA | SETD2 |
| DMD | POLD1 | ZNF2 | THSD7B |
| ESCO2 | RTEL1 | TSC2 | HGSNAT |
| FH | SPOP | UBA1 | LIG4 |
| AGL | GLI3 | USP16 | MUC16 |
| ATP7A | KCNQ1 | WEE1 | PAX5 |
| CBFB | MET | XPC | PTCH1 |
| COL7A1 | NFKBIA | ZNF226 | SF1 |
| DNAJB2 | POLE | TSHB | TINF2 |
| ESR1 | RUNX1 | UBR3 | HIST1H3B |
| FKTN | SRC | USP25 | LMNA |
| AGPS | GLMN | WNK2 | MUT |
| ATP7B | KDM4B | XRCC3 | PAX6 |
| CBL | MFSD8 | ZNF473 | PTCH2 |
| COX15 | NIPA2 | TSHR | SF3A1 |
| DNMT3A | POLH | UROD | TMC6 |
| ETV6 | RUNX1T1 | VCL | HNF1A |
| FLCN | SSTR1 | WRN | LPAR2 |
| AHI1 | GNA11 | ZBED4 | MUTYH |
| ATP8B1 | KDM6A | ZNF595 | PBRM1 |
| CBLB | MIER3 | TTN | PTEN |
| CREBBP | NKX3-1 | UROS | SF3B1 |
| DSC2 | AIP | VHL | TMC8 |
| EXOC2 | ATR | WT1 | HRAS |
| FLT3 | CBLC | ZFHX3 | LRP1B |
| ARAF | ZRSR2 | HER2 | MYBPC3 |

In some cases, modulation of expression level can be determined using an in vitro assay. In some cases, modulation of activity can be measured relative to an amount of the target protein or activity by a target protein in a cell that has not been treated with a peptide or salt thereof. In some cases, an assay can be utilized to measure kinase activity or phosphatase activity of a target protein. In some cases, kinase or phosphatase activity can be determined by evaluating activity of proteins downstream from the target protein. Downstream proteins can comprise proteins that can interact with a target protein directly or indirectly. In some cases, a downstream protein is at least about 1, 2, 3, 4, 5, 6, 7, 8, 9, or up to 10 proteins removed from the target protein in a pathway of a cell.

Any in vitro assay can be utilized in a method provided herein. In some cases, an in vitro assay comprises a Western blot, PCR, RNA sequencing, Northern blot, qPCR, ELISA, flow cytometry, fluorescence staining, and any combination thereof.

In some cases, a peptide or salt thereof can produce an at least partial increase or an at least partial decrease of an activity of a downstream protein. Any downstream protein of any target protein provided herein can be evaluated, for example downstream proteins of any proteins encoded by the genes in Table 7. In some cases, a target protein is RAF1. In some instances, a downstream protein of Raf1 can comprise MEK1/2, ERK1/2, AP-1 or any combination thereof. In some cases, a target protein comprises EGFR. In some cases, a downstream protein of EGFR can comprise NcK, PAK, PI3K, Ras or any combination thereof. In some instances, a downstream protein of EGFR can comprise a pathway such as proteins that comprise the PI3K pathway which can include PDK-1, Akt, mTOR, and S6K. Another example of a downstream protein pathway for EGFR can be the Pak pathway which can comprise NcK, MKK3/6, JNK, P38, c-Fos, and c-Jun. In some cases, a downstream protein can comprise a transcriptional regulator such as STATS.

In some cases, a peptide of salt thereof can have anti-cancer activity. Anti-cancer activity can refer to reduction or elimination of cancer. In some cases, anti-cancer activity can comprise killing of a cancer cell. Anti-cancer activity can be determined in vivo or in vitro. In some cases, a cancer cell, such as a cancer cell line can be utilized. Suitable cancer cells for use in methods provided herein can comprise in vitro cell lines or primary cancer cells. In some cases, a peptide or salt thereof can modulate an expression level of a target protein. Modulation can be determined utilizing an assay or mouse model to determine a level of killing of a cancer cell.

In some cases, provided herein can be partial increases or partial decreases of an activity of a target protein. Increases or decreases can refer to at least about a 1-fold, 2-fold, 3-fold, 4-fold, 5-fold, 6-fold, 7-fold, 8-fold, 9-fold, 10-fold, 15-fold, 20-fold, 30-fold, 50-fold, 100-fold, 150-fold, 175-fold, 200-fold, 250-fold, 300-fold, 400-fold, 500-fold, 800-fold, or up to about 1000-fold change in an activity as compared to a comparable method that lacks treatment with a peptide or salt thereof. In some cases, a partial increase or a partial decrease can refer to about: 1%, 5%, 10%, 20%, 40%, 60%, 80%, 100%, 150%, 200%, 250%, 300%, 350%, 400%, or up to about a 500% increase or decrease in an activity of a target protein. In some embodiments, a peptide or salt thereof can comprise independently Gly, or an amino acid comprising a $C_1$-$C_{10}$ alkyl, a $C_1$-$C_{10}$ alkenyl, a $C_1$-$C_{10}$ alkynyl, a cycloalkyl, or an alkylcycloalkyl side chain. In some cases, a peptide can comprise an amino acid comprising an aromatic side chain. In some cases, a peptide can comprise an amino acid comprising a side chain that can be at least partially protonated or at least partially deprotonated at a pH of about 7.3. In some cases, an amino acid of the peptide or salt thereof positioned at an end terminus comprises a side chain that can be at least partially deprotonated at a pH of about 7.3. In some cases, a peptide can comprise an amino acid comprising an amide containing side chain. In some cases, a peptide can comprise an amino acid comprising an alcohol or thiol containing side chain. In some cases, a peptide or salt thereof can comprise a recombinant peptide.

In some embodiments, a peptide can be an engineered peptide. In some cases, a peptide can be a natural peptide, a synthetic peptide, an artificial peptide, a modified peptide, or any combination thereof. In some embodiments, a peptide can comprise a chemical modification, such as an acetylation, a sulfonation, an amidation, or an esterification. In some cases, a peptide can comprise a stapled peptide or salt thereof, a stitched peptide or salt thereof, a macrocyclic peptide or salt thereof, or any combination thereof. In some instances, a stapled peptide can comprise a covalent linkage between two amino acid side-chains. In some instances, a stapled peptide can comprise an alpha-helix. A stitched peptide or salt thereof can comprise multiple staples, for example a stitched peptide can comprise a plurality of covalent linkages between different amino acid side-chains on a peptide. In some cases, a macrocyclic peptide can comprise a ring structure, or a bicyclic structure. In some instances, a macrocyclic peptide can comprise a head-to-tail, a side-chain-to-side-chain, or both, structure.

In some embodiments, a peptide provided herein can further comprise a linker. A linker can provide desirable flexibility to permit the desired expression, activity and/or conformational positioning of a peptide. A linker can be of any appropriate length and is preferably designed to be sufficiently flexible so as to allow the proper folding and/or function and/or activity of one or both of the domains it connects. In some cases, a linker can have a length of at least 3, 5, 10, 15, 20, 25, 30, 35, 40, 45, 50, 55, 60, 65, 70, 75, 80, 85, 90, 95, or 100 residues. In some embodiments, a linker has a length from about 0 to 200 residues, from about 10 to 190 residues, from about 20 to 180 residues, from about 30 to 170 residues, from about 40 to 160 residues, from about 50 to 150 residues, from about 60 to 140 residues, from about 70 to 130 residues, from about 80 to 120 residues, or from about 90 to 110 residues. In some embodiments, a linker can comprise an endogenous protein sequence. In some embodiments, a linker sequence comprises glycine, alanine, or serine amino acid residues, or any combination of glycine, alanine, and serine amino acid residues. In some embodiments, a linker can contain motifs, e.g., multiple or repeating motifs, of GS, GGS, GGGGS, GGSG, or SGGG. In some cases, a linker sequence can include any naturally occurring amino acids, non-naturally occurring amino acids, or combinations thereof. In some cases, a linker can be a cleavable linker. In some cases, a linker can at least in part be resistant to cleavage. In some cases, a resistant cleavage linker can comprise a thioether linker, a maleimide alkane linker, a maleimide cyclohexane linker, or any combination thereof. In some cases, a cleavable linker can comprise an enzymatically cleavable linker, a chemically cleavable linker, or both. A cleavable linkage can comprise an acid-labile linker, a reducible linker, a disulfide-linker, a hydrazone linker, a peptide linker, or any combination thereof. In some cases, a cleavable linker can be linked to an antibody or a fragment thereof. In some cases, a cleavable linker can be linked to a cell penetrating peptide. In some cases, a peptide can be directly or indirectly linked to a cell penetrating peptide. A cell penetrating peptide can be a short polypeptide that can allow for increased uptake of a subject composition into a cell. A cell penetrating peptide can be cationic, amphipathic, hydrophobic, and combinations thereof. In some instances, a cell penetrating peptide can comprise a TAT peptide, a MPG peptide, a Pep-1 peptide, a KALA peptide, a SV40 NLS peptide, an Arg polypeptide, a TfR targeting peptide, a rabies virus glycoprotein, or a penetratin peptide. A cell penetrating peptide can be of any length. In some cases, a cell penetrating peptide can be about 3 amino acids to about 50 amino acids long, about 5 amino acids to about 15 amino acids long, about 10 amino acids to about 25 amino acids long, about 20 amino acids to about 30 amino acids long, or about 30 amino acids to about 50 amino acids long. In some cases, a cell penetrating peptide can comprise a peptide that comprises L-amino acids, D-amino acids, both L and D amino acids, and non-natural amino acids. In some cases, a cell penetrating peptide can comprise a cyclic peptide. In some instances, a cell penetrating peptide can comprise a poly-arginine stretch.

In some embodiments, a method provided herein can be utilized for screening. In some cases, a method can be used to screen genes or proteins encoded by genes for inhibitory or stimulatory activity. In some cases, a method can comprise expressing at least a fragment of a gene in a target cell. In some embodiments, a method of screening for at least partially reducing or at least partially increasing the activity of a target protein, a protein that may interact downstream with a target protein, or both can comprise expressing one or more fragments of a gene in a target cell. In some cases, a gene fragment can be expressed from a vector, such as a polynucleotide (e.g., a plasmid) or a viral vector comprising a nucleic acid encoding the gene fragment. In some instances, a gene fragment can comprise at least a portion of a target protein. In some cases, a gene fragment can be from: about 20 nucleotides to about 1000 nucleotides, about 20 nucleotides to about 100 nucleotides, about 100 nucleotides to about 500 nucleotides, about 60 nucleotides to about 150 nucleotides, or about 500 nucleotides to about 1000 nucleotides in length. In some cases, a method of at least partially reducing the activity of a target protein or at least partially reducing the activity of a protein that interacts downstream with a target protein can comprise measuring the at least partial reduction of activity by determining a change in gene expression of a treated cell relative to the level of a gene expression in an untreated cell in an in vitro assay. In some cases, a method of screening for at least partially reducing or at least partially increasing the activity of a target protein, a protein that may interact downstream with a target protein, or both can comprise measuring the at least partial reduction of activity by determining a change in gene expression of a treated cell relative to the level of a gene expression in an untreated cell in an in vitro assay. In some cases, a change in gene expression can be determined by quantitative reverse transcriptase polymerase chain reaction, RNA-seq or both. In some instances, a target protein can be selected from a protein encoded by a gene or a variant thereof recited in Table 7. In some cases, a fragment of a gene can encode for a polypeptide comprising a sequence having at least about: 70%, 75%, 80%, 85%, 90%, 95%, 98%, or 99% sequence homology to any one of the peptides of SEQ ID Nos: 1-9489. In some cases, a vector or plasmid can be transfected, electroporated, or transduced into the target cell. In some cases, at least a portion of the target protein can comprise about: 5 amino acids to about 80 amino acids, 5 amino acids to about 20 amino acids, 10 amino acids to about 40 amino acids, 20 amino acids to about 60 amino acids, 20 amino acids to about 50 amino acids, or about 40 amino acids to about 80 amino acids. In some instances, reduction of activity can comprise reduced cell growth.

In some cases, a pharmaceutical composition can comprise a nucleic acid at least partially encoding a peptide described herein. In some cases, a nucleic acid can at least partially encode a peptide that can have at least about: 70%, 75%, 80%, 85%, 90%, 95% or 99% sequence identity to a polypeptide of SEQ ID NO: 1-9489. In some cases, the peptide may not comprise more than: about 10 amino acids to about 60 amino acids, about 10 amino acids to about 20 amino acids, about 20 amino acids to about 30 amino acids, about 30 amino acids to about 40 amino acids, about 40 amino acids to about 50 amino acids, or about 50 amino acids to about 60 amino acids. In some instances, a nucleic acid can comprise a pharmaceutical composition in unit dose form. In some cases, a nucleic acid can comprise DNA, RNA, or both. In some cases, a nucleic acid can be circular, such as a plasmid. A nucleic acid can be single stranded, double stranded, or both.

In some cases, a pharmaceutical composition can comprise a vector. A vector can comprise or can encode for a peptide described herein, for example a peptide for use in a pharmaceutical composition. In some instances, a vector can comprise a nucleic acid. In some cases, a vector can comprise a polypeptide coat. In some cases, a vector can be a viral vector, a virus-like particle. In some cases, the vector can comprise an RNA viral vector which can include but may not be limited to a retrovirus, lentivirus, coronavirus, alphavirus, flavivirus, rhabdovirus, morbillivirus, picornavirus, coxsackievirus, or picornavirus or portions of any of these, or fragments of any of these, or any combination thereof. In some cases, a vector can comprise a lentiviral vector. In some cases, a vector can comprise a DNA viral vector which can include but may not be limited to an adeno-associated viral (AAV) vector, adenovirus, hybrid adenoviral system, hepadnavirus, parvovirus, papillomavirus, polyomavirus, herpesvirus, poxvirus, a portion of any of these, or a fragment of any of these, or any combination thereof. In some cases, a vector can comprise an AAV vector. An AAV vector, can be of any serotype. In some cases, an AAV vector is of a serotype selected from any one of: AAV1, AAV2, AAV3, AAV4, AAV5, AAV6, AAV7, AAV8, AAV9, AAV10, AAV11, AAV12, AAVDJ, variants thereof, and any combination thereof. In some cases, a vector is of AAV2, AAV5, AAV9, or combinations thereof. Provided herein are also modified vectors that comprise mutations or modifications of components such as modified REP, CAP, ITRs, or combinations thereof. In some cases, chimeras of AAV vectors are also employed in methods and compositions provided herein.

Compositions provided herein can be delivered via any means. In some cases, composition is delivered via a vector. In some cases, a vector can comprise a polypeptide coat. In some cases, a vector can comprise a liposome, a nanoparticle, a microparticle, or any combination thereof. In some cases, a liposome can include but may not be limited to a unilamellar liposome, multilamellar liposome, archaeosome, noisome, novasome, cryptosome, emulsome, vesosome, or a derivative of any of these, or any combination thereof. In some cases, a vector comprises a nanoparticle. A nanoparticle, can include but may not be limited to a biopolymeric nanoparticle, an alginate nanoparticle, a xanthan gum nanoparticle, a cellulose nanoparticle, a dendrimer, a polymeric micelle, polyplexed, an inorganic nanoparticle, a nanocrystal, a metallic nanoparticle, a quantum dot, a protein nanoparticle, a polysaccharide nanoparticle, or a derivative of any of these, or any combination thereof.

Provided herein can also be a kit. A kit can comprise a pharmaceutical composition described herein, a nucleic acid described herein, a peptide described herein, a vector described herein or any combination thereof. In some cases, a kit can comprise instructions that recite the methods of using a pharmaceutical composition described herein, a nucleic acid described herein, a peptide described herein, the vector described herein or any combination thereof. In some cases, the kit can comprise instructions for administration to a subject in need thereof. In some embodiments, a kit can comprise a container, such as a plastic, a glass, or a metal container.

Also provided herein can be methods of making a pharmaceutical composition described herein. In some cases, the methods can comprise contacting a peptide or salt thereof with a pharmaceutically acceptable excipient, diluent or carrier.

In some embodiments, a pharmaceutical composition described herein can be administered in a therapeutically effective amount to a subject (e.g., a human) in need thereof to at least partially prevent or treat a disease or condition. In some cases, treating can comprise at least partially reducing or ameliorating at least one symptom of the disease or condition, such as reducing a growth of a tumor. The terms "treating," "treatment," and the like can be used herein to mean obtaining a desired pharmacologic effect, physiologic effect, or any combination thereof. In some instances, a treatment can reverse an adverse effect attributable to the disease or disorder. In some cases, the treatment can stabilize the disease or disorder. In some cases, the treatment can delay progression of the disease or disorder. In some instances, the treatment can cause regression of the disease or disorder. In some instances, the treatment can prevent the occurrence of the disease or disorder. In some embodiments, a treatment's effect can be measured. In some cases, measurements can be compared before and after administration of the composition. For example, a subject can have medical images prior to treatment compared to images after treatment to show cancer regression. In some instances, a subject can have an improved blood test result after treatment compared to a blood test before treatment. In some instances, measurements can be compared to a standard.

In some embodiments, a disease or condition can comprise cancer. In some cases, a cancer can comprise a sarcoma, a carcinoma, a melanoma, a lymphoma, a leukemia, a blastoma, a germ cell tumor, a myeloma, or any combination thereof. In some cases, cancer may comprise a thyroid cancer, adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's disease, cervical cancer, childhood Non-Hodgkin's lymphoma, lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, uterine cancer (e.g. uterine sarcoma), vaginal cancer, vulvar cancer, or Waldenstrom's macroglobulinemia.

In some cases, a cancer can include a hyperproliferative disorder. Hyperproliferative disorders can include but may not be limited to cancers, hyperplasia, or neoplasia. In some cases, the hyperproliferative cancer can be breast cancer such as a ductal carcinoma in duct tissue of a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheloid carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which may be divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which may be a skin condition that sometimes develops into squamous cell carcinoma; eye retinoblastoma; cutaneous or intraocular (eye) melanoma; primary liver cancer (cancer that begins in the liver); kidney cancer; autoimmune deficiency syndrome (AIDS)-related lymphoma such as diffuse large B-cell lymphoma, B-cell immunoblastic lymphoma and small noncleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system (CNS) cancers such as primary brain tumor, which includes gliomas (astrocytoma, anaplastic astrocytoma, or glioblastoma multiforme), oligodendrogliomas, ependymomas, meningiomas, lymphomas, schwannomas, and medulloblastomas; peripheral nervous system (PNS) cancers such as acoustic neuromas and malignant peripheral nerve sheath tumors (MPNST) including neurofibromas and schwannomas, malignant fibrous cytomas, malignant fibrous histiocytomas, malignant meningiomas, malignant mesotheliomas, and malignant mixed MUllerian tumors; oral cavity and oropharyngeal cancer such as hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer. In some cases, a cancer can comprise a malignant thyroid disorder such as for example a follicular carcinoma, a follicular variant of papillary thyroid carcinomas, a medullary carcinoma, or a papillary carcinoma.

In some cases, a disease or condition is not cancer. In some cases, a disease or condition is acute. In other cases, a disease or condition is chronic. Suitable diseases and conditions may affect adults or pediatric subjects. A disease or condition may affect the brain, eyes, lungs, liver, bladder, kidneys, heart, stomach, intestines, or combinations thereof. Non-limiting examples of diseases and conditions comprise: autoimmune, allergy, asthma, celiac, Chrohn's, colitis, heart disease, liver disease, kidney disease, lupus, rheumatoid arthritis, scleroderma, polychondritis, macular degeneration, schizophrenia, ataxia, myotonic dystrophy, Alzheimer's, Huntington's, Kennedy's, fragile X syndrome, Autism, Inflammation, ALS, drug addiction, hemophilia, thalassemia, factor X deficiency, anemia, SCID, neuropathy, cystic fibrosis, cirrhosis, osteoporosis, atrophy, diabetes, stroke, hepatitis, epilepsy, COPD, meningitis, metabolic disease, and combinations thereof.

In some embodiments, a subject may have been diagnosed with a disease or condition. In some cases, the subject may have been diagnosed prior to treating with a peptide or pharmaceutical composition thereof disclosed herein. In some cases, diagnosing a subject with a disease or condition can comprise diagnosing with a physical examination, a biopsy, a metabolite test, a radiological image, a blood test, a urine test, an antibody test, or any combination thereof. In some instances, a radiological image can comprise a computed tomography (CT) image, a nuclear scan, an X-Ray image, a magnetic resonance image (MRI), an ultrasound image, or any combination thereof.

In some embodiments, the method can comprise administering a second therapy. In some cases, a second therapy can comprise an antibiotic, an antiviral, a cancer treatment, a neurological treatment, a steroid, an anti-inflammatory treatment, or any combination thereof. In some instances, a second therapy can comprise surgery, chemotherapy, radiation therapy, immunotherapy, hormone therapy, a checkpoint inhibitor, targeted drug therapy, adoptive immunotherapy, anti-angiogenic agents, chimeric antigen receptor (CAR) T-cell therapy, gene editing therapy, a protein knockdown therapy, RNA editing therapy, or any combination thereof.

In some embodiments, a pharmaceutical composition can be in unit dose form. In some embodiments, compositions disclosed herein can be in unit dose forms or multiple-dose forms. Unit dose forms, as used herein, can refer to physically discrete units suitable for administration to human or non-human subjects (e.g., animals). In some cases, a nucleic acid or a peptide is present in a composition in a range of from about 1 mg to about 2000 mg; from about 5 mg to about 1000 mg, from about 10 mg to about 25 mg to 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg. In some cases, a dose of a composition provided herein is at least about or at most about: 10,000, 15,000, 20,000, 22,000, 24,000, 25,000, 30,000, 40,000, 50,000, 60,000, 70,000, 80,000, 90,000, 100,000, 125,000, 150,000, 200,000, or 500,000 units/kg body weight. In some embodiments, a therapeutically effective dose is at most about 10,000, 15,000, 20,000, 22,000, 24,000, 25,000, 30,000, 40,000, 50,000, 60,000, 70,000, 80,000, 90,000, 100,000, 125,000, 150,000, 200,000, or 500,000 units/kg body weight. Any one of the described dosages can be determined using the 95% CI for plasma volumes and body surface areas in males and females and an 10×IC50 (to achieve an about IC90 concentration, based on the shapes of a killing curves). In some cases, a dose range is from about 17-440 micromoles/m^2 (body surface area) per peptide. In some cases, a dosage is at least or at most about: 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, or up to about 500 micromoles/m^2 (body surface area) per peptide.

In some cases, unit dose forms can be packaged individually. Each unit dose can contain a predetermined quantity of an active ingredient(s) that can be sufficient to produce the desired therapeutic effect in association with pharmaceutical carriers, diluents, excipients, or any combination thereof. Examples of unit dose forms can include, ampules, syringes, and individually packaged tablets and capsules. In some instances, a unit dose form can be comprised in a disposable syringe. In some instances, unit-dosage forms can be administered in fractions or multiples thereof. A multiple-dose form can be a plurality of identical unit dose forms packaged in a single container, which can be administered in segregated a unit dose form. Examples of a multiple-dose form can include vials, bottles of tablets or capsules, or bottles of pints or gallons. In some instances, a multiple-dose form can comprise the same pharmaceutically active agents. In some instances, a multiple-dose form can comprise different pharmaceutically active agents.

In some embodiments, a pharmaceutical composition can comprise: a peptide or salt thereof; and at least one of: an excipient, a diluent, or a carrier.

Administration or application of a composition disclosed herein can be performed on any animal, such as a human, a non-human primate, a pet (e.g., a dog, a cat), or a farm animal (a horse, a cow, a goat, a pig). In some cases, administration or application of a composition disclosed herein can be performed on a human. In some cases, a human can be from about 1 day to about 1 month old, from about 1 month to about 12 months old, from about 1 year to about 7 years old, from about 5 years to about 25 years old, from about 20 years to about 50 years old, from about 45 years to about 80 years old, or from about 75 years to about 130 years old.

Compositions described herein can be administered before, during, or after the occurrence of a disease or condition, and the timing of administering a composition can vary. For example, a pharmaceutical compositions can be used as a prophylactic and can be administered continuously to subjects with a propensity to conditions or diseases in order to prevent the occurrence of the disease or condition. Pharmaceutical compositions can be administered to a subject during or as soon as possible after the onset of the symptoms. The administration of the molecules can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein, such as by oral administration, topical administration, intravenous administration, inhalation administration, injection, catheterization, gastrostomy tube administration, intraosseous administration, ocular administration, otic administration, transdermal administration, oral administration, rectal administration, nasal administration, intravaginal administration, intracavernous administration, transurethral administration, sublingual administration, or a combination thereof. A composition can be administered as soon as is practicable after the onset of a disease or condition is detected or suspected, and for a length of time necessary for the treatment of the disease, such as, for example, from about 1 month to about 3 months. The length of treatment can vary for each subject. In some cases, a method can further comprise administering a second therapy in a therapeutically effective amount. A second therapy can be administered concurrently or consecutively to provided compositions.

Administration or application of a composition disclosed herein can be performed for a duration of at least about at least about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 300, 400, 500, 600, 700, 800, 900, 1000 days consecutive or nonconsecutive days. In some cases, the composition can be administered for life. In some embodiments, administration or application of the composition described herein can be from about 1 to about 30 days, from about 1 to about 60 days, from about 1 to about 90 days, from about 1 to about 300 days, from about 1 to about 3000 days, from about 30 days to about 90 days, from about 60 days to about 900 days, from about 30 days to about 900 days, or from about 90 days to about 1500 days. In some embodiments, administration or application of the composition described herein can be from: about 1 week to about 5 weeks, about 1 month to about 12 months, about 1 year to about 3 years, about 2 years to about 8 years, about 3 years to about 10 years, about 10 years to about 50 years, about 15 years to about 40 years, about 25 years to about 100 years, about 30 years to about 75 years, about 60 years to about 110 years, or about 50 years to about 130 years.

Administration or application of a composition disclosed herein can be performed for a duration of at least about 1 week, at least about 1 month, at least about 1 year, at least about 2 years, at least about 3 years, at least about 4 years, at least about 5 years, at least about 6 years, at least about 7 years, at least about 8 years, at least about 9 years, at least about 10 years, at least about 15 years, at least about 20 years, or for life. Administration can be performed repeatedly over a lifetime of a subject, such as once a day, once a week, or once a month for the lifetime of a subject. Administration can be performed repeatedly over a substantial portion of a subject's life, such as once a day, once a week, or once a month for at least about: 1 year, 5 years, 10 years, 15 years, 20 years, 25 years, 30 years, or more.

Administration or application of composition disclosed herein can be performed at least about: 1, 2, 3, 4, 5, 6, 7, 8, 9, 10, 11, 12, 13, 14, 15, 16, 17, 18, 19, 20, 21, 22, 23, or 24 times a in a 24-hour period. In some cases, administration or application of a composition disclosed herein can be performed continuously throughout a 24-hour period. In some embodiments, administration or application of composition disclosed herein can be performed at least about: 1, 2, 3, 4, 5, 6, 7, 8, 9, 10, 11, 12, 13, 14, 15, 16, 17, 18, 19, 20, or 21 times a week. In some cases, administration or application of a composition disclosed herein can be performed at least about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, or more times a month. In some embodiments, a composition can be administered as a single dose or as divided doses. For example, administration of a capsule, or a tablet an comprise administration of more than one capsules or tablets. In some cases, the compositions described herein can be administered at a first time point and a second time point. In some embodiments, a composition can be administered such that a first administration can be administered before the other with a difference in administration time of about: 1 hour, 2 hours, 4 hours, 8 hours, 12 hours, 16 hours, 20 hours, 1 day, 2 days, 4 days, 7 days, 2 weeks, 4 weeks, 2 months, 3 months, 4 months, 5 months, 6 months, 7 months, 8 months, 9 months, 10 months, 11 months, 1 year or more.

Administration of a pharmaceutical composition described herein can be administered in one dose, continuously or intermittently throughout the course of treatment. Methods of determining the most effective means and dosage of administration can be determined by a physician or another medical professional and can vary with the composition used for therapy, the purpose of the therapy, and the subject being treated. For example, depending on the age and size of a subject, an appropriate dosage can be calculated. Additionally, an administration can be delivered locally or systemically depending on disease location. In some cases, compositions provided herein can be delivered via a vector or without a vector, for example as a naked composition. Single or multiple administrations can be carried out with the dose level and pattern being selected by the treating physician. Suitable dosage formulations and methods of administering the agents can be known in the art. Routes of administration can also be determined and method of determining the most effective routes of administration can be determined by a physician or another medial professional and can vary with the composition used for treatment, the purpose of the treatment, the health condition or disease stage of the subject being treated, and target cell or tissue. Non-limiting examples of routes of administration include oral administration, nasal administration, injection, and topical application.

Administration can refer to methods that can be used to enable the delivery of a pharmaceutical composition described herein (e.g. a peptide) to the desired site of biological action. For example, a nucleic acid encoding for a peptide described herein can be comprised in a viral vector and can be administered by intravenous administration. Administration disclosed herein to an area in need of treatment or therapy can be achieved by, for example, and not by way of limitation, oral administration, topical administration, intravenous administration, inhalation administration, or any combination thereof. In some embodiments, delivery can include injection, catheterization, gastrostomy tube administration, intraosseous administration, ocular administration, otic administration, transdermal administration, oral administration, rectal administration, nasal administration, intravaginal administration, intracavernous administration, transurethral administration, sublingual administration, or a combination thereof. Delivery can include direct application to the affected tissue or region of the body. In some cases, topical administration can comprise administering a lotion, a solution, an emulsion, a cream, a balm, an oil, a paste, a stick, an aerosol, a foam, a jelly, a foam, a mask, a pad, a powder, a solid, a tincture, a butter, a patch, a gel, a spray, a drip, a liquid formulation, an ointment to an external surface of a surface, such as a skin. Delivery can include a parenchymal injection, an intra-thecal injection, an intraventricular injection, or an intra-cisternal injection. A composition provided herein can be administered by any method. A method of administration can be by intraarterial injection, intracisternal injection, intramuscular injection, intraparenchymal injection, intraperitoneal injection, intraspinal injection, intrathecal injection, intravenous injection, intraventricular injection, stereotactic injection, subcutaneous injection, epidural, or any combination thereof. Delivery can include parenteral administration (including intravenous, subcutaneous, intrathecal, intraperitoneal, intramuscular, intravascular or infusion administration). In some cases, delivery can be from a device. In some instances, delivery can be administered by a pump, an infusion pump, or a combination thereof. In some embodiments, delivery can be by an enema, an eye drop, a nasal spray, or any combination thereof. In some instances, a subject can administer the composition in the absence of supervision. In some instances, a subject can administer the composition under the supervision of a medical professional (e.g., a physician, nurse, physician's assistant, orderly, hospice worker, etc.). In some embodiments, a medical professional can administer the composition.

In some cases, administering can be oral ingestion. In some cases, delivery can be a capsule or a tablet. Oral ingestion delivery can comprise a tea, an elixir, a food, a drink, a beverage, a syrup, a liquid, a gel, a capsule, a tablet, an oil, a tincture, or any combination thereof. In some embodiments, a food can be a medical food. In some instances, a capsule can comprise hydroxymethylcellulose. In some embodiments, a capsule can comprise a gelatin, hydroxypropylmethyl cellulose, pullulan, or any combination thereof. In some cases, capsules can comprise a coating, for example, an enteric coating. In some embodiments, a capsule can comprise a vegetarian product or a vegan product such as a hypromellose capsule. In some embodiments, delivery can comprise inhalation by an inhaler, a diffuser, a nebulizer, a vaporizer, or a combination thereof.

The following examples are intended to illustrate but not limit the disclosure. While they are typical of those that might be used, other procedures known to those skilled in the art may alternatively be used.

EXAMPLES

Design of Gene Fragment Libraries. Gene fragments from target genes were composed of the DNA coding sequence for all 40 mer amino acids from the genes listed in FIGS. 1B, 6 and 7. The 5' and 3' ends of each gene fragment were modified to contain a start and stop codon, as well as ~20 bp of DNA homologous to the expression plasmid for downstream Gibson cloning. For cell surface expression constructs start and stop codons were excluded.

Gene Fragment Cloning. Gene fragment libraries were synthesized as pooled single stranded oligonucleotides by Custom Array. These oligonucleotides were then PCR amplified using KAPA-HiFi (Kapa Biosystems) to generate double stranded gene fragments compatible with Gibson cloning. 50 μl PCR reactions were set up with 25 ng of pooled oligonucleotide template and 2.5 μl of primers PEP_1 and PEP_2 (10 μM). The thermal cycler was programmed to run at 95 C for 30 seconds, followed by 12 cycles of 98 C for 15 seconds, 65 C for 15 seconds, and 72 C for 45 seconds. This was followed by a final 5-minute extension at 72 C. PCR products were then purified using the QIAquick PCR purification kit. See Table 4 for primer sequences.

The gene fragment overexpression vector pEPIP was generated from a modified pEGIP (Addgene #26777). The vector was modified to remove the GFP insert, insert an EcoRI cloning site, and add primer binding regions with which to amplify the libraries for HTS. To clone the gene fragment libraries into the appropriate expression vector, pEPIP was first digested with EcoRI (NEB) for 3 hours at 37C. The linearized vectors were then column purified using the QIAquick PCR purification kit. Subsequently, Gibson assembly was used to clone the gene fragment libraries into the pEPIP vector. For each reaction, 10 μl of Gibson Reaction MasterMix (NEB) was combined with 100 ng of the vector and 50 ng of the double stranded gene fragment library, with H20 up to 20 μl. The Gibson reactions were then incubated at 50C for 1 hr and transformed via electroporation into 200 μl of ElectroMAX Stb14 competent cells (Invitrogen) according to the manufacturer's protocol. The Stb14 cells were then resuspended in 4 mL of SOC media and placed at 37C with shaking for 1 hr to recover. After recovering, 1 μl of the SOC/cell suspension was spread on LB-carbenicillin plates to calculate library coverage, with the remaining SOC/cells used to inoculate a 100 ml culture of LB-carbenicillin. Greater than 2000 fold library coverage was obtained to ensure all gene fragments were well represented. After 16 hours of incubation at 37C with shaking, plasmid DNA was isolated via a Qiagen Plasmid Plus Maxi Kit.

TABLE 4

Primers:

| Name | Description | Sequence |
|---|---|---|
| PEP_01 | Used to amplify initial oligo pool and individually synthesized cancer driver gene fragments for cloning | GGCTAGGTAAGCTTGATATCG GCCACCATG (SEQ ID NO: 9512) |
| PEP_02 | Used to amplify initial oligo pool and individually synthesized cancer driver gene fragments for cloning | GGCGGCACTGTTTAACAAGCC CGTCAGTAG (SEQ ID NO: 9513) |
| PEP_03 | Used to amplify cancer driver gene fragments for high throughput sequencing | ACACTCTTTCCCTACACGACG CTCTTCCGATCTGCTTGATAT CGGCCACCATG (SEQ ID NO: 9514) |
| PEP_04 | Used to amplify cancer driver gene fragments for high throughput sequencing | GACTGGAGTTCAGACGTGTGC TCTTCCGATCTCACTGTTTAA CAAGCCCGTCAGTAG (SEQ ID NO: 9515) |
| PEP_05 | Used to amplify Betacoronavirus receptor oligo pools and individually synthesized gene fragments for cloning | TGACGGTTCTGGGAGCGGTTC T(SEQ ID NO: 9516) |
| PEP_06 | Used to amplify Betacoronavirus receptor oligo pools and individually synthesized gene fragments for cloning | GTTCGCTGCCGGACCCACTTC C (SEQ ID NO: 9517) |
| PEP_07 | Used to amplify Betacoronavirus receptor gene fragments for high throughput sequencing | ACACTCTTTCCCTACACGACG CTCTTCCGATCTTGACGGTTC TGGGAGCGGTTCT (SEQ ID NO: 9518) |

TABLE 4-continued

| Primers: | | |
|---|---|---|
| Name | Description | Sequence |
| PEP_08 | Used to amplify Betacoronavirus receptor gene fragments for high throughput sequencing | GACTGGAGTTCAGACGTGTGC TCTTCCGATCTGTTCGCTGCC GGACCCACTTCC (SEQ ID NO: 9519) |
| EF1a_seq | Used for Sanger sequencing of constructs cloned into peptide expression vectors | TTCTCAAGCCTCAGACAGTGG (SEQ ID NO: 9520) |

Lentivirus Production. Replication deficient lentiviral particles were produced in HEK293FT cells (Invitrogen) via transient transfection. HEK293FT cells were grown in DMEM media (Gibco) supplemented with 10% FBS (Gibco). The day before transfection, HEK293FT cells were seeded in a 15 cm dish at ~40% confluency. The day of transfection, the culture media was changed to fresh DMEM plus 10% FBS. At the same time, 3 ml of Optimem reduced serum media (Life Technologies) was mixed with 36 μl of lipofectamine 2000, 3 μg of pMD2. G plasmid (Addgene #12259), 12 μg of pCMV deltaR8.2 plasmid (Addgene #12263), and 9 μg of the gene fragment plasmid library. After 30 minutes of incubation, the plasmid/lipofectamine mixture was added dropwise to theHEK293FT cells. Supernatant containing viral particles was harvested 48 and 72 hours after transfection and concentrated to 1 ml using Amicon Ultra-15 centrifugal filters with a cutoff 100,000 NMWL (Millipore). The viral particles were then aliquoted and frozen at −80C until further use.

Fitness Screening in Mammalian Cell Lines. Hs578T cells and MDA-MB-231 cells were cultured in DMEM media supplemented with 10% FBS. Cells were transduced with the gene fragment library at an MOI<0.3 to ensure each cell received a single construct. Viral transduction was performed in media containing 8 μg/ml polybrene to improve transduction efficiency. For each cell line, screening was conducted with two biological replicates. 48 hours after transduction, the cell culture media was changed to DMEM containing puromycin to select for transduced cells. 2 μg/ml puromycin was used to select the Hs578T cells, and 3.5 μg/ml puromycin was used to select the MDA-MB-231 cells. For both cell lines, more than 6,000,000 cells were transduced to ensure greater than 1000-fold coverage of the library. The cells were cultured for 14 days after transduction, with genomic DNA isolated via a Qiagen DNeasy Blood and Tissue Kit at days 3 and 14.

HTS Library Preparation and Sequencing. Gene fragments for each time point and replicate were then amplified from the genomic DNA using Kapa HiFi. The fragments serve as their own barcodes for downstream abundance calculations. Illumina compatible libraries were prepared using 2.5 μl of primers PEP_3 and PEP_4 (10 μM) per 50 μl reaction. For each sample 10 separate 50 μl PCR reactions with 4 μg of gDNA each (40 μg total) were performed to ensure adequate library coverage. Thermal cycling parameters were identical to those used to amplify the gene fragment oligos, with the exception that the gDNA required 26 cycles to amplify. NEBNext Multiplexed Oligos for Illumina (NEB) were used to index the samples, and 150 bp single end reads were then generated via an Illumina HiSeq2500. Greater than 500-fold sequencing depth was used to ensure accurate abundance quantitation. For the larger libraries, the number of PCR reactions was scaled to process 300 μg of total gDNA per timepoint and replicate. The larger libraries were then sequenced with 100 bp paired end reads generated via an Illumina HiSeq4000.

Processing of sequencing files. To quantify gene fragment relative abundance, the library definition text file (containing gene fragment names and sequences) was first converted into Fasta format. This Fasta file was then used to build a Bowtie2 index file. Raw FASTQ reads were then mapped to the library index file via Bowtie2. For the expanded libraries paired end reads were first merged into a single FASTQ file via FLASH (Fast Length Adjustment of SHort reads). Reads with insertion or deletion mutations were removed to eliminate spurious data resulting from out of frame gene fragments. The resulting SAM files were then compressed to BAM files via SAMtools. Following this, the count module in MAGeCK was used to determine the gene fragment abundances from the alignment files and indivisual peptide log fold change and depletion P-values.

Calculation of Amino Acid Level Depletion Scores. After generating the gene fragment count files, all downstream analysis was performed in R. For each amino acid residue in the overall protein structure, an amino acid level log fold change was calculated by taking the mean log 2 fold change of all overlapping gene fragments for each replicate. The geometric mean of the biological replicates was then used for downstream analysis. For every residue in the protein scaffolds, this mean log 2 fold change (x) was then converted to a z-score (z), normalizing to the library wide amino acid log 2 fold change standard deviation (δ) and mean (μ)

$$\text{Fitness Score} = Z = \frac{x - \mu}{\sigma}$$

To identify amino acid positions which were significantly depleted, a one tailed permutation test was performed. The approximate permutation distribution of amino acid fitness scores was generated by randomly shuffling the labels of all gene fragments in the screen. This shuffled data was subsequently used to recalculate the amino acid fitness scores. This resampling procedure was then repeated N=10,000 times, with the P values for each amino acid position calculated by the following:

$$P = \frac{\sum_{i=1}^{N} (Fitness_{Perm} < Fitness_{Obs})}{N \text{ permutations}}$$

These P values were then adjusted for multiple comparison testing by the Benjamini-Hochberg procedure. The R packages “ggplot2”, “dplyr”, and “zoo” were used to generate figures. An analogous procedure was used to identify enriched domains (and corresponding enrichment scores) when screening coronavirus receptor peptides for binding to the spike protein/RBD.

Validating Highly Depleted Gene Fragments. All cell lines used were cultured in DMEM media supplemented with 10% FBS. The fitness impact of highly depleted gene fragments was tested in an arrayed format via a WST-8 (Dojindo) cell growth assay. Highly depleted gene fragments were synthesized by Twist Biosciences, cloned directly into the pEPIP vector, and subsequently packaged into lentiviral particles. Cells were transduced at an MOI of 4 and switched to puromycin containing media after 48 hours. Following 24 hours of puromycin selection 1,500 cells were seeded per well as biological replicates in a 96 well plate. All experimental groups for Hs578T cells had n=4. For MDA-MB-231 cells, all experimental groups had n=4, with the exception of the GFP control which had n=8. For HEK293T and MCF-7 cells all experimental groups had n=8. 2 μg/ml puromycin was used to select Hs578T and MCF-7 cells, while 3.5 μg/ml puromycin was used to select MDA-MB-231 and HEK293T cells. For the second panel of experiments (DICER1-552, etc.) all experimental groups had n=6. Cell growth was then quantified via absorbance at 450 nm following 1.5 hrs of incubation with WST-8 reagent. A two-tailed P value was then calculated via an unpaired ttest with Welch's correction.

Engineering Peptides for Exogenous Delivery. Peptides shown in FIG. 3B were fused to an N-terminal cell penetrating motif via a (GS)3 linker sequence (Table 5) and chemically synthesized by GenScript's Custom Peptide Synthesis service at crude purity. For dose response experiments, cells were plated in 96 well plates (n=4) at 50% confluency and peptides were added at the indicated concentrations with cell viability quantified after 24 hrs via the WST-8 assay. Cell viability was normalized to that of an untreated control on the same plate.

TABLE 5

| Name | Amino Acid Sequence |
|---|---|
| TAT-EGFR-697 | GRKKRRQRRRPPQGSGSGSMEA PNQALLRILKETEFKKIKVLGS GAFGTVYKGLWIPEGE (SEQ ID NO: 9521) |
| TAT-RAF1-73 | GRKKRRQRRRPPQGSGSGSMRN GMSLHDCLMKALKVRGLQPECC AVFRLLHEHKGKKARL (SEQ ID NO: 9522) |
| TAT-RAF1-78 | GRKKRRQRRRPPQGSGSGSMLH DCLMKALKVRGLQPECCAVFRL LHEHKGKKARLDWNTD (SEQ ID NO: 9701) |
| TAT-FLAG | GRKKRRQRRRPPQGSGSGSDYK DHDGDYKDHDIDYKDDDDK (SEQ ID NO: 9522) |

Co-Immunoprecipitation. HEK293T cells were seeded in 6 well plates to be 75% confluent on the day of transfection. Transfections were performed with 1 μg of each indicated plasmid per well with 5 μl of Lipofectamine 2000 according to the manufacturers protocol. 48 hours after transfection, cells were washed twice with ice cold PBS and lysed for 30 minutes in ice cold 400 μl TBS buffer containing 0.5% Triton x-100, 1 mM EDTA, and Halt Protease Inhibitor Cocktail (Thermo Fisher 78429). The supernatant was then clarified by centrifugation at 14,000 G for 15 minutes. Following this, immunoprecipitation of FLAG tagged constructs was performed by adding 300 μl of the lysate to 20 μl of packed anti FLAG agarose beads (Millipore Sigma A2220) prewashed with TBS. The remaining 100 μl of lysate was stored at −80C for later analysis. The bead-lysate mixture was then mixed end over end at 4C for 2 hours. After binding to the beads, the bead-protein complexes were washed three times with 1 ml lysis buffer and eluted with 20 μl of 2×SDS-PAGE Laemmli loading buffer (BioRad 1610737).

Western Blotting. Proteins were first separated on 4-20% polyacrylamide gels (BioRad 4561094) under denaturing conditions in Tris-Glycine-SDS (BioRad 1610732) for 1 hour at 100V. Following this, proteins were transferred to 0.2 μm nitrocellulose membranes (BioRad 1620112) for 30 minutes at 100V in Tris-Glycine buffer (BioRad 1610734) containing 30% methanol. Membranes were then blocked for 1 hour in TBS-T (Cell Signaling 9997) containing 5% non-fat dry milk (BioRad 1706404XTU). Primary antibodies were then added (diluted 1:1000 in TBS-T+ 5% milk) and incubated overnight at 4C with gentle agitation. The following day the membranes were washed three times in TBS-T and incubated for 1 hour with HRP conjugated secondary antibodies (diluted 1:10,000 in TBS-T) at room temp. The membranes were then washed again three times with TBS-T and developed using SuperSignal West Pico Plus Chemiluminescent Substrate (Thermo Fisher 34577).

Immunofluorescence. Cells were plated the day before transduction at approximately 20% confluency. On the day of transduction, cells were transduced with the appropriate lentiviral constructs at an MOI of 1 and allowed to grow for 72 hours. Following this, the cells were washed twice with PBS and fixed for 30 minutes at room temperature with 4% paraformaldehyde. Cells were then washed three times with PBS and blocked for 1 hour at room temp with TBS plus 5% Sea Block (Thermo Fisher PI37527X3) and 0.2% Triton x-100. The blocking buffer was then aspirated and replaced with blocking buffer plus anti-FLAG primary antibody at a 1:500 dilution. The primary antibody was then allowed to bind overnight at 4C. The following day, the cells were washed three times with PBS, and incubated for 1 hour with a secondary anti-mouse IgG antibody conjugated to DyLight 488 (diluted 1:200). The cells were then washed three times with PBS and subsequently imaged via fluorescence microscopy.

RNA-Seq of Highly Depleted Fragments. RNA sequencing was performed on Hs578T cells 6 days after transduction with lentivirus expressing gene fragments of interest. Two biological replicates were sequenced for each experimental condition. Total RNA was isolated from cells via an RNEasy Kit (Qiagen) with on column DNAse I treatment. An NEBNext Poly(A) mRNA Magnetic Isolation Module (E7490S) was then used to deplete rRNA. Subsequently, an NEBNext Ultra RNA Library Prep Kit (E7530S) was used to generate Illumina compatible RNA sequencing libraries. Sequencing was performed on an Illumina HiSeq4000, with paired end 100 bp reads. Reads were aligned to the human reference transcriptome via the STAR aligner, and differential gene expression was performed using DESeq2. Differential expression was tested in reference to a control group transduced with lentivirus coding for GFP. Following this, the R package "fgsea" was used to conduct GSEA pre-ranked analysis. Genes were ranked via the shrunken log fold change values outputted by DESeq2.

Network Visualization. Network of protein-protein interactions was generated using publicly available data from STRING. Edges were drawn for all interactions with a confidence score greater than 0.98, taking into account all interaction sources available. Node color was based on fitness scores for each gene available via DepMap CRISPR knockout screening. The CERES normalized gene effects were used to quantify the fitness impact of a given knockout. Visualization was then performed in CytoScape.

Self-Surface Peptide Cloning. The cell surface peptide expression vector (pEsPIP) was generated from a modified pEGIP (Addgene #26777). The vector was modified to remove the GFP insert, and insert a cloning site flanked by an in-frame Ig Kappa leader sequence and PDGFR transmembrane domain to ensure proper localization of peptides. Cell surface peptide libraries were amplified with PEP_5 and PEP_6 and cloned via Gibson Assembly into pEsPIP as described above.

Screening for Betacoronavirus Binders using Magnetic Cell Isolation. Preparation of lentivirus and transduction of NIH-3T3 cells was performed as above, with care taken to ensure 1,000 fold library coverage during transduction. 48 hours after transduction, cells were selected with 3 μg/ml of puromycin. 72 hours after transduction, cells were incubated for 30 minutes on ice with 25 μg/mL of the appropriate mouse Fc tagged Betacoronavirus protein (Sino Biological 40592-V05H and 40591-V05H1) and subsequently washed once with PBS to remove free protein. Cells were then incubated with anti-mouse Fc magnetic beads for 15 minutes (Miltenyi 130-048-401), washed again with PBS and subjected to magnetic activated cell sorting according to the manufacturers protocol. The bound fraction was subsequently washed thrice and then eluted. Genomic DNA was then extracted and sequencing libraries generated as above (using primers PEP_7/8).

Recombinant Peptide Production. Recombinant production protocol was adapted from (Tropea et al., 2009). Recombinant MBP fusions and TEV protease were cloned into the pET Champion vector (Thermo K630203) and expressed in T7 express *E. coli* (NEB C2566I). Constructs were ordered as gBlocks from IDT and cloned directly into the vector via Gibson Assembly. To produce high yield MBP-peptide fusions and TEV protease, a 10 mL starter culture of *E. coli* was grown for 14 hours at 37C in TB media. This starter culture was then used to induce a 1L culture of TB media. This culture was grown at 37C until an OD of 0.8, and then induced with 0.5 mM IPTG. The cells were subsequently grown overnight at 25C, following which the cells were pelleted and stored at −20C. To isolate recombinant proteins, cells were first lysed via mechanical disruption with mortar and pestle in liquid nitrogen and resuspended in binding buffer (50 mL 50 mM sodium phosphate, 200 mM NaCl, 10% glycerol, and 25 mM imidazole at pH 8.0). Cell lysate was then clarified via centrifugation for 30 minutes at 20,000 g. Following this, the soluble fraction of the lysate was applied via gravity flow to 5 mL of a pre-equilibrated Ni-NTA resin (Thermo 88221). The resin was subsequently washed with 15 column volumes of binding buffer, and eluted with 50 mM sodium phosphate, 200 mM NaCl, 10% glycerol and 250 mM imidazole at pH 8.0. Purified TEV protease and the MBP-peptide fusions were subsequently dialyzed into cleavage buffer (50 mM sodium phosphate, 200 mM NaCl, pH 7.4) using Amicon 3 kD MWCO centrifugal spin filters (Millipore UFC800324). Cleavage reactions were set up in cleavage buffer containing 2 mg/mL MBP-peptide fusion, 0.2 mg/mL TEV protease, and 1 mM DTT (added fresh). This reaction was allowed to proceed overnight at 25C. The following day, the cleavage reaction was diluted 1:8 with binding buffer and applied over a pre-equilibrated Ni-NTA resin to remove the TEV protease and MBP proteins (1 mL resin per 5 mg fusion protein). The flow through (containing purified peptide) was subsequently dialyzed into PBS and concentrated to 5 mg/mL.

Engineering Peptides for Exogenous Delivery. Peptides shown in FIG. 2D were fused to an N-terminal cell penetrating motif via a (GS)3 linker sequence and chemically synthesized by GenScript's Custom Peptide Synthesis service at crude purity. For dose response experiments, cells were plated in 96 well plates (n=4) at 50% confluency and peptides were added at the indicated concentrations with cell viability quantified after 24 hrs via the WST-8 assay. Cell viability was normalized to that of an untreated control on the same plate.

Figure 1B:
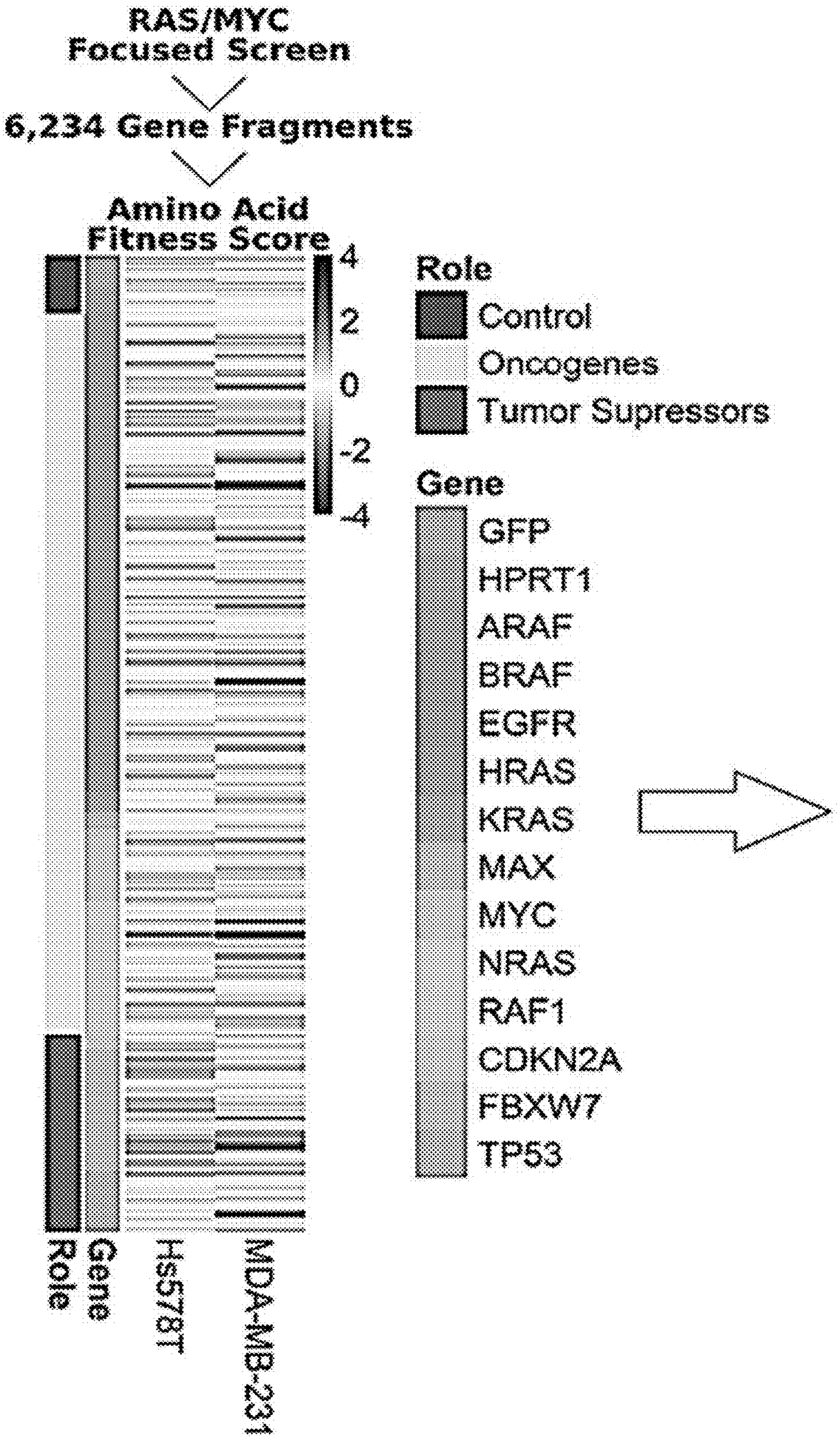
Figure 1B:
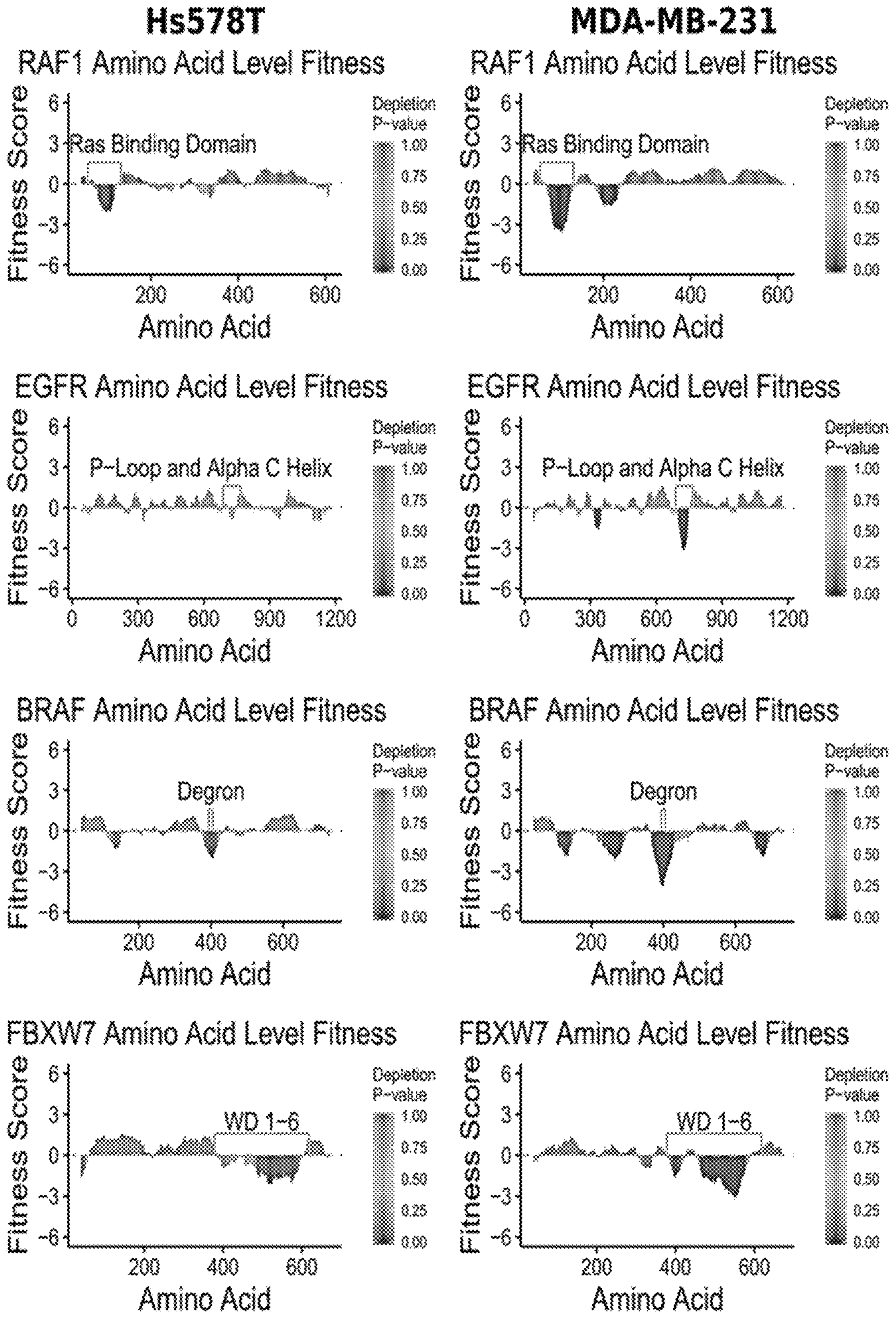

Using the screening methods described herein a pilot peptide library was generated. Lentiviral libraries of synthetic gene fragments comprehensively tiling intracellular (cancer driver genes) and extracellular (receptors of Betacoronaviruses) proteins that serve as drivers of pathological processes was developed. Towards the former, a pilot peptide library of oncogenes and associated effectors from the RAS and MYC signaling pathways were synthesized (FIG. 1A-B). RAS and MYC are two of the most frequently mutated/amplified oncogenes across a wide variety of malignancies, highlighting the medical need to identify functional inhibitors. Compounding this, RAS and MYC have proven challenging to drug via small molecules, due to their lack of a binding pocket and reliance on PPIs for signal transduction. Owing to their larger size and ability to form complex folded structures, it was surmised peptide biologics are likely suited to disrupting the protein-protein interactions through which RAS and MYC mediate cellular proliferation.

Figure 3A:
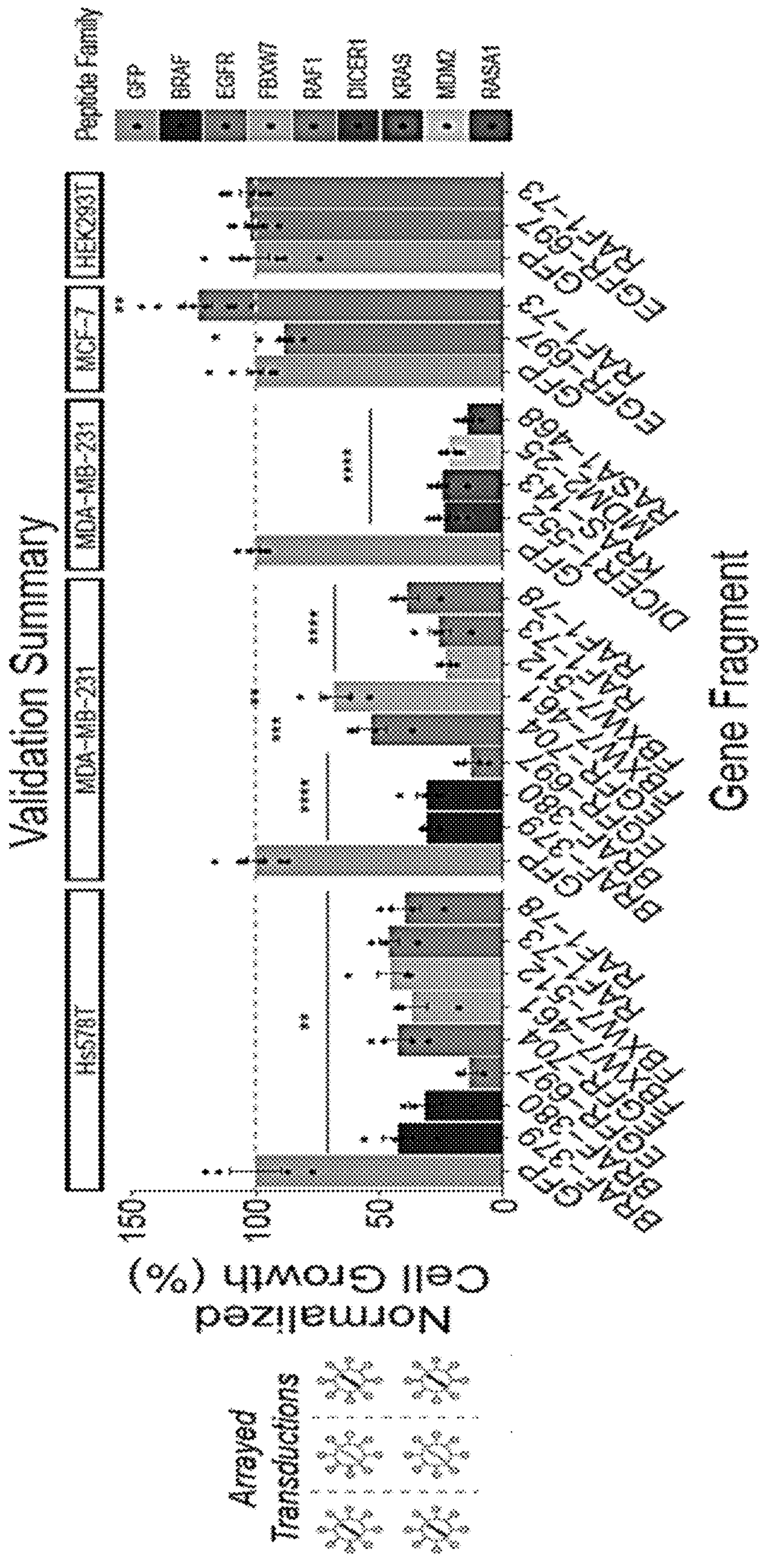
FIG. 3A-D shows validation of anti-proliferative peptides confirms target specific functionality: (A) In vitro arrayed validation of lentivirus delivered gene fragments derived from WT proteins. Peptides predicted to be deleterious to cell growth (by depletion in pooled screen) significantly inhibited proliferation relative to GFP control. Cell proliferation was measured via the WST-8 assay after one week of growth following lentiviral transduction. Bar plots indicate mean, with error bars representing standard error (*P<0.05, P<0.01,*P<0.001,****P<0.0001). Each panel represents a separately conducted experiment (hence the two MDA-MB-231 panels). (B) Validation with chemically synthesized peptides (n=4). Chemically synthesized EGFR-697 and RAF1-73 conjugated to a cell penetrating TAT protein transduction motif were added to cells at 0-100 μM. A 3×FLAG Peptide conjugated to TAT served as the negative control. Cell viability was measured 24 hours later by the WST-8 assay, indicating EGFR-697 and RAF1-73 function effectively in vitro to inhibit the growth of Hs578T and MDA-MB-231 cells in a dose dependent manner. Dotted lines indicate 95% confidence intervals for nonlinear fit. (C) Peptide mechanism explored via co-immunoprecipitation. 3×-Flag tagged RAF1-73 derived from the Ras binding domain of RAF1 pulls down activated Ras when immunoprecipitated, indicating retention of WT domain biological functionality. (D) Results of RNA-sequencing on EGFR-697 expressing Hs578T cells. EGFR-697 overexpression results in significant growth arrest, and differential expression of 225 genes, as well as significant downregulation of pathways relevant to cellular proliferation. Additional GSEA analysis revealed a transcriptional phenotype consistent with EGFR inhibition. Gene set "KOBAYASHI_EGFR_SIGNALING_24 HRS_DN" is a gene set composed of genes downregulated upon treatment with an irreversible EGFR inhibitor in H1975 cells. Treatment with EGFR-697 peptide results in significant downregulation of this gene set in Hs578T cells. The "KOBAYASHI_EGFR_SIGNALING_24 HRS_UP" is a gene set from the same experiment highlighting genes which are upregulated upon EGFR inhibition. This gene set is significantly upregulated upon EGFR-697 overexpression.

For every target protein in the library, gene fragments were synthesized via oligonucleotide pools coding for every possible overlapping 40 mer peptide within the proteins primary structure. Testing every overlapping 40 mer improves statistical power and allows for sensitive discrimination of similar peptide motifs, minimizing the required downstream optimization of inhibitors. To maximize the chance of identifying a peptide inhibitor of RAS or MYC signaling, gene fragments derived from the downstream RAS effectors ARAF, BRAF, and RAF1, were included as well as the negative regulator of MYC stability FBXW7. FBXW7 was of interest due to its role in regulating the degradation of several other key oncogenes. In addition to gene fragments derived from the wild-type RAS and MYC proteins, fragments derived from pathogenic Ras variants that have been shown to have unique protein-protein interaction networks were also included. Furthermore, gene fragments derived from EGFR (due to its role in oncogenic signal transduction to Ras proteins), from the HRAS S17N dominant negative, and the MYC dominant negative Omomyc were also included. As negative controls fragments derived from the green fluorescent protein (GFP) and hypoxanthine (-guanine) phosphoribosyltransferase (HPRT1) were used. Finally, two canonical tumor suppressor genes TP53 and CDKN2A were used. After removing duplicates, the final library consisted of 6234 unique gene fragments, spanning 14 full length genes. The pooled library of gene fragments was then synthesized as single stranded oligonucleotides and cloned into a lentiviral vector, with an EF1a promoter driving gene fragment transcription (FIG. 1A, 3A). An internal ribosomal entry site (IRES) was placed after the gene fragment stop codon to allow for co-translation of a puromycin acetyltransferase gene. This allowed for selection of transduced cells via the addition of puromycin to the cell culture media.

Figure 3B:
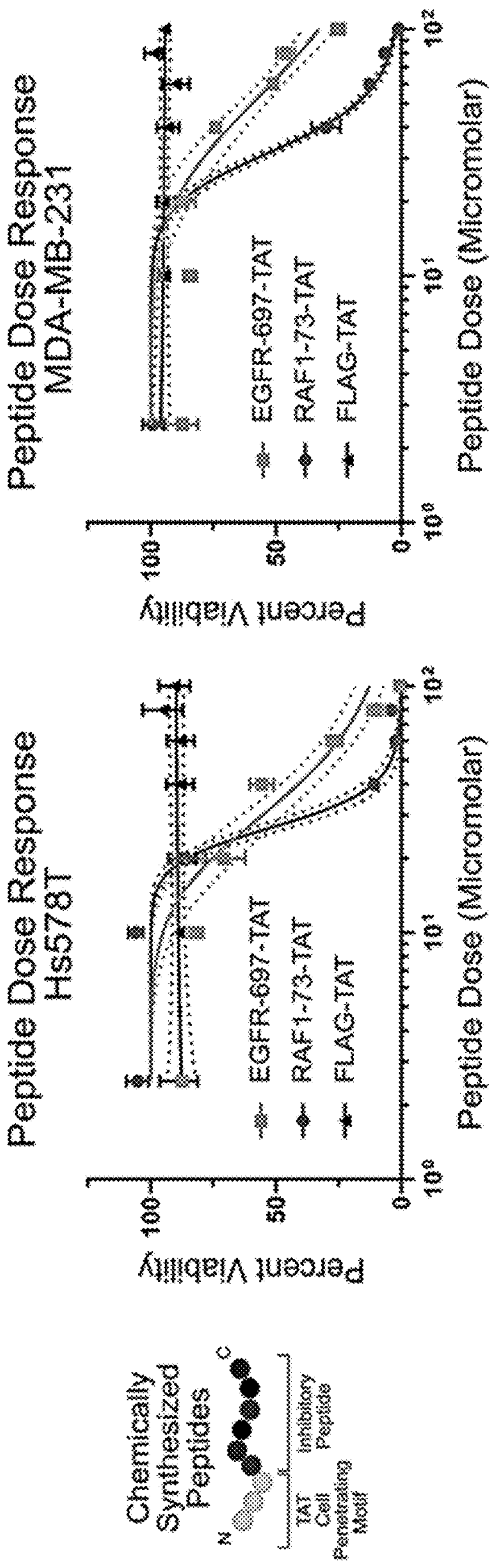

The library was then packaged into lentiviral particles which were used to transduce Hs578T and MDA-MB-231 cells in duplicate (FIG. 1A). Genomic DNA was isolated three days after transduction, as well as 14 days after transduction to calculate fragment specific log 2 fold changes. These gene fragment specific log 2 fold change values were then used to calculate an amino acid level fitness score via the mean of all fragments which overlap a particular codon (FIG. 1A-B, 3B). This score serves as a metric with which to reduce noise between closely related peptides, as well as a way to map the results back to the original protein structure. Based on this, 2.9% (Hs578T) and 10.5% (MDA-MB-231) of residues tested had significantly depleted overlapping peptides, indicating peptides derived from these positions were collectively more deleterious to cell fitness than a random sampling of peptides from the library (FIG. 3B). There was good correlation between biological replicates, with the Hs578T and MDA-MB-231 amino acid scores having a Pearson correlation of 0.54 and 0.75, respectively.

In order to visualize protein motifs with a significant impact of cell fitness, the amino acid scores were superimposed along the primary amino acid sequence for each associated protein (FIG. 1B). EGFR, BRAF, FBXW7 and RAF1 all had significant regions of significant depletion in one of the cell lines tested, corresponding to previously annotated protein function. Peptides derived from the P-loop and Alpha C-Helix of EGFR were depleted across both cell lines, likely due to the role of the P-loop in ATP binding, as well as the conformationally sensitive role the auto-inhibitory C-Helix plays in regulating EGFR enzymatic activity. Supporting a functional role for this depleted EGFR domain, this region of the EGFR gene (Exon 19) is frequently deleted in cancer, comprising approximately 44% of activating EGFR mutations seen clinically. The Ras Binding Domain (RBD) of RAF1 was also significantly depleted across both cell lines, presumably due to the blocking of Ras-Raf interactions by titrating out the binding site on endogenous RAF1 proteins. FBXW7 had a broad region of depletion corresponding to WD repeats 1-6. Knock-out screening via CRISPR-Cas9 has shown FBXW7 is not essential in Hs578T or MDA-MB-231 cells, meaning it is unlikely that this depletion is due to direct inhibition of FBXW731. The WD repeats in FBXW7 mediate substrate binding and subsequent recruitment to the E3 ubiquitin-protein ligase complex, suggesting the highly depleted peptides may retain the ability of the full length protein to bind oncogenes such as MYC38. BRAF had several significantly depleted regions dispersed across the primary sequence including one corresponding to a previously identified phospho-degron motif centered on amino acids 394-405.

Figure 1C:
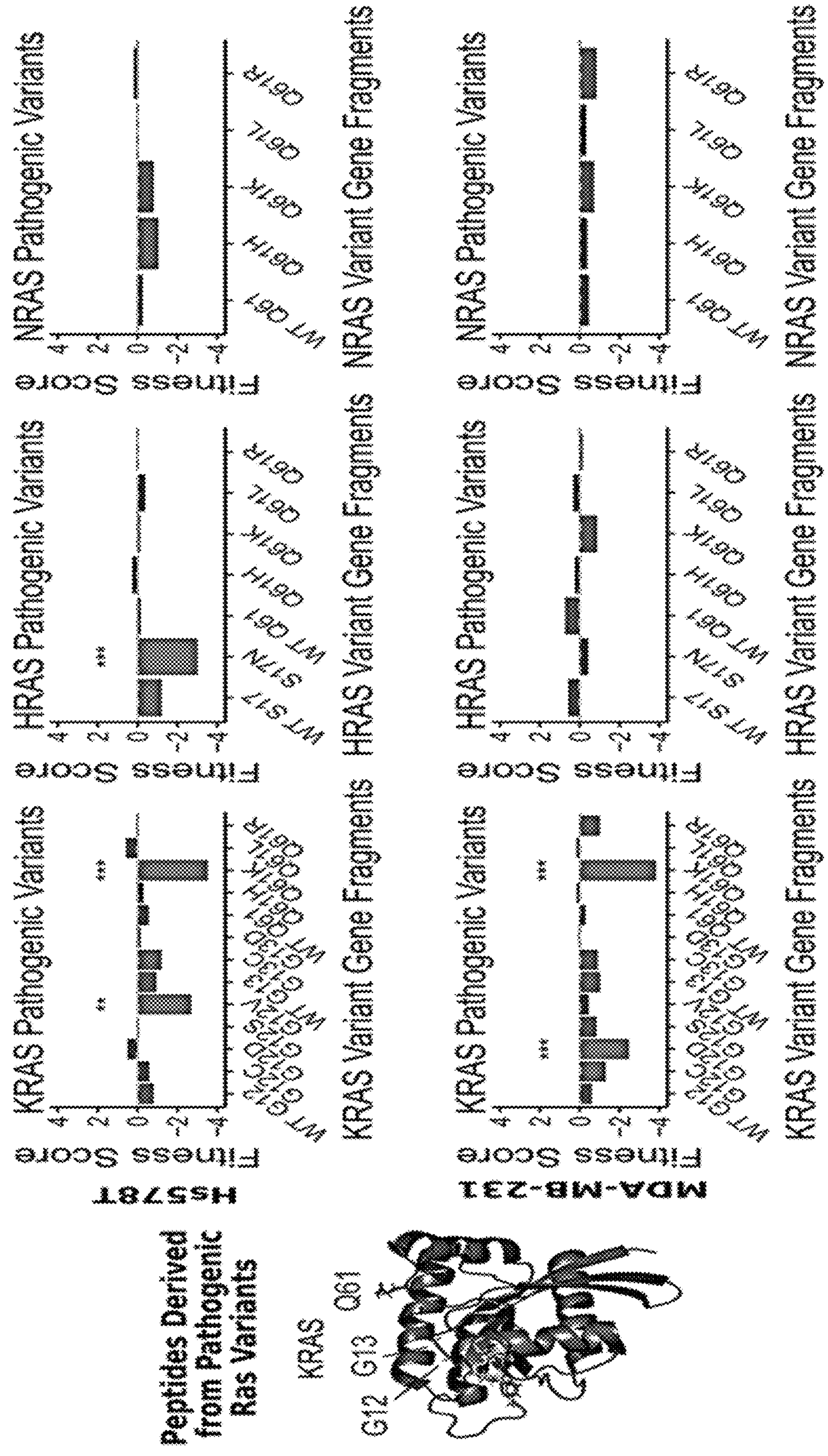

Towards the broader goal of identifying highly specific inhibitors of KRAS function, peptides derived from pathogenic variants were tested to see if they could function as more effective dominant negative proteins (FIG. 1C). Interestingly, the 40 mer peptides derived from KRAS Q61K (see, e.g., SEQ ID NO:9602 and fragments SEQ ID NOs: 4161-4168 as well as SEQ ID NOs:962-1052, 2704-2721, 3186-3198, 6708-6805) were significantly depleted across both cell lines, while wild type peptides overlapping amino acid showed no effect on cell fitness. The full length Q61K mutant is highly transforming due to a modified Ras/Raf interaction. This may play a role in the anti-proliferative activity of the Q61K derived fragments (e.g., SEQ ID NOs:4161-4168). Furthermore, peptides derived from the known HRAS S17N dominant negative mutant showed selective depletion only in the mutant HRAS driven Hs578T cell line, highlighting the ability of this technology to discriminate fitness dependencies with high specificity.

Figure 2A:
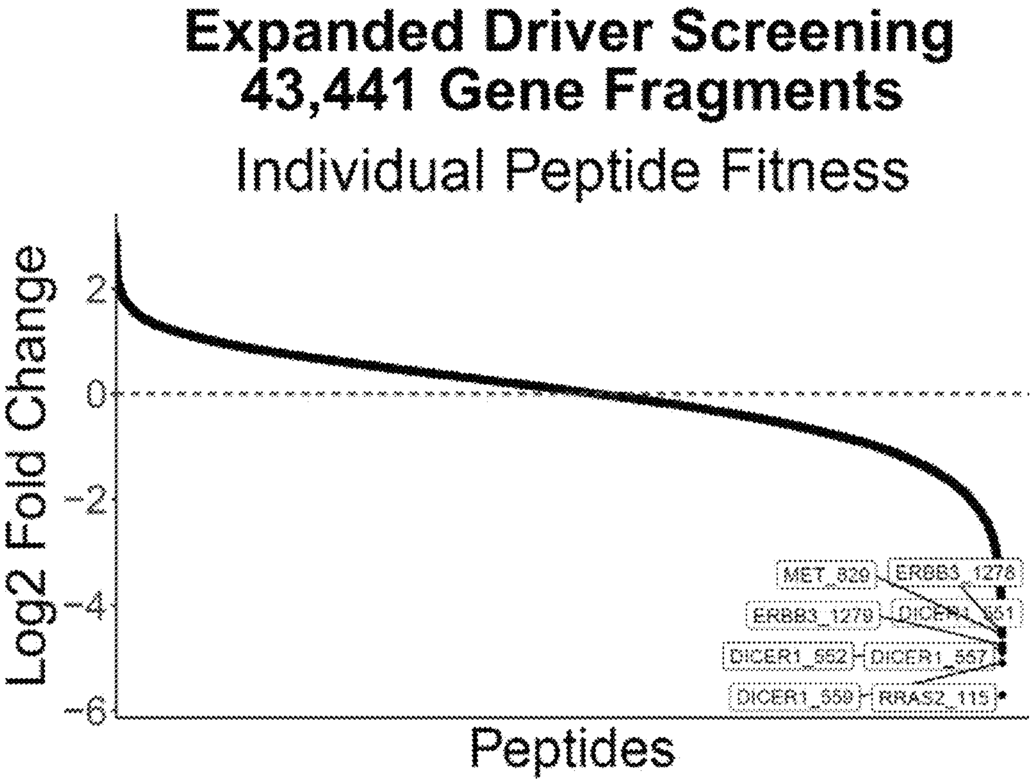
FIG. 2A-F shows gene fragment screening identifies motifs which function as inhibitors of cancer cell proliferation: (A) Plot of individual peptide enrichment/depletion for expanded screen. Peptides are centered around zero depletion, with a subpopulation being significantly deleterious to cells when overexpressed genetically. Peptides with $\log_2$ fold change values less than −4.5 are labeled. Cancer driver genes were hand curated, with additional controls added from the pilot screen. (B) Plot of individual peptide enrichment/depletion for mutant screen. 579 mutant cancer drivers covering 53 driver genes were assayed for growth inhibition as in (A). Peptides are centered around zero depletion, with a subpopulation being significantly deleterious to cells when overexpressed genetically. Peptides with $\log_2$ fold change values less than −7 are labeled. (C) Per position fitness scores for NFE2L2, MDM2, and PIK3CA. Select known PPIs are annotated on the plots, corresponding to regions of significant depletion. (D) Network of potential interactions among cancer drivers in this gene set. Interaction data is sourced from STRING, with fitness data from DepMap CRISPR screening overlaid. Nodes colored in light gray are essential for cell fitness, while nodes colored in dark gray are non-essential or have increased growth rates upon knockout. Arrows highlighting potential disruption of oncogenic PPIs. Gray nodes indicate genes for which high confidence CRISPR based fitness data was not available. (E) Fitness scores for mutant residues derived from KRAS. Functional regions sourced from UniProt are overlaid above WT fitness. Dots indicate mutant amino acid fitness scores which were significantly depleted during the pooled screen (F) Comparison of mutant fitness scores derived from peptide screening data, with fitness scores derived from deep mutational scan data in a TP53 null cell line. After filtering out TP53 mutants with little effect on cell fitness in the deep mutational scan (absolute fitness scores <0.5), inferred TP53 functionality is significantly correlated with mutant peptide derived fitness (Pearson, P=0.045), supporting the hypothesis that peptide screening can be used to identify functionally important residues in the context of cancer cell fitness.

In order to mine potentially translatable dominant negative peptide motifs in a more systematic fashion a library of 43,441 peptides was synthesized (FIG. 2A SEQ ID NOs:1-9459) derived from key oncogenic driver genes with a high prevalence in TCGA sequencing data. This library covers ~20% of all high confidence cancer drivers identified in a recent computational approach, allowing for a more comprehensive characterization of potential oncogene derived dominant negative inhibitors of proliferation. This expanded screen identified many peptides with fitness defects (as measured by log fold depletion) an order of magnitude greater than those identified in the smaller pilot screen (FIG. 2A).

Figure 2B:
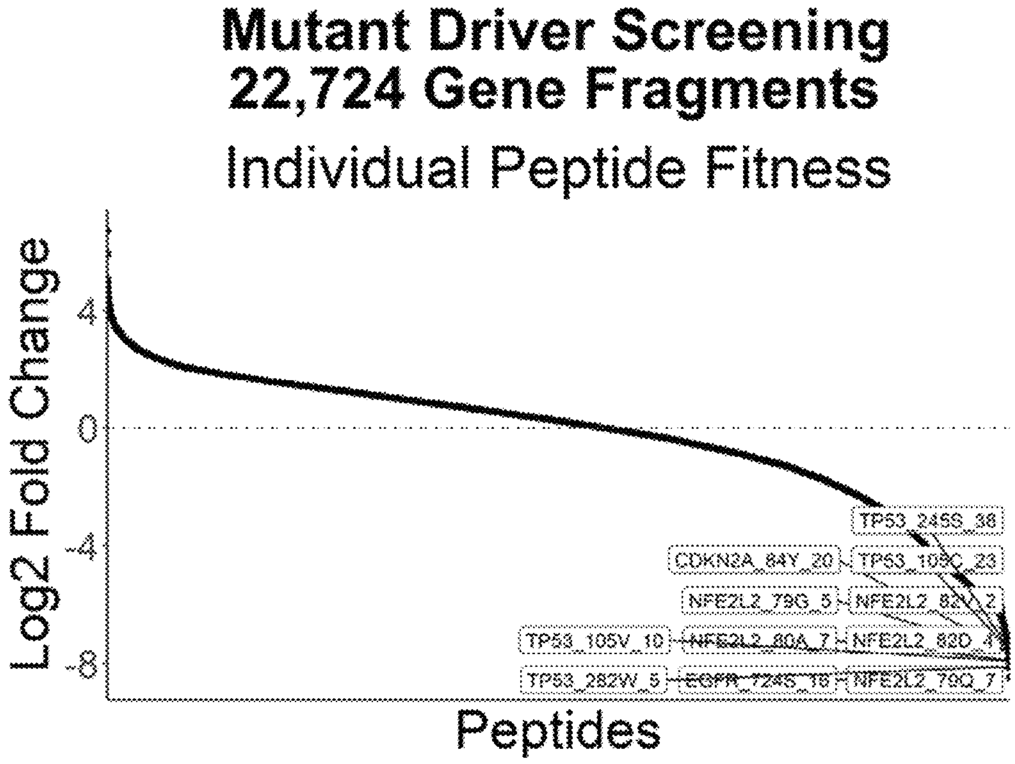
Figure 2C:
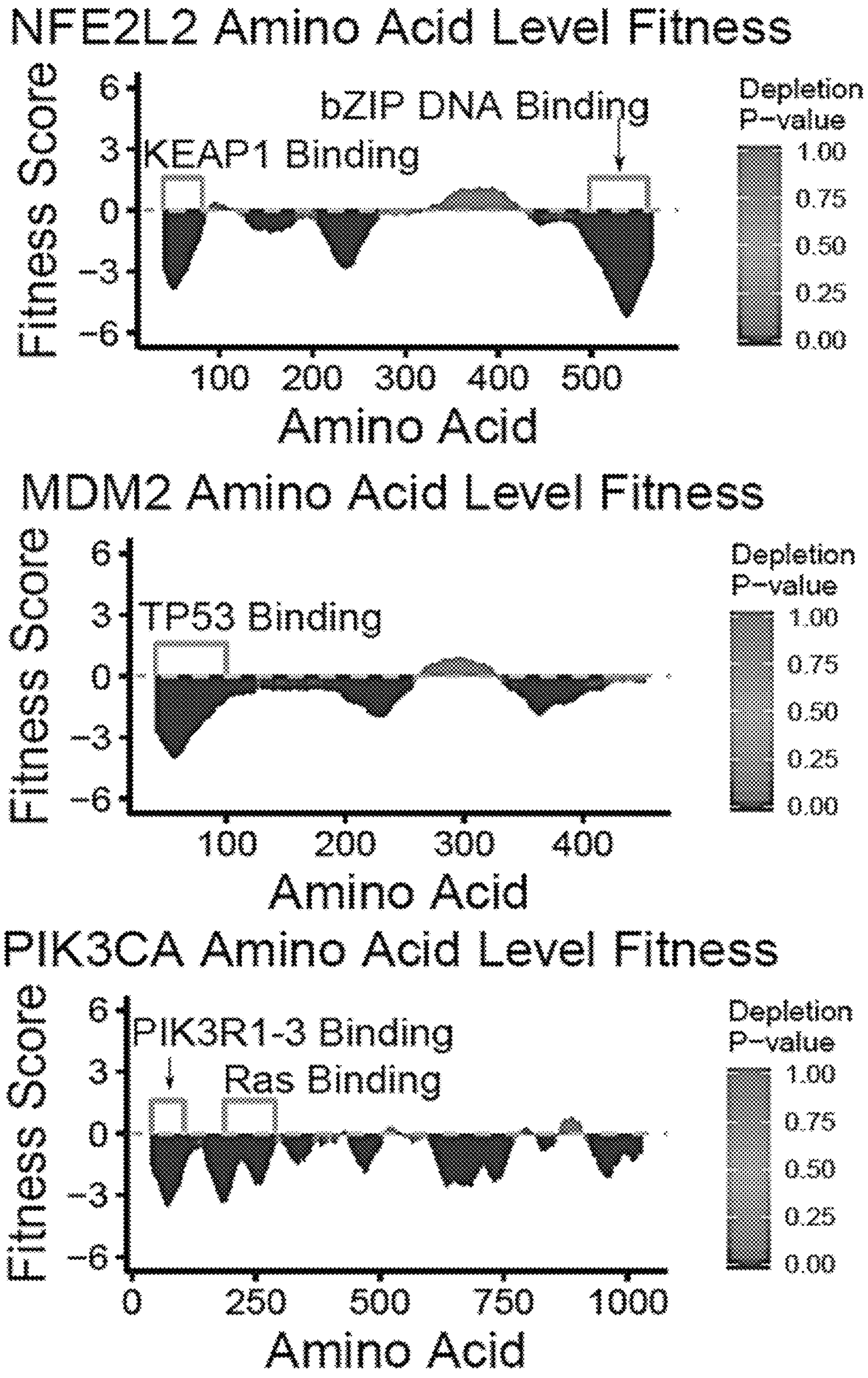

Peptides were also mapped from the library back to the WT protein's primary structure to visualize domains with a significant impact on cell fitness (FIG. 2C). First, the pattern of depletion for the transcription factor NFE2L2, the protein containing the most deleterious domains as scored by this screen, was examined. Peptides derived from the DNA binding domain, as well as the KEAP1 binding domain of NFE2L2 were highly depleted in the screen, consistent with the critical role these regions play in mediating NFE2L2 function. NFE2L2 has been previously shown to support cellular proliferation and metastasis in MDA-MB-231 cells, supporting the conclusion that a peptide inhibitor of NFE2L2 could be used to inhibit cell growth. The fitness of peptides derived from MDM2 were also examined. MDM2 is a negative regulator of TP53 function in the cell, and inhibition of the MDM2-TP53 PPI has been shown to effectively oppose cancer growth across a variety of malignancies. In the screening data, peptides derived from the TP53 binding domain of MDM2 were significantly depleted consistent with previous reports that truncated MDM2 proteins containing only the N-terminus function as dominant negatives. The PI3K-AKT-mTOR pathway is one of the most frequently dysregulated pathways in cancer, and PIK3CA plays a pivotal role in signal transduction along this pathway. The most critical region impacting cell fitness in PIK3CA corresponds to the adaptor binding domain of the protein. PIK3CA activity is modulated by the binding of various adaptor proteins encoded by genes such as PIK3R1, PIK3R2 and PIK3R3. Supporting the hypothesis that these peptides potentially inhibit proliferation via disruption of the PIK3CA/PIK3R1-3 complex, the corresponding PIK3CA binding domain in PIK3R1 is also depleted. The depleted domains for DICER1 were also plotted. Regions corresponding to binding sites for known DICER1 cofactors TARBP and PRKRA were heavily depleted, comprising some of the most deleterious peptides in the screen. This data supports the growing understanding of the oncogenic role miRNAs and other epigenetic regulators play in tumorigenesis. Surprisingly, the tumor suppressor RB1 contained domains which were highly deleterious to cell fitness. The N-terminal RbN domains were both highly depleted, potentially due to previously described allosteric interactions with the cell cycle regulatory transcription factor E2F49. ERBB4 had a pattern of depletion similar to EGFR, with overexpression of peptides derived from the ERBB4 regulatory P-loop and Alpha C-helix resulting in a significant fitness defect, highlighting the importance of this region in ERBB dimerization and proliferative signaling. Peptides from this screen were analyzed for their impact on cancer driver specific signaling networks (FIG. 2D) using publicly available PPI data from STRING, with nodes colored by gene fitness data sourced from DepMap CRISPR knockout screening. Notably, using this data, peptide motifs were identified that interfere with important PPI interfaces mediating signal transduction between cancer drivers previously identified as essential for cell fitness.

Figure 2D:
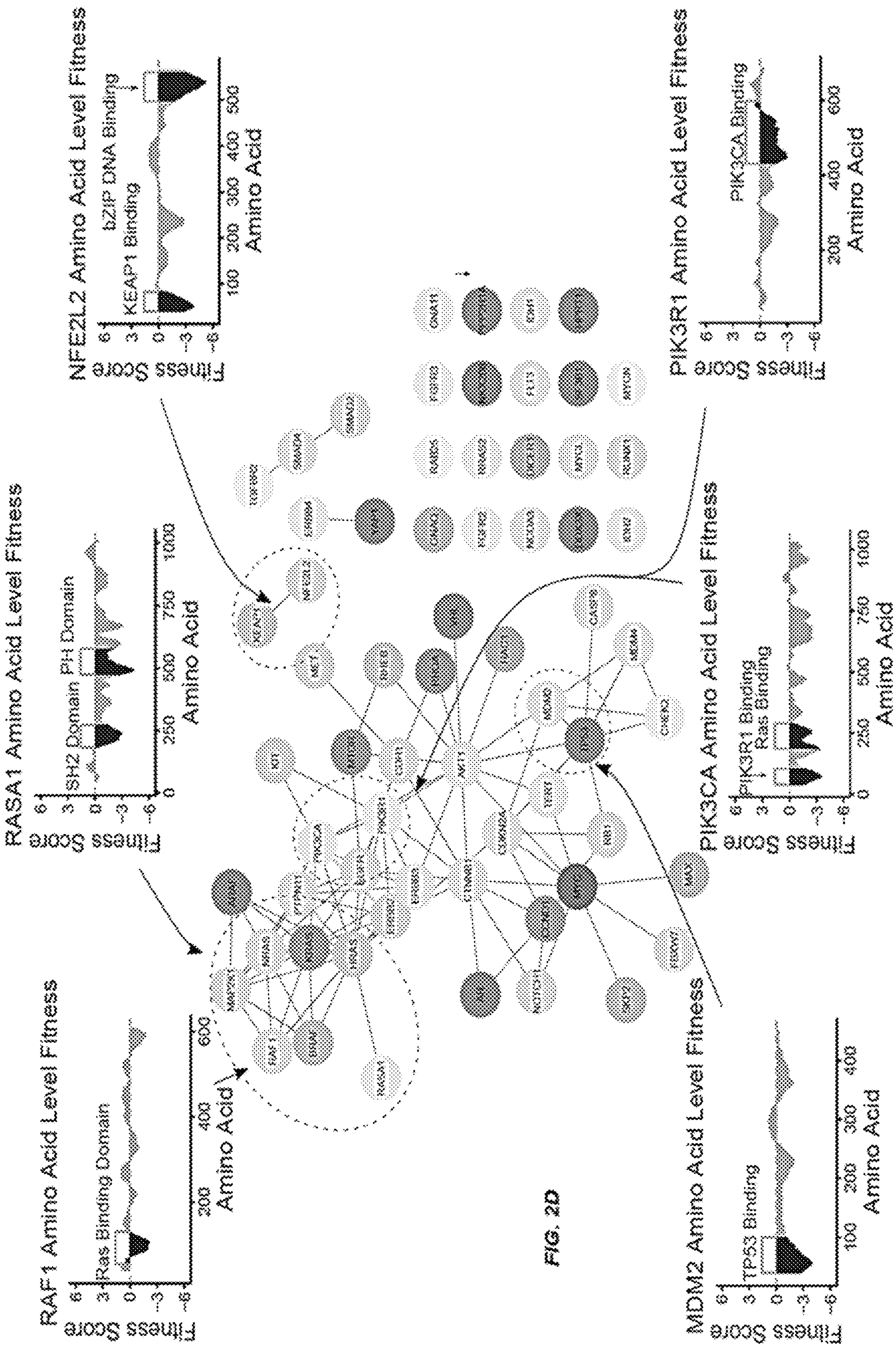
Figure 2E:
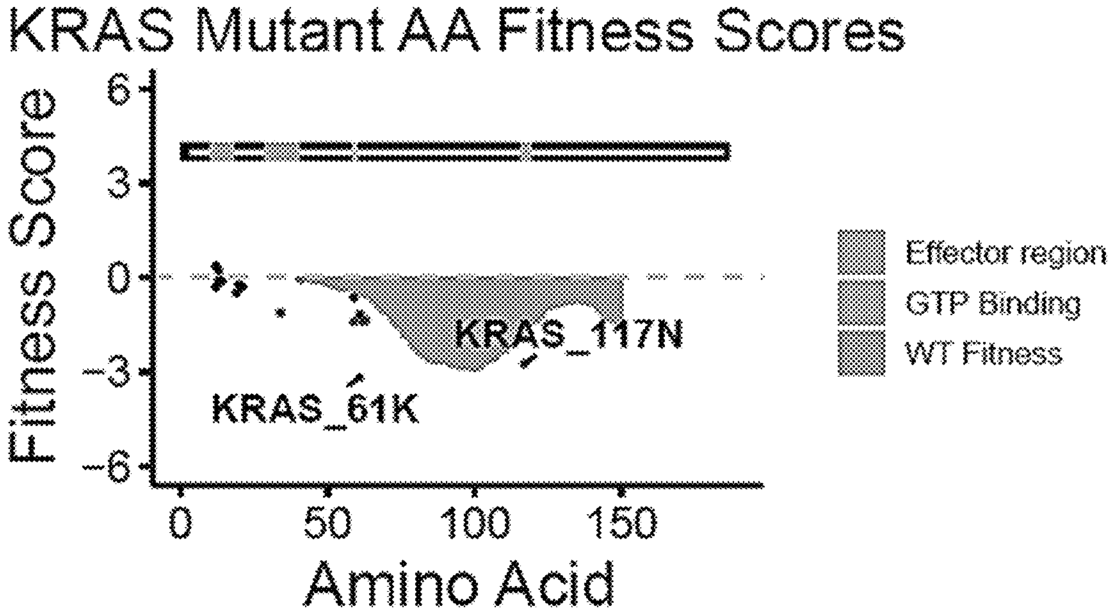
Figure 2F:
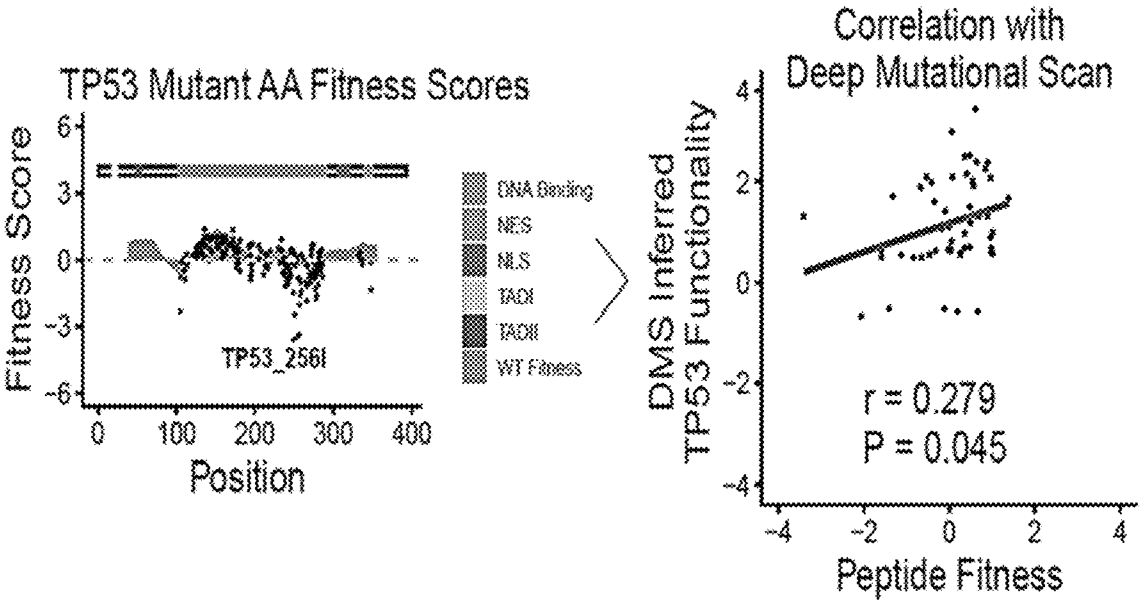
Figure 6B:
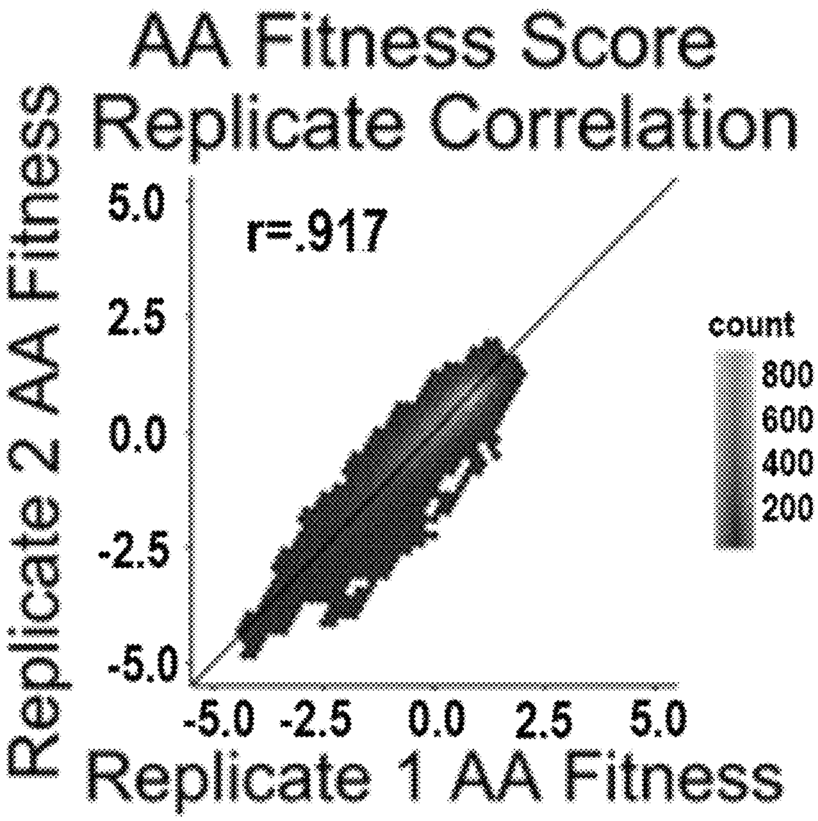
Figure 6C:
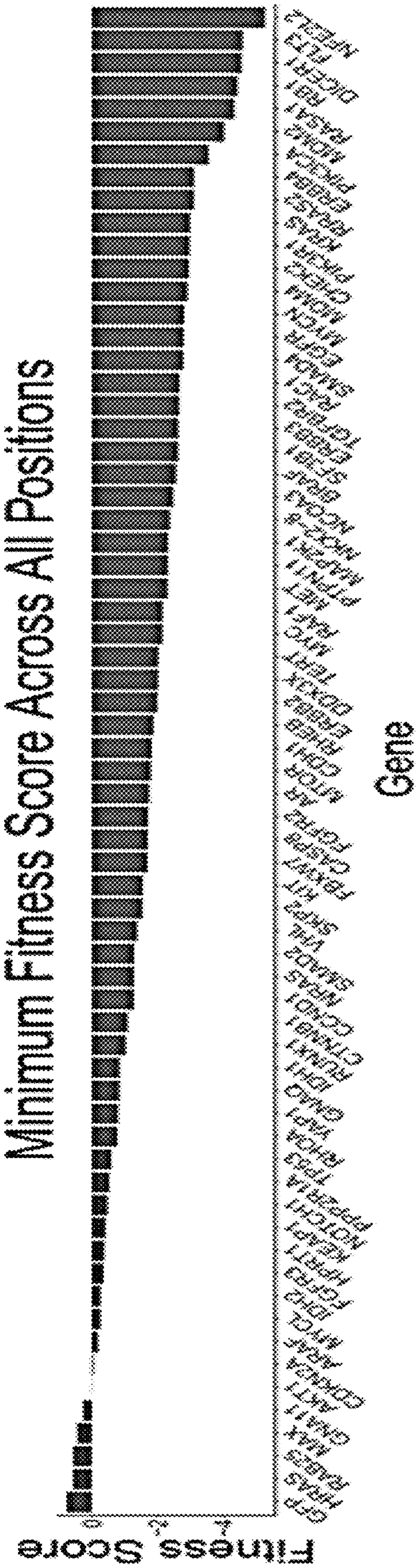
Figure 6D:
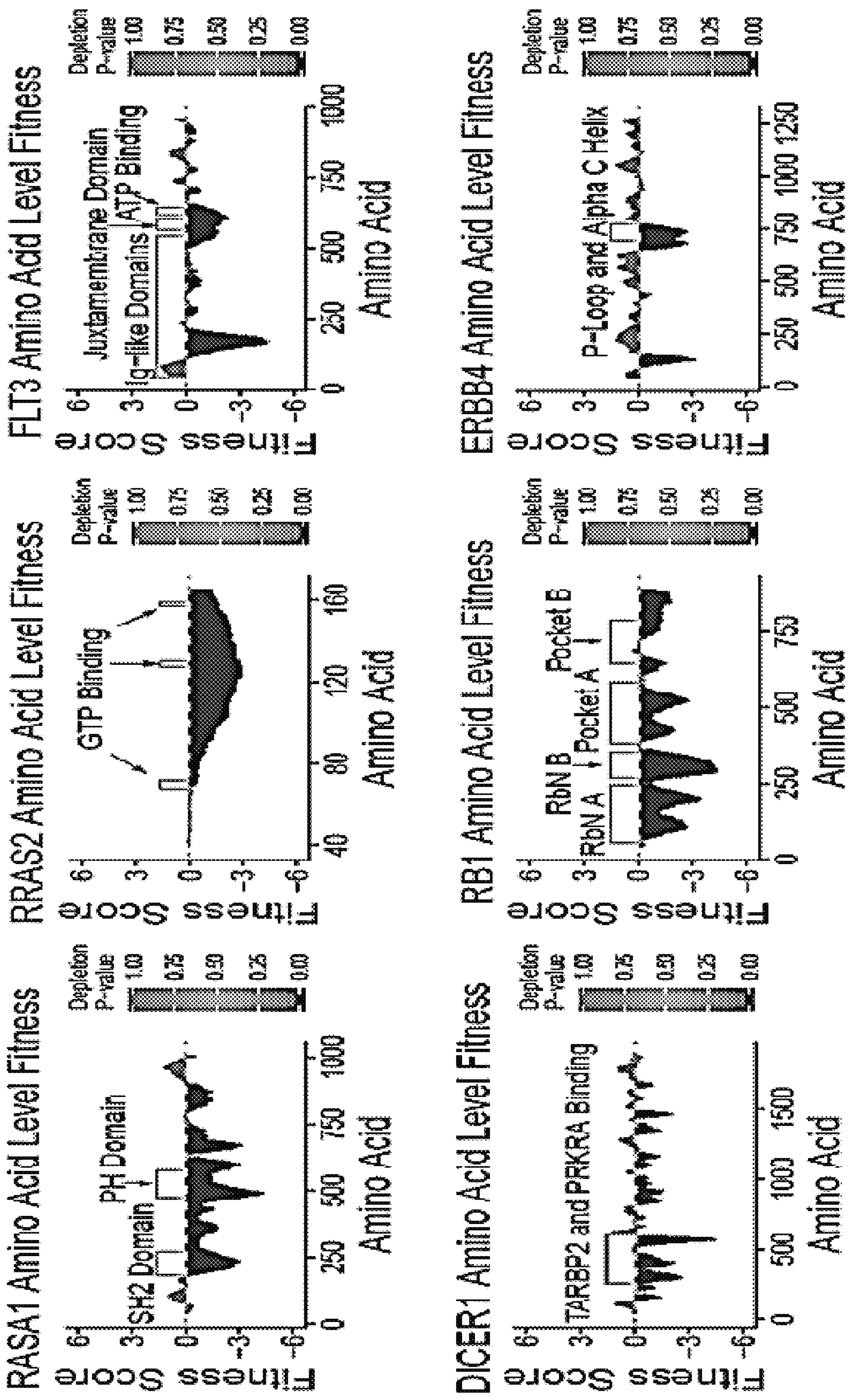
Figure 6F:
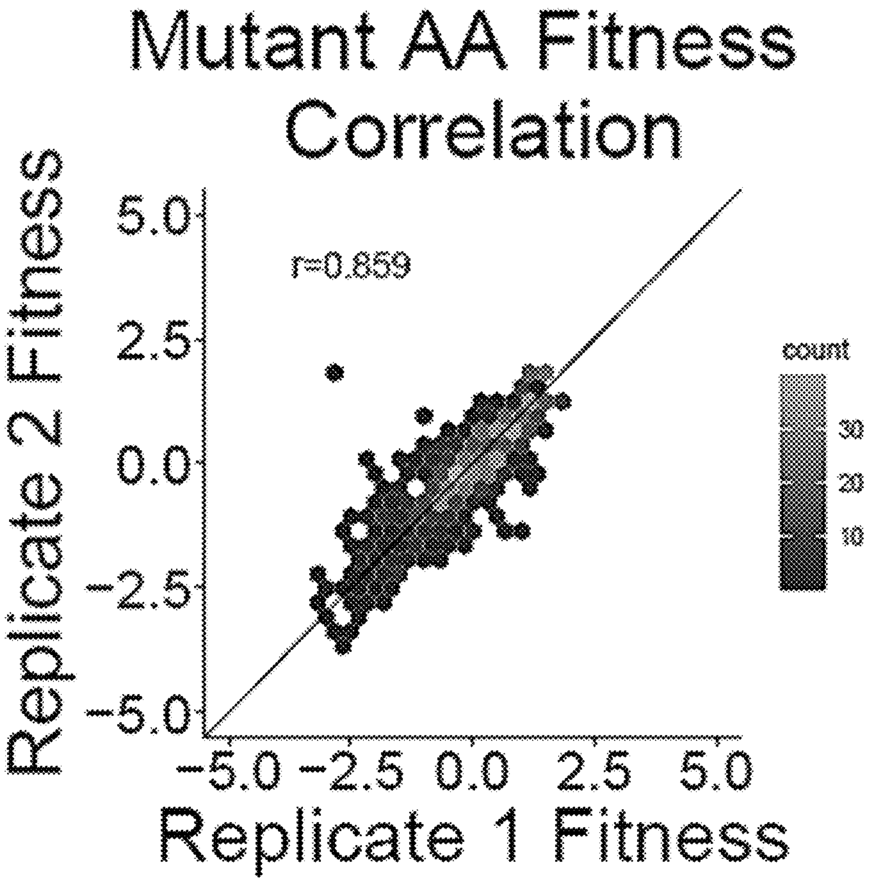
Figure 6G:
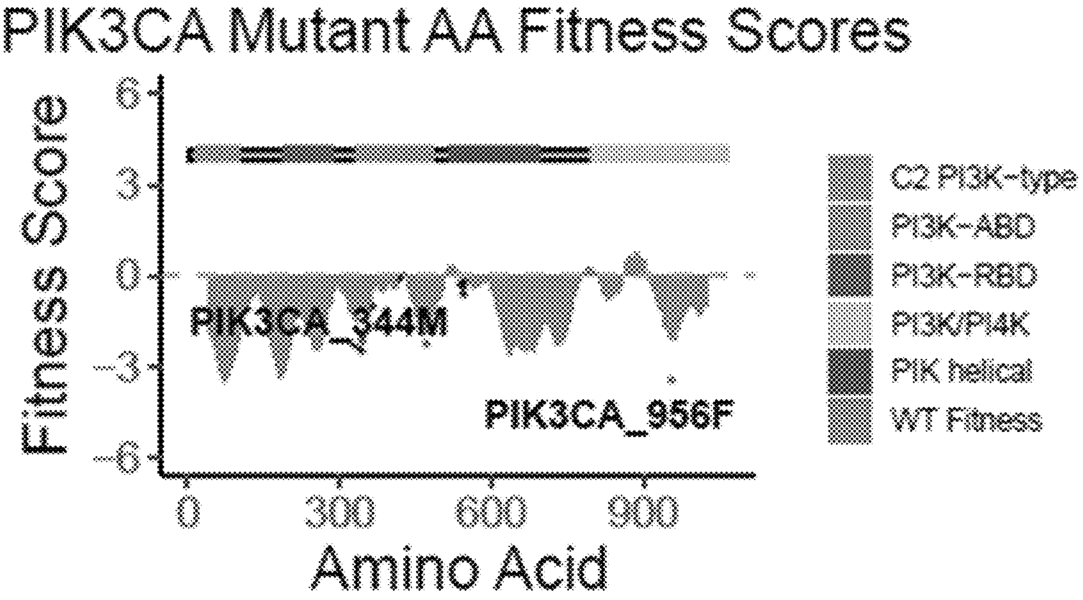
Figure 6G:
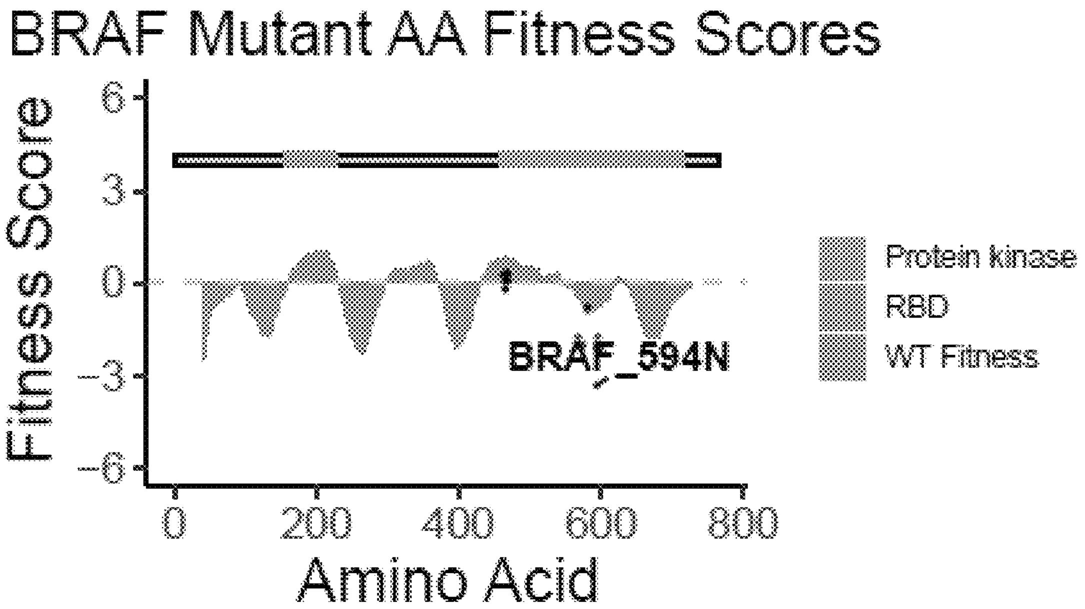
Figure 6G:
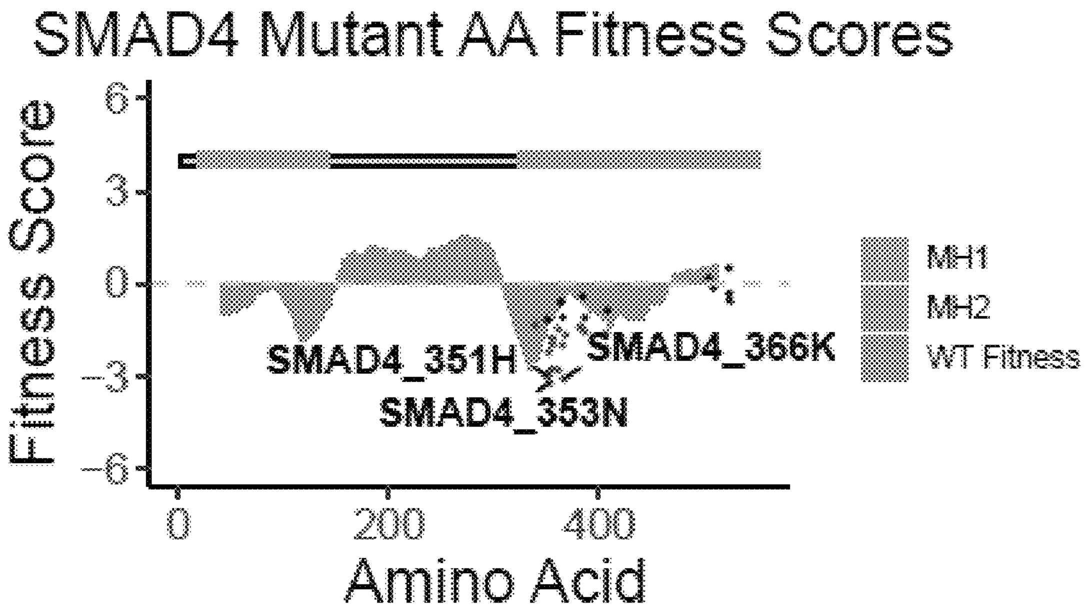

Building on this screen of cancer drivers, a library of peptides derived from high confidence cancer driver mutations identified via The Cancer Genome Atlas sequencing data, was also generated. This screen interrogated 579 mutant residues across 53 cancer driver genes, via 22,724 peptide coding gene fragments (FIG. 2B, E-F, 6E-G). In most cases mutant peptides had a similar effect on cell fitness compared to their wildtype counterparts. However, some mutants such as PIK3CA956F, the aforementioned KRAS61K, and BRAF594N showed markedly more deleterious effects on cell fitness (FIG. 2E, 6G). To further validate that the peptide over-expression platform can identify biophysical features relevant to the protein from which they were derived, the mutant TP53 peptide data was compared with existing TP53 deep mutational scan (DMS) data (FIG. 2F). After first filtering the DMS data for only TP53 mutants with a high magnitude of effect on cell fitness (absolute fitness value >0.5), the fitness of the corresponding mutant peptides was compared to the screen data as described herein. Even with the highly dissimilar screening modalities, significant correlation (Pearson r=0.279; P=0.045) between the predicted mutant TP53 functionality from the DMS data to the mutant TP53 peptide fitness. This indicates TP53 mutants expected to be functional (either through gain of oncogenic function or retention of WT function), generate mutant peptides with functionality consistent with the parental structure from which they were derived. Together, these results highlight a major utility of this approach, e.g., the ability to interrogate user defined peptide sequences as opposed to those present only in WT protein structures.

A similar library of dominant negative peptides was generated against ACE2 as a target to prevent SARs-Cov2 infection (see, SEQ ID NOs: 9460-9489).

Figure 4A:
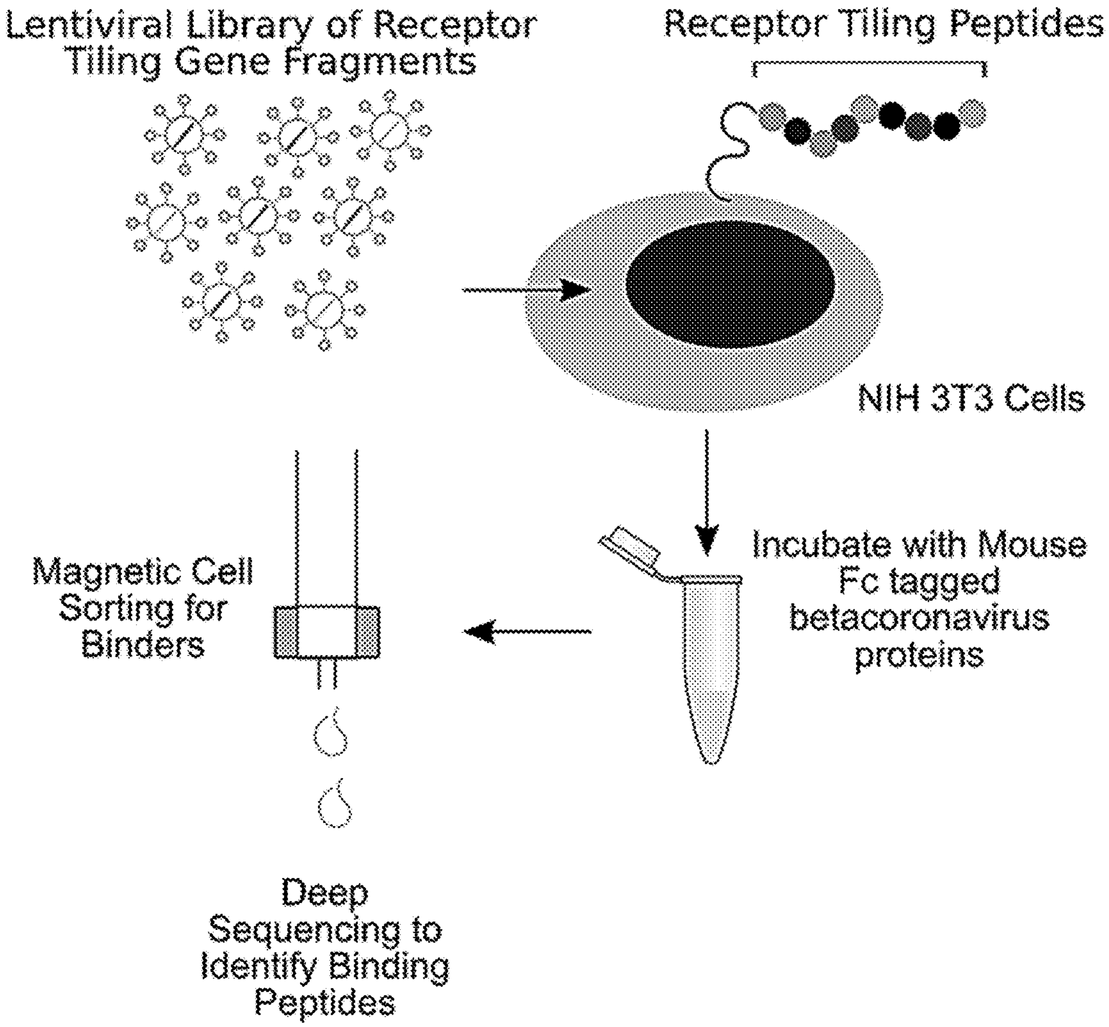
FIG. 4A-E shows PepTile based mapping of Betacoronavirus spike protein and host receptor interactions, and facilitating of downstream peptide bioproduction: (A) Schematic illustrating experimental strategy to probe human receptors for Betacoronavirus binding domains. Peptides derived from receptors (plus homologs) implicated in coronavirus cell entry were expressed on the cell surface, and screened for binding mouse Fc tagged full length coronavirus spike proteins, as well as mouse Fc tagged RBD domains. Enrichment of cells expressing binding peptides was accomplished via magnetic activated cell sorting after incubation with anti-mouse Fc magnetic beads. (B) Fluorescent images showing cell surface localization of HaloTag construct cloned into cell surface expression vector. HEK293T cells were transfected with the cell surface HaloTag construct, and subsequently incubated with AlexaFluor488 labeled HaloTag ligand to visualize protein localization. (C) Plot showing consensus peptides enriched in the bound fraction for both the full-length spike protein as well as the RBD domain. Highly enriched ACE2 derived peptides are highlighted. (D) Hit peptides derived from ACE2 are shown overlaid on the protein crystal structure in complex with SARS-Cov2 spike protein. Shown is ACE2_28; ACE2_72; ACE2_314/ACE2_315, ACE2_654/655; ACE2_591; ACE2_418; ACE2_452. (E) Peptide production protocol to facilitate translation of peptide hits. Tagless peptides conjugated to cell penetrating protein TAT were produced at high purity via fusion to Maltose Binding Protein (MBP), and subsequent cleavage by TEV protease. The protocol makes use of no specialized instruments, and is easily adaptable to alternative cell penetrating motifs or peptide constructs. Ladder has bands marking 10, 15, 20, 25, 37, 50, 75, 100, 150, and 250 kD.
Figure 4B:
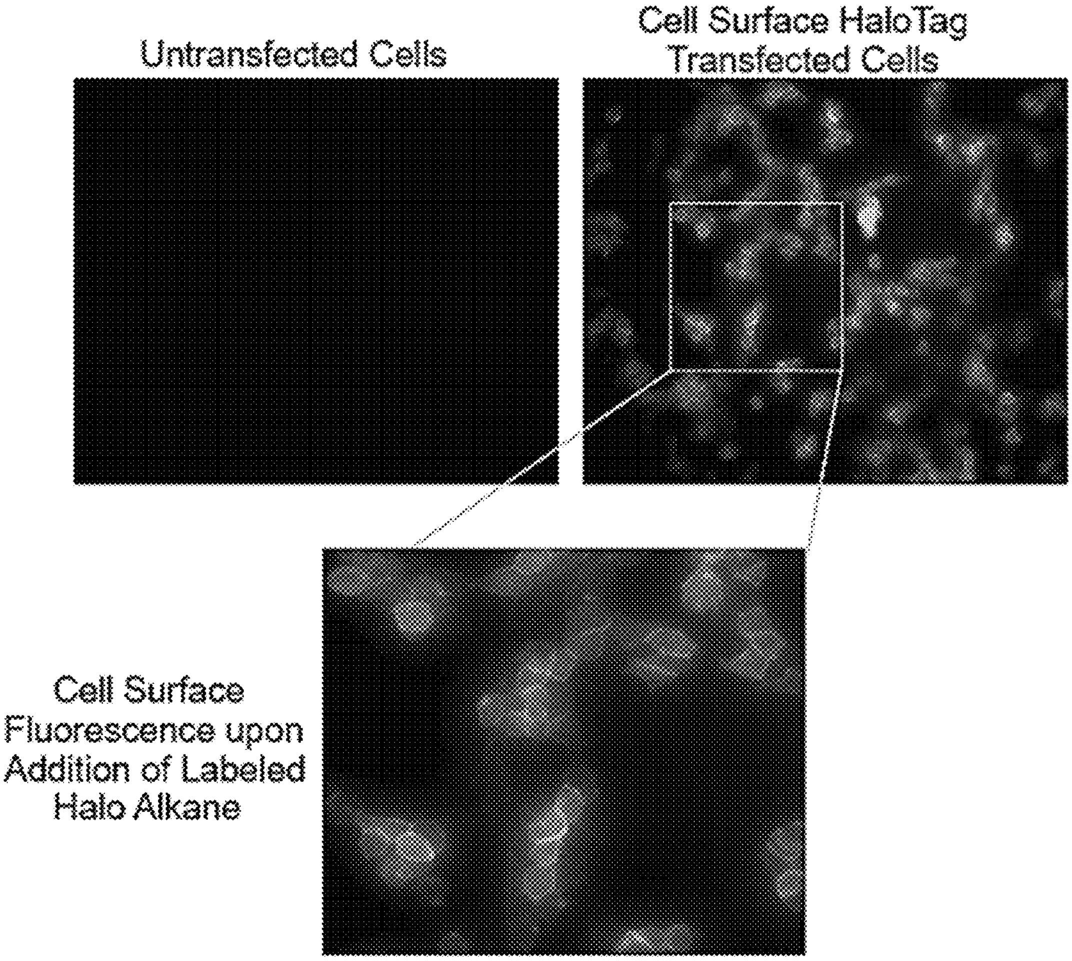
Figure 7A:
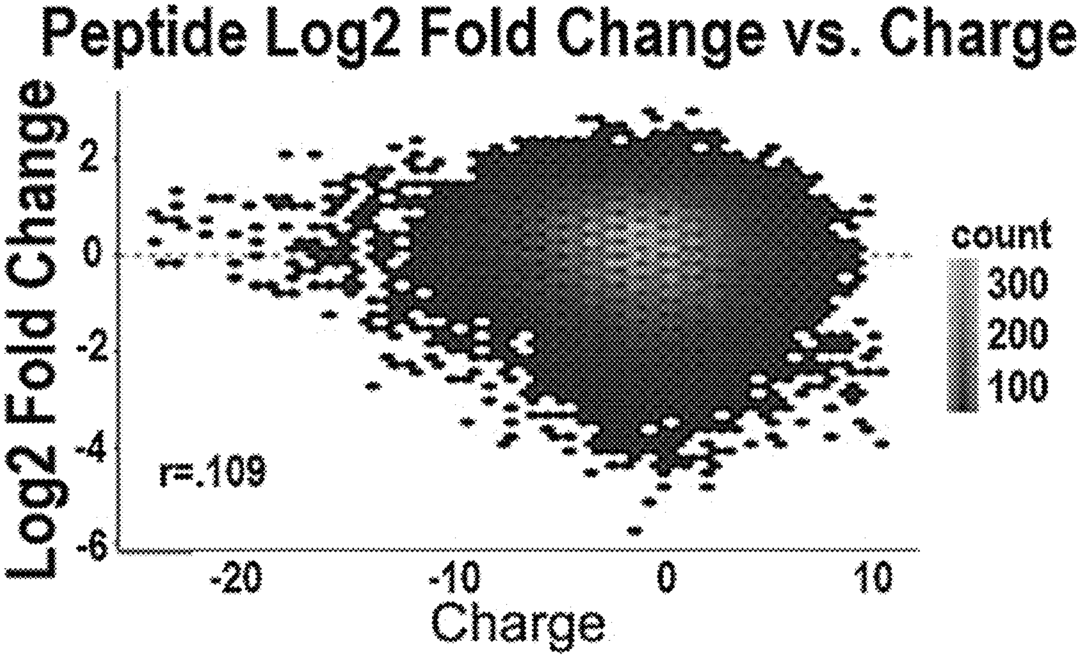
Figure 7B:
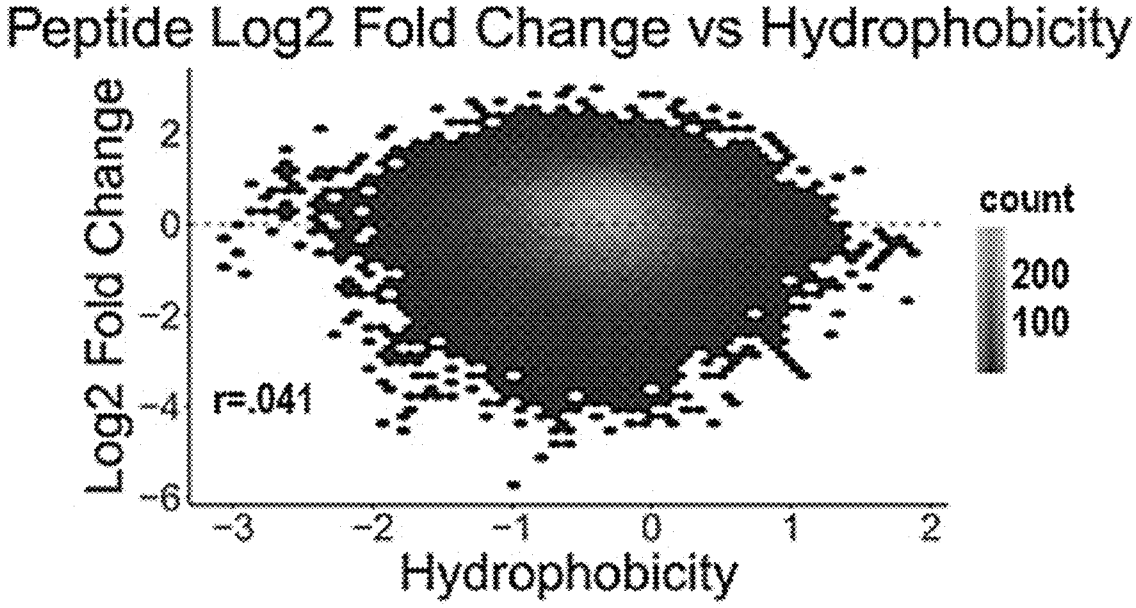
Figure 7C:
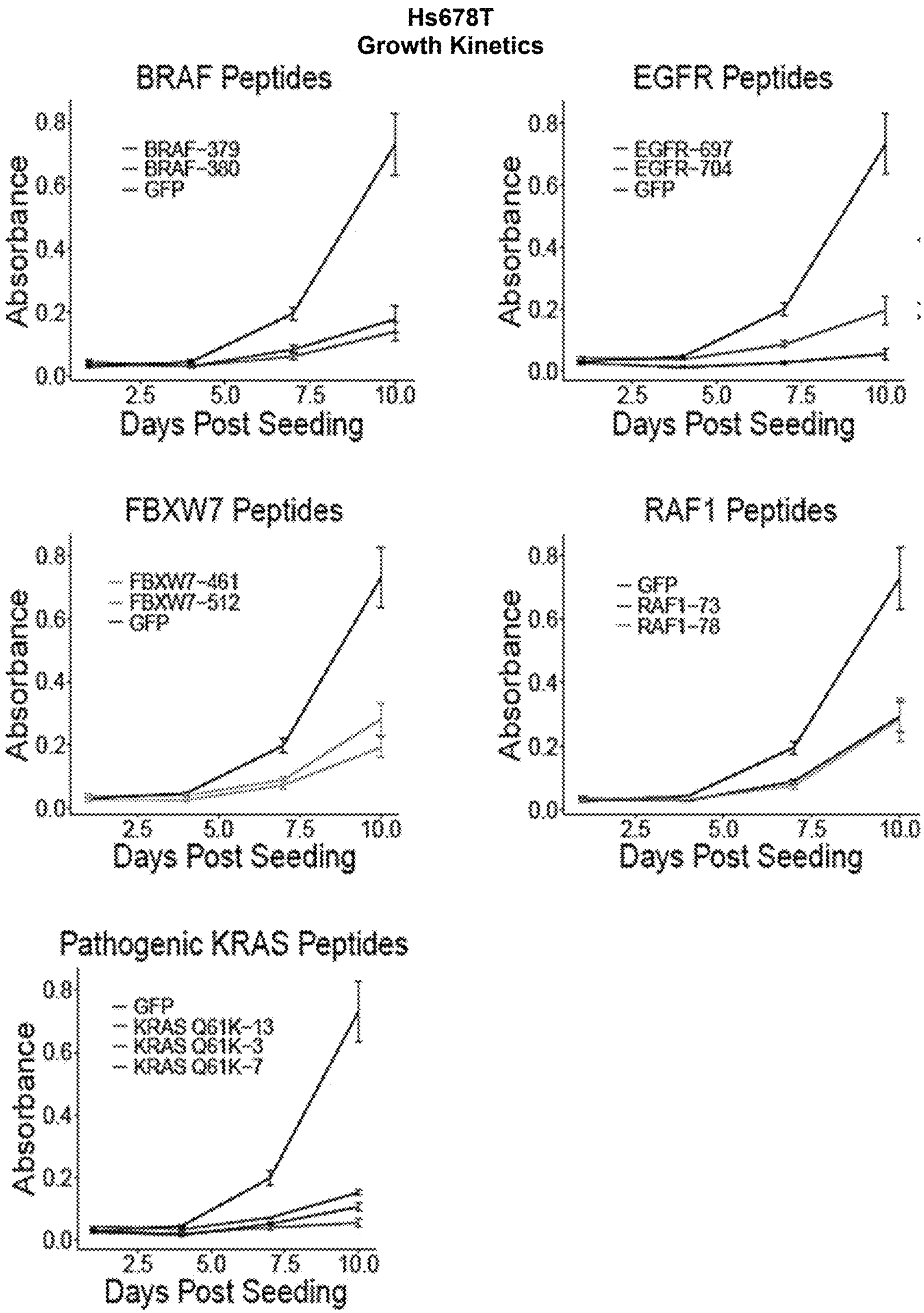
Figure 7D:
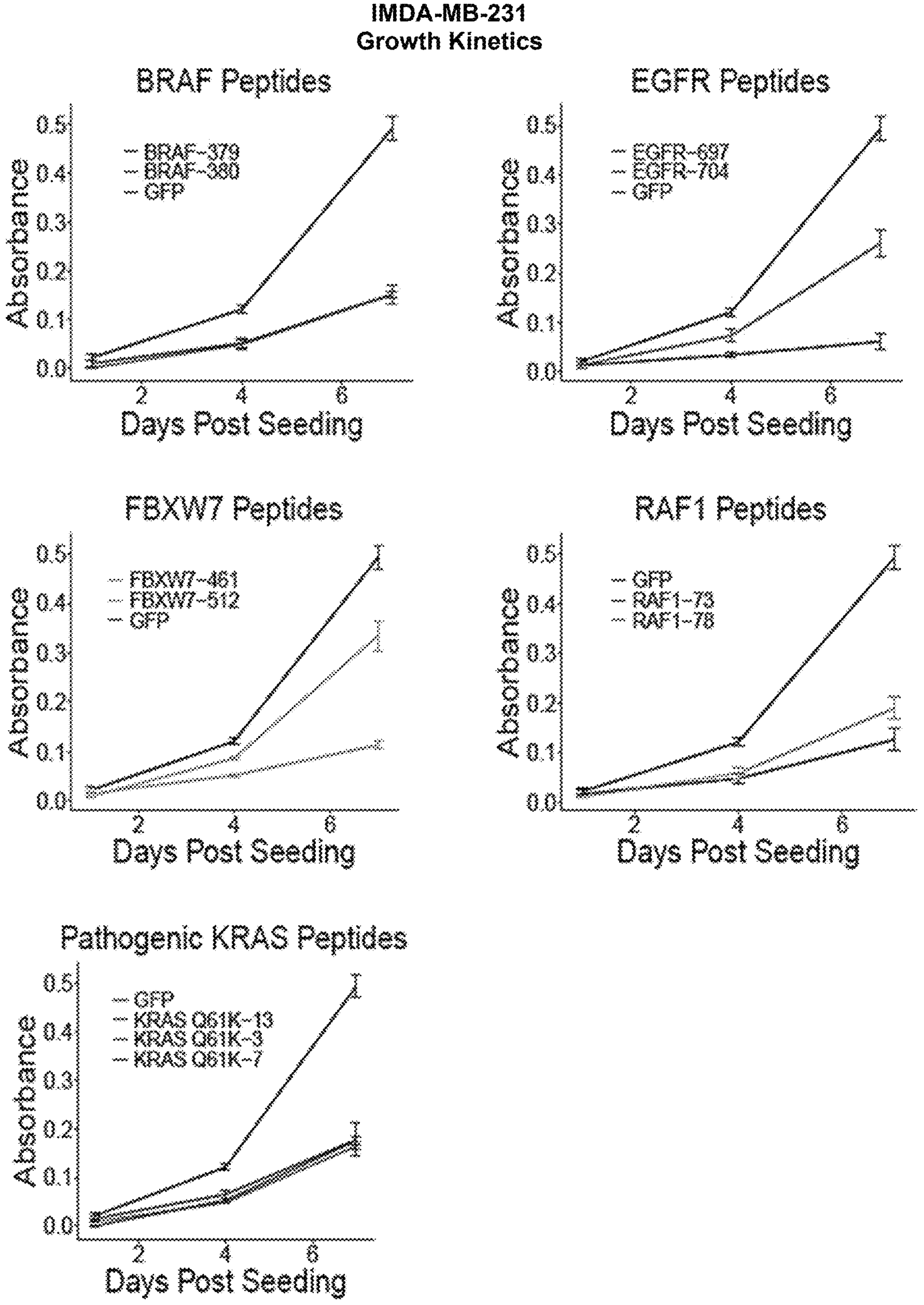

Validation of the anti-proliferative effects of the peptides were tested via a complementary technology other than sequencing. Specifically, after transduction with putative anti-proliferative gene fragments derived from WT proteins, Hs578T cells and MDA-MB-231 cells were seeded in 96 well plates (n=4-8) and grown for 7 days, with proliferation measured via the colorimetric WST-8 assay (FIG. 3A, 7C-D, and Table 6). All peptides tested had significant growth defects in both cell lines compared to infection with the GFP control plasmid. EGFR-697 specifically was deleterious to cell growth in both cell lines. Three peptides derived from the KRAS Q61K mutant protein (KRAS61K-3, KRAS61K-7, and KRAS61K-13) were similarly tested, all of which significantly reduced cell growth in both cell lines (FIG. 4A-B). To test the specificity of these perturbations, MCF-7 cells were transduced with EGFR-697 and RAF1-73. MCF-7 cells show a reduced fitness defect upon overexpression of EGFR-697, consistent with previous reports showing MCF-7 cells are less sensitive than Hs578T and MDA-MB-231 cells to the EGFR inhibitor Gefitinib. As well, HEK293T cells transduced with EGFR-697 and RAF1-73 showed no growth defects, further indicating this screening methodology identifies context dependent inhibitors of cellular proliferation rather than generally toxic peptide motifs.

TABLE 6

Peptides/Proteins validated via lentiviral overexpression

| Gene Name | Amino Acid Sequence |
|---|---|
| BRAF-379 | MIDDLIRDQGFRGDGGSTTGL SATPPASLPGSLTNVKALQK (SEQ ID NO: 9524) |
| BRAF-380 | MDDLIRDQGFRGDGGSTTGLS ATPPASLPGSLTNVKALQKS (SEQ ID NO: 9525) |
| EGFR-697 | MEAPNQALLRILKETEFKKIK VLGSGAFGTVYKGLWIPEGE (SEQ ID NO: 9526) |
| EGFR-704 | MLRILKETEFKKIKVLGSGAF GTVYKGLWIPEGEKVKIPVA (SEQ ID NO: 9527) |
| FBXW7-461 | MTSTVRCMHLHEKRVVSGSRD ATLRVWDIETGQCLHVLMGH (SEQ ID NO: 9528) |
| FBXW7-512 | MRRVVSGAYDFMVKVWDPETE TCLHTLQGHTNRVYSLQFDG (SEQ ID NO: 9529) |
| RAF1-73 | MRNGMSLHDCLMKALKVRGLQ PECCAVFRLLHEHKGKKARL (SEQ ID NO: 9530) |
| RAF1-78 | MLHDCLMKALKVRGLQPECCA VFRLLHEHKGKKARLDWNTD (SEQ ID NO: 9531) |
| KRAS61K-3 | MIQNHFVDEYDPTIEDSYRKQ VVIDGETCLLDILDTAGKEE (SEQ ID NO: 9532) |
| KRAS61K-7 | MFVDEYDPTIEDSYRKQVVID GETCLLDILDTAGKEEYSAM (SEQ ID NO: 9533) |
| KRAS61K-13 | MPTIEDSYRKQVVIDGETCLL DILDTAGKEEYSAMRDQYMR (SEQ ID NO: 9534) |
| DICER1-552 | MRARAPISNYIMLADTDKIKS FEEDLKTYKAIEKILRNKCS (SEQ ID NO: 9535) |
| KRAS-143 | METSAKTRQGVDDAFYTLVRE IRKHKEKMSKDGKKKKKKSK (SEQ ID NO: 9536) |
| MDM2-25 | METLVRPKPLLLKLLKSVGAQ KDTYTMKEVLFYLGQYIMTK (SEQ ID NO: 9537) |
| RASA1-468 | MKDAFYKNIVKKGYLLKKGKG KRWKNLYFILEGSDAQLIYF (SEQ ID NO: 9538) |

RNA-sequencing on Hs578T cells genetically engineered to overexpress the most deleterious gene fragment identified, EGFR-697, were sequenced. 225 genes were differentially expressed (BH adjusted P-value <0.05), and gene set enrichment analysis (GSEA) was performed to identify upregulation and downregulation of genetic pathways. 239 KEGG pathways corresponding to cell signaling and metabolism were tested, with 22 pathways showing significant (False Discovery Rate <0.025) enrichment/depletion in cells expressing EGFR-697 compared to control cells transduced with GFP. Several metabolic pathways relating to oxidative phosphorylation and carbon metabolism were downregulated, consistent with the role of oncogenic EGFR signaling as a driver of metabolic alterations. Furthermore, genes relating to DNA replication were also downregulated, consistent with the observed slow growing phenotype.

Figure 4C:
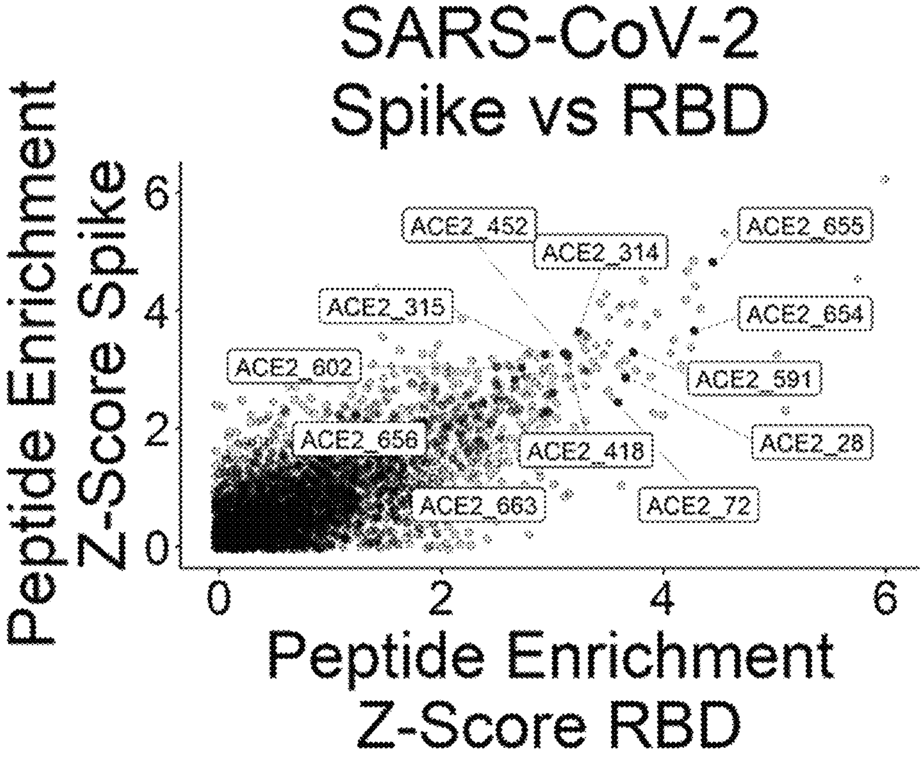

After validating the inhibitory activity of these peptide constructs when overexpressed genetically, experiments were performed to see if the peptides could be exogenously delivered as anti-cancer therapeutics. Towards this, EGFR-697 as well as RAF1-73 peptides were chemically synthesized, and their ability to inhibit cell growth measured when conjugated to the TAT cell penetrating protein transduction domain. (FIG. 4C, Table 6). The best performing peptide from the genetic validations, EGFR-697, maintained its anti-proliferative effects when delivered exogenously (FIG. 2D). The IC50s of the peptide (33.3 μM for Hs578T and 63 μM for MDA-MB-231) were comparable to other FDA approved EGFR inhibitors in these cell lines, highlighting the translational potential of this methodology. Moreover, RAF1-73 was also deleterious to cell growth, with $IC_{50}$ values of 27.0 μM and 32.6 μM for Hs578T and MDA-MB-231 respectively.

Figure 3C:
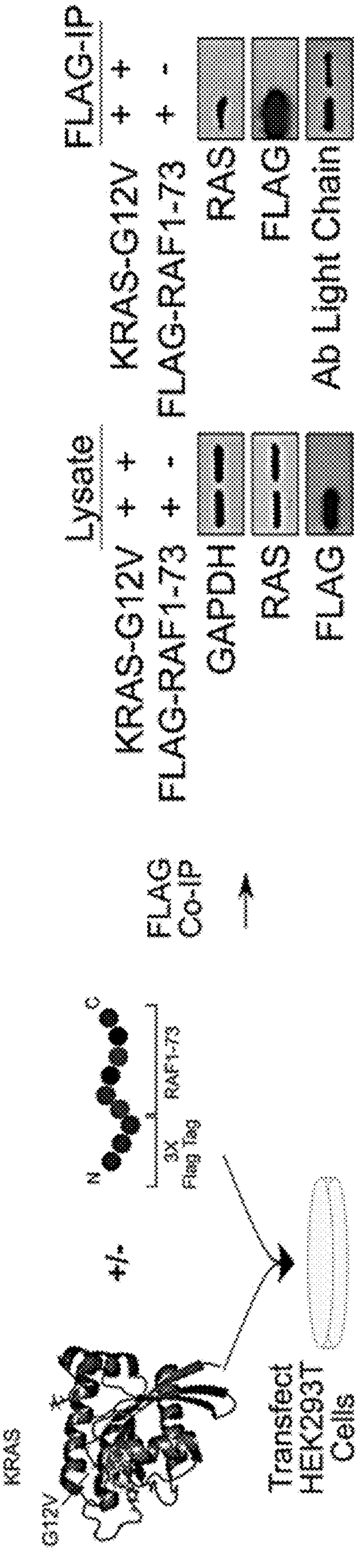
Figure 3D:
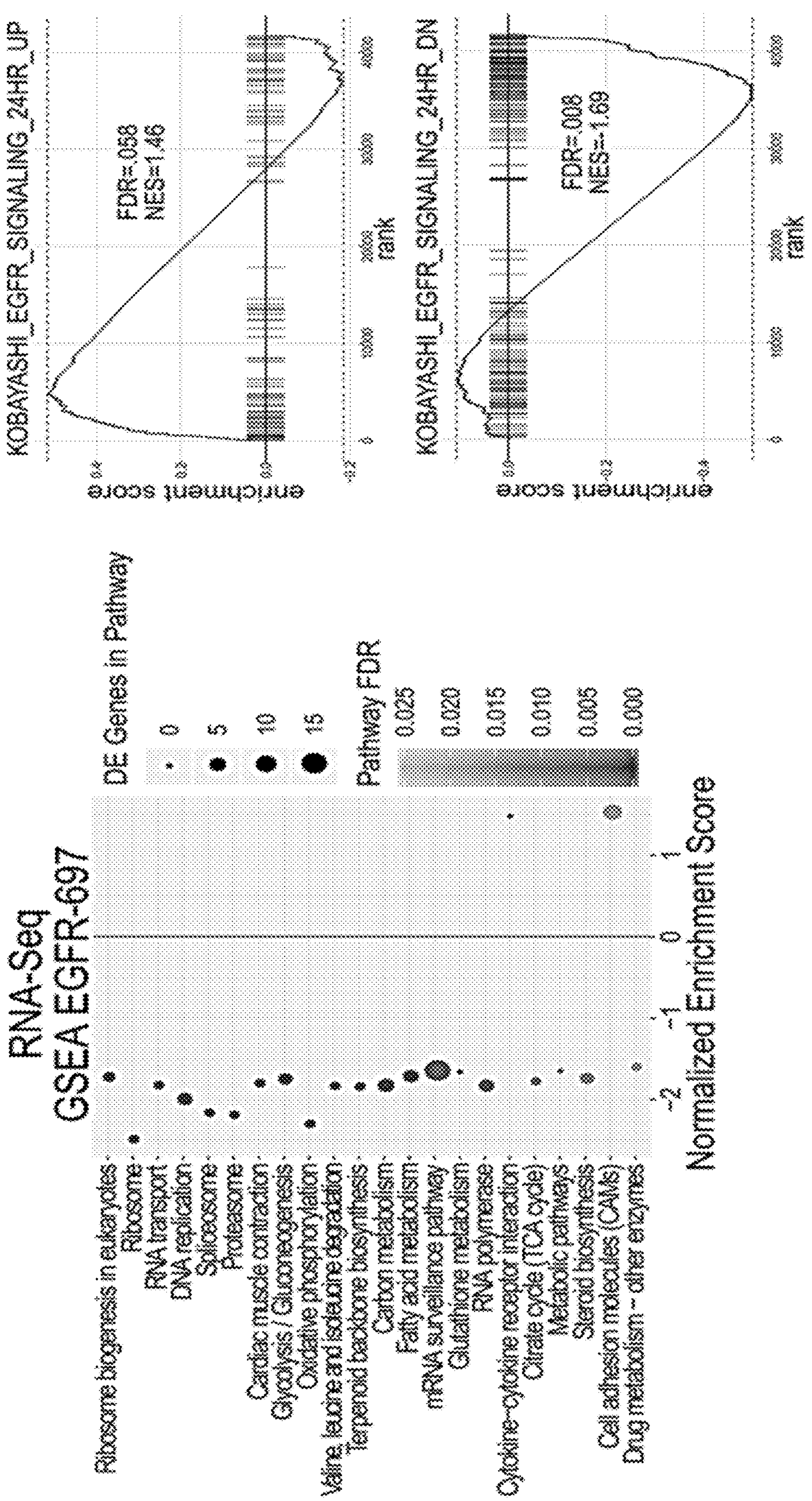
Figure 7E:
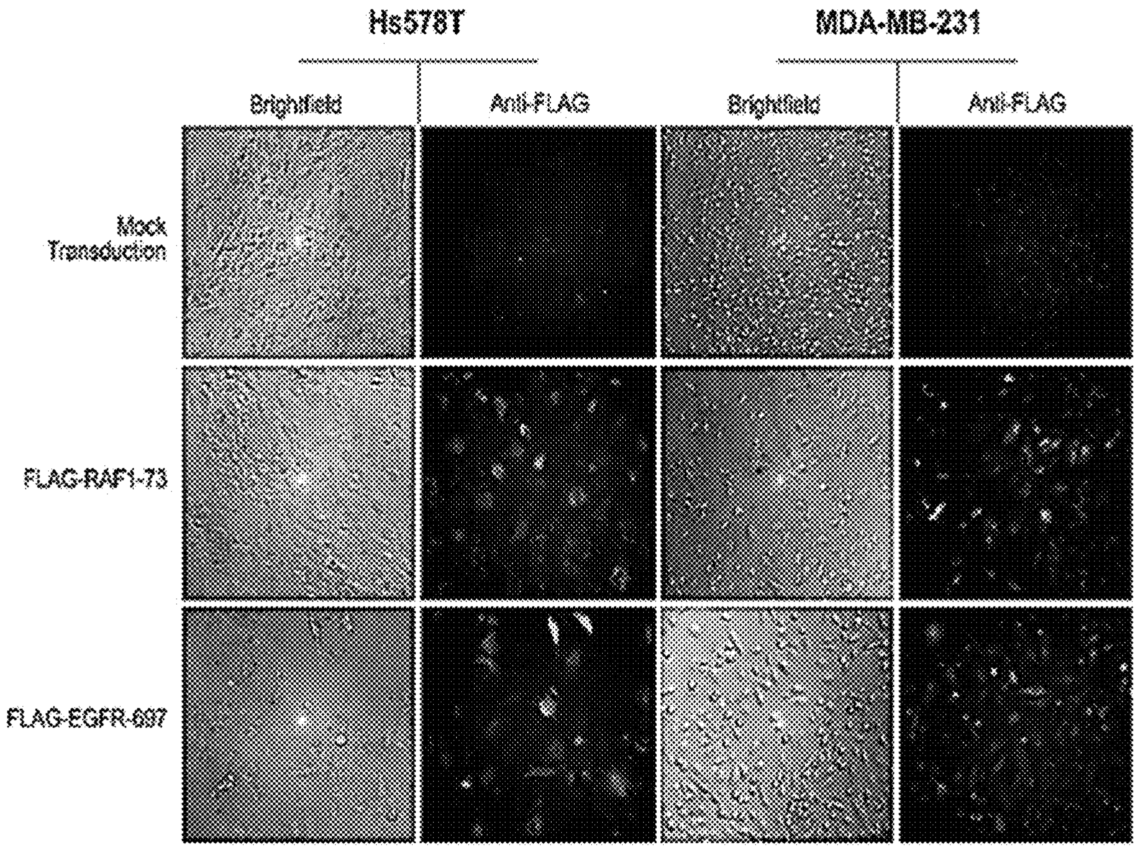

Experiments were performed to validate the hypothesis that the functionality of these putative inhibitory peptides was dependent on the role and structure of the WT protein domain they were derived from. First, 3×FLAG tagged versions of the RAF1-73 and EGFR-697 peptides were generated to verify these constructs had robust expression when overexpressed via lentivirus in Hs578T and MDA-MB-231 cells (FIG. 7E). These peptides showed detectable expression 72 hours after transduction, indicating the EF1αpromoter can drive robust expression of small peptides. After validating that these constructs were well expressed, experiments were performed to determine whether the peptides derived from protein domains retained domain specific biological activities. Specifically, experiments were performed to determine whether the RAF1-73 peptide (derived from the RAF1 Ras binding domain) retained the ability of the full-length domain to bind activated Ras proteins. To evaluate this potential interaction, HEK293T cells were co-transfected with the constitutively active KRAS G12V mutant and 3×FLAG-RAF1-73, then performed a co-immunoprecipitation using anti-FLAG agarose beads (FIG. 3C). Western blot analysis of the immunoprecipitated protein complexes subsequently verified the protein-protein interaction between RAF1-73 and Ras. In order to better understand mechanistically how the EGFR-697 peptide functions, RNA-sequencing was conducted on Hs578T cells modified via lentivirus to overexpress EGFR-697. 225 differentially expressed genes (BH adjusted P-value <0.05) were identified. Gene set enrichment analysis (GSEA) was performed to identify upregulation and downregulation of genetic pathways. 239 KEGG pathways corresponding to cell signaling and metabolism were tested, with 22 pathways showing highly significant (False Discovery Rate <0.025) upregulation/downregulation in cells expressing EGFR-697 compared to control cells transduced with GFP (FIG. 3D). Several metabolic pathways relating to oxidative phosphorylation and carbon metabolism were downregulated, consistent with the role of oncogenic EGFR signaling as a driver of metabolic alterations. Furthermore, genes relating to DNA replication were also downregulated, consistent with the observed slow growing phenotype. In addition to performing GSEA on KEGG pathways, a set of curated genes from the Molecular Signatures Database comprised of genes significantly downregulated/upregulated in H1975 cells upon treatment with an irreversible EGFR inhibitor were also tested. EGFR-697 transduction in Hs578T cells resulted in downregulation of genes identified as downregulated in response to chemical EGFR inhibition, and upregulation of genes identified as upregulated (FDR=0.008 and FDR=0.058 respectively). Collectively, this supports the hypothesis the EGFR-697 peptide can perturb EGFR signaling.

Having demonstrated the applicability of this screening format for intracellular targets, experiments targeted extracellular proteins. Specifically, tiling and assaying gene fragments on the mammalian cell surface could help map receptor ligand interfaces in their native settings and define minimal functional domains, thus complementing in vitro and phage display based strategies. Experiments screening gene fragments of receptors of Betacoronaviruses were performed. This was motivated by 2 aspects: 1) The recent emergence of the SARS-coronavirus 2 (SARS-CoV-2) and its rapid spread that is posing a major global health emergency, and; 2) The ongoing challenges with engineering a therapeutic, including ones anticipated to have the most potency such as vaccines and neutralizing antibodies. It was conjectured that since the virus is an evolving entity but the cognate receptor in humans is relatively constant, a peptide sponge derived from the spike-protein receptor interface (mapped via PepTile screening) could be a putative viral inhibitory agent. Additionally: 1) it could be broadly active against multiple strains; 2) be non-immunogenic as it is human protein derived; 3) will not retain activity of the full-length native protein and thus not disrupt normal physiology if injected into the circulation; and 4) be couplable to protein domains with naturally long serum half-life such as Fc, transferrin or albumin to improve persistence and thereby therapeutic efficacy. Notably, a recent elegant study showed soluble full length ACE2 is able to inhibit SARS-CoV-2 infection, highlighting the potential of human protein scaffolds as a strategy for therapeutic intervention.

Figure 4D:
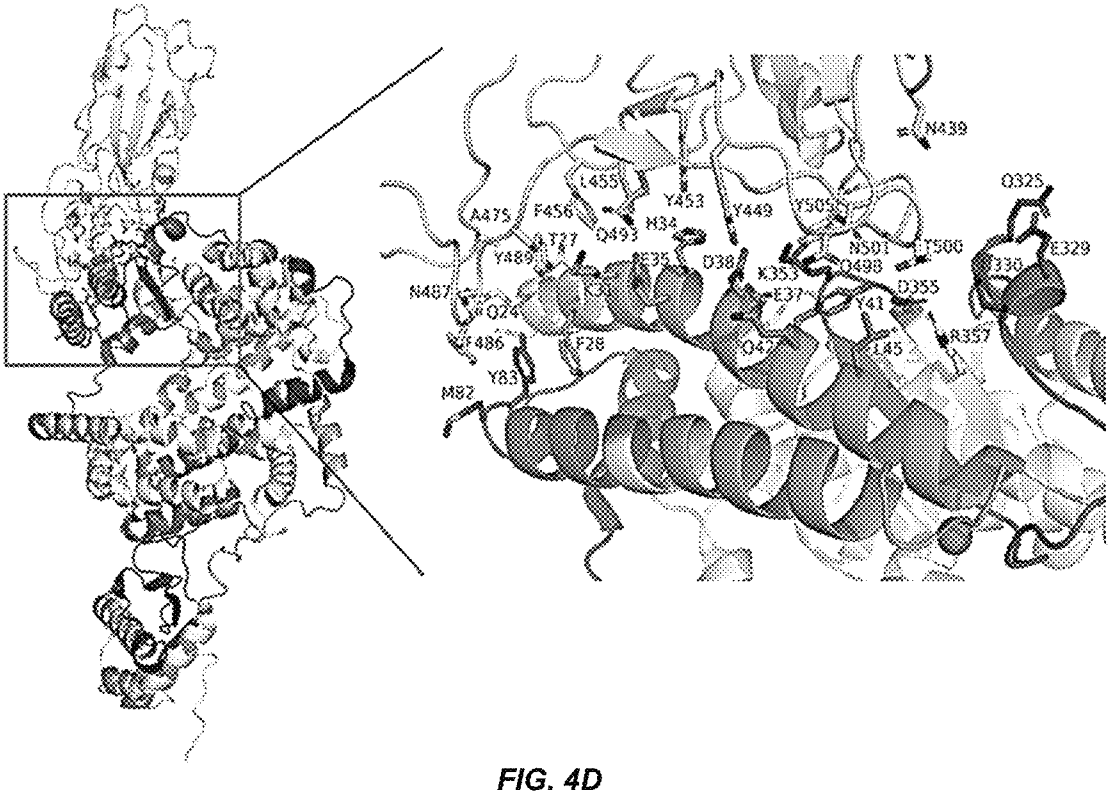

A library of peptides derived from known receptors (and their homologs) of Betacoronaviruses was generated. This screen interrogated 15 proteins, via 11,277 peptide coding gene fragments (FIG. 8B). To express peptides on the cell surface, these were fused to an immunoglobulin K-chain leader sequence at their N terminus and a platelet-derived growth factor (PDGF) transmembrane domain at their C terminus (FIG. 4A-B, 8A). NIH/3T3 cells were used for the screens based on their non-human origin and non-transducability by SARS-CoV-2-Spike protein pseudotyped lentiviruses. Specifically, cells were transduced with the cell-surface peptide library and probed with the SARS-CoV-2 spike protein and RBD domain (bearing a mouse-Fc tag). Cells interacting with the SARS-CoV-2 proteins were separated from the pool using anti-mouse IgG magnetic beads, and their expressed peptides identified via next generation sequencing of the integrated library elements. Binding peptides were identified by comparing the relative abundance of each peptide construct in the bound fraction of cells to the abundance in the starting pool of transduced cells. Several peptides derived from the known SARS-CoV-2 receptor ACE2 were highly enriched across multiple biological replicates, including across two independent SARS-CoV-2 Spike/RBD protein samples (FIG. 4C-D). In addition to peptides derived from known binding proteins such as ACE2 and TMPRSS2, several proteins such as FAP, DPP4, and DPP8 also contained highly significant hits, highlighting putative novel interacting partners of the viral spike protein. Interestingly, the scavenger receptor cysteine rich domain of TMPRSS2 contained a region of peptides which was significantly enriched after selection for spike/RBD binders, illuminating a potential domain implicated in TMPRSS2 substrate recognition.

Figure 4E:
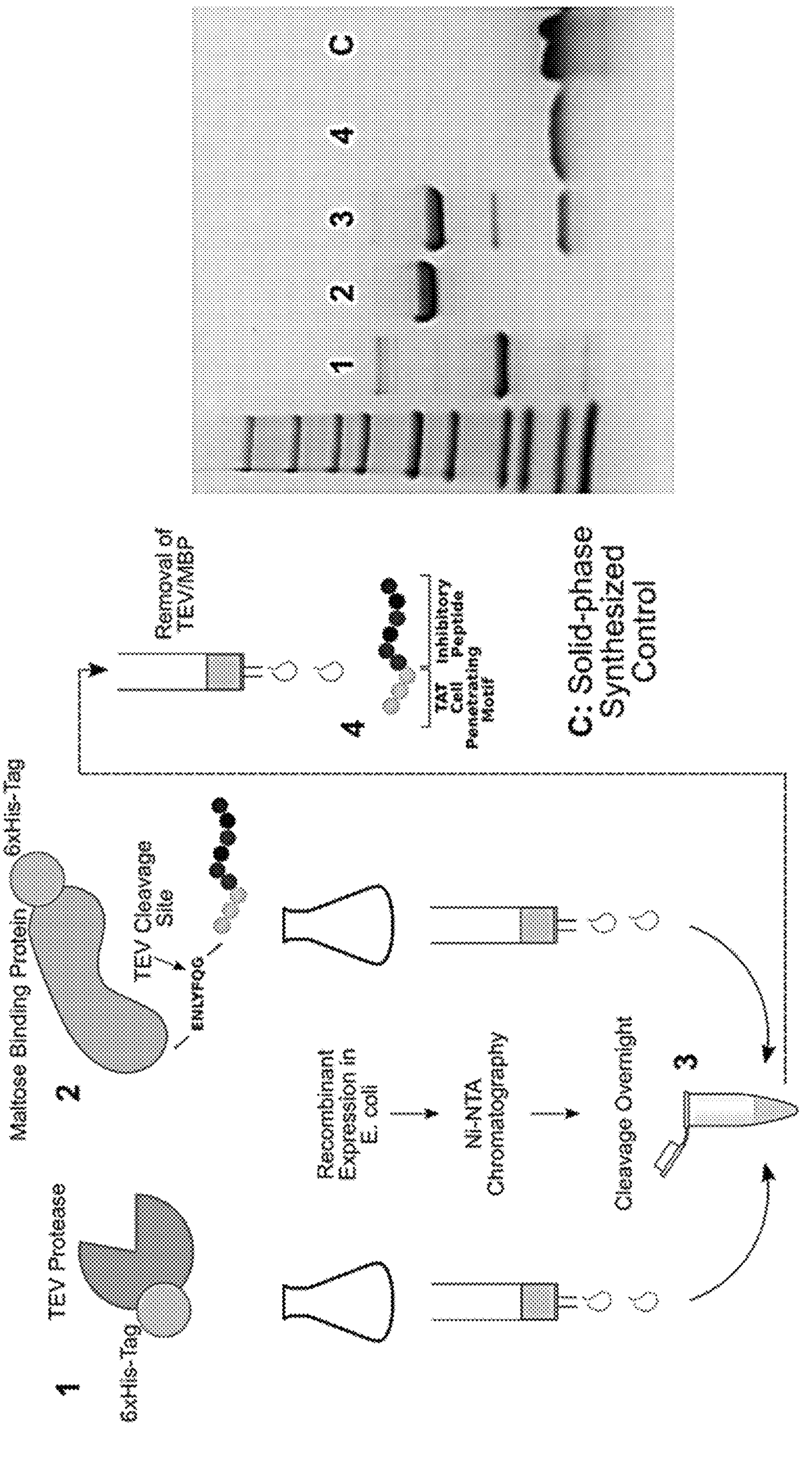
Figure 5A:
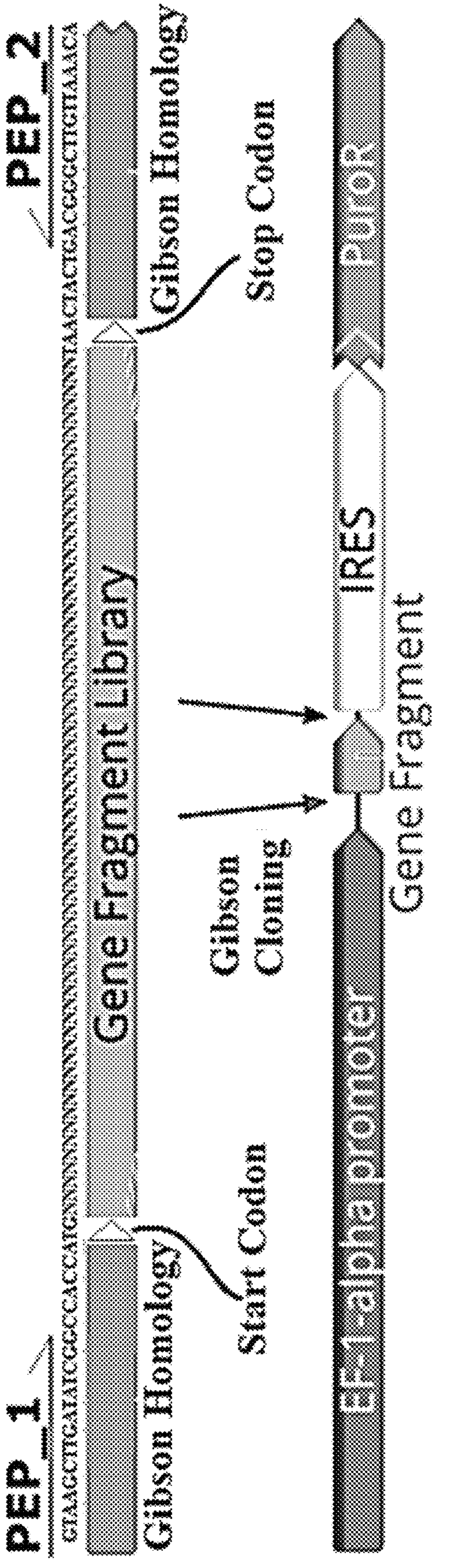
FIG. 5A-E shows a cloning strategy and pilot screen overall analyses: (A) Overview of library construction. Library was ordered as single stranded DNA oligos from Custom Array, and subsequently amplified via PCR to generate gene fragment libraries compatible with Gibson assembly cloning (depicted is SEQ ID NO: 9719). This library was then cloned into pEPIP, with library coverage determined via high throughput sequencing. (B-C) Initial analysis for pooled pilot screen in Hs578T and MDA-MB-231 cells. The majority of peptides tested did not drop out during the fitness screen, although the distribution of peptide log fold change values is skewed towards depletion rather than enrichment. (D-E) The computed fitness scores for the amino acid positions showed good correlation between replicates in both Hs578T and MDA-MB-231. (r=. 536 and r=. 753 respectively). The majority of amino acid positions scored have no significant depletion, with a small subset having a detectable impact on fitness.
Figure 5B:
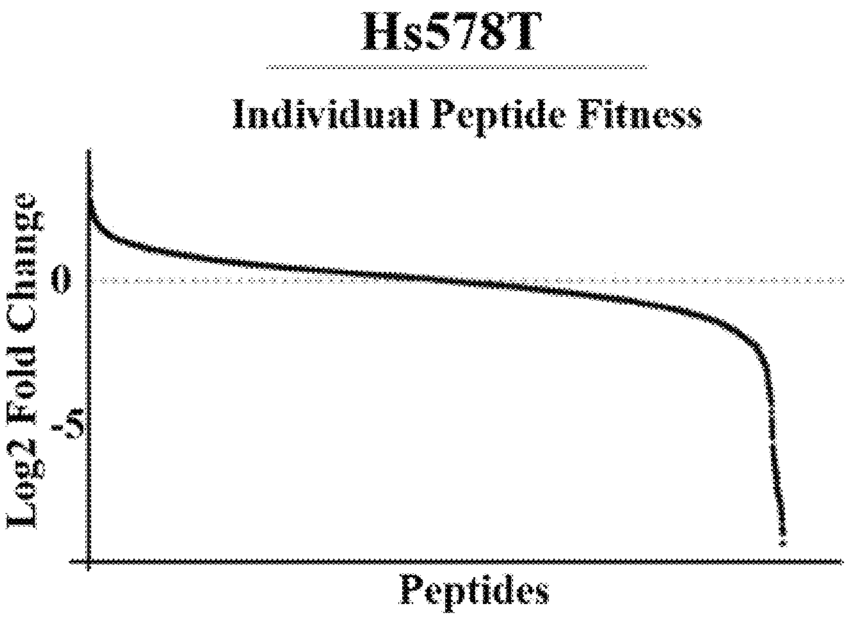
Figure 5C:
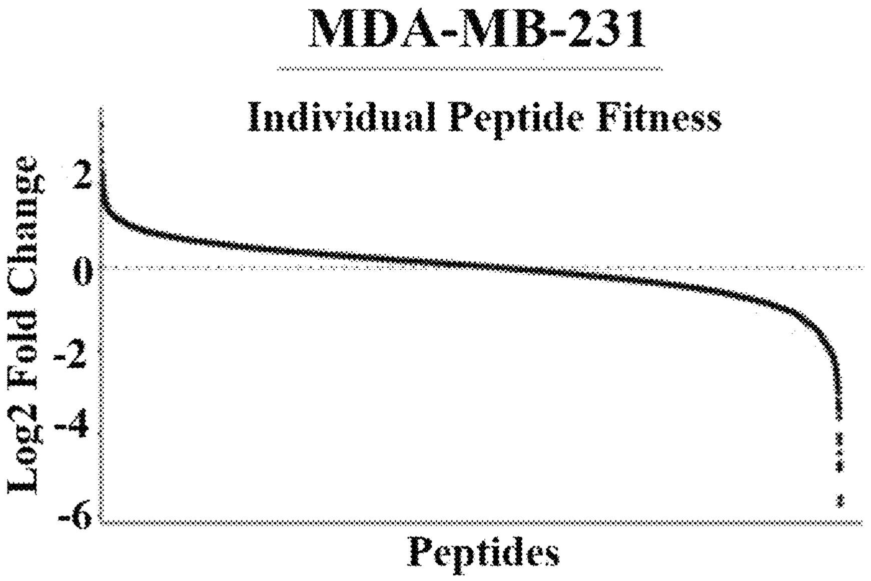
Figure 5D:
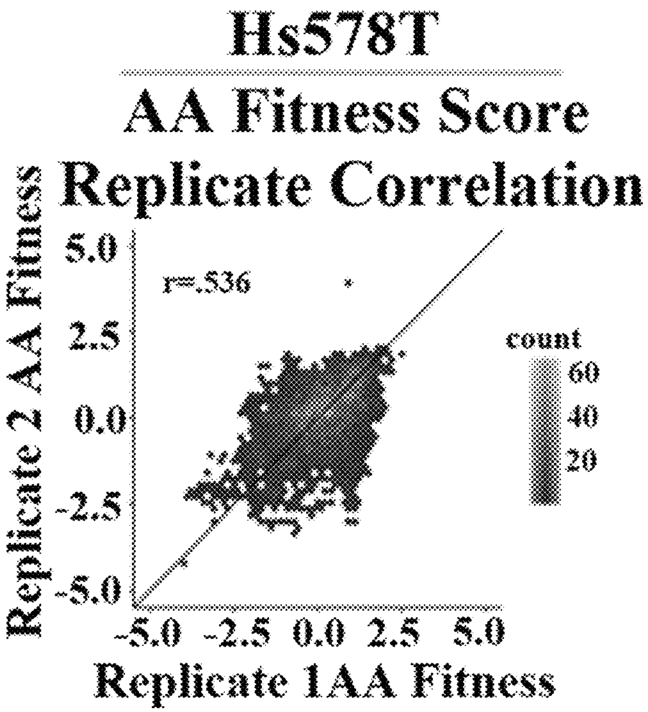
Figure 5E:
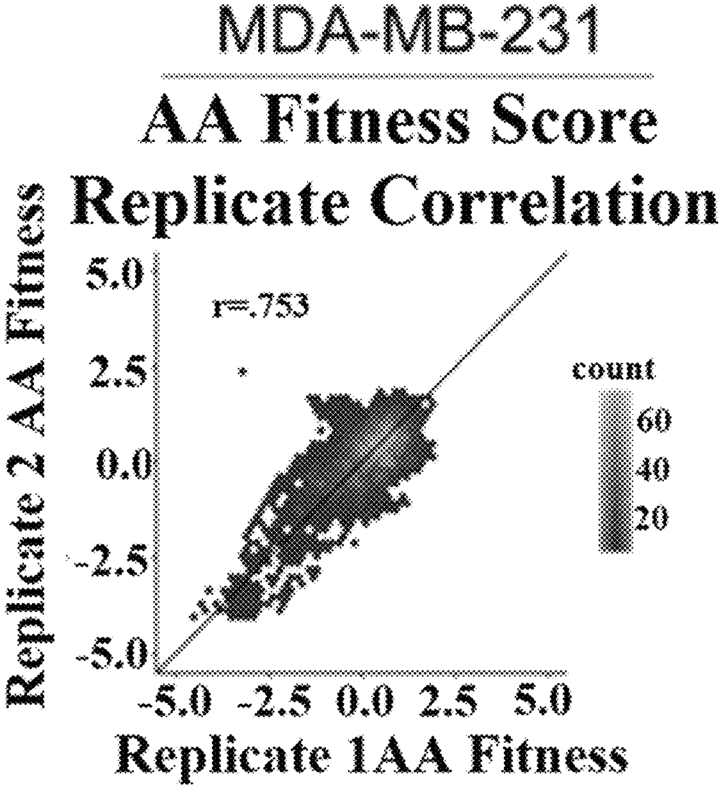

A streamlined peptide purification protocol was developed to facilitate rapid engineering and testing of peptide constructs for translation to medical applications. Specifically, by fusing peptides of interest to a high expressing Maltose Binding Protein (MBP) construct, peptides could be produced in a modular fashion at high yields. By incubating the peptide fusions with TEV protease to cleave the MBP, homogenous preparations of peptide constructs could be produced after subsequent immobilized metal affinity chromatography (IMAC) to remove the free MBP and TEV70. This method was validated by the production of milligram scale quantities of TAT conjugated 3×FLAG peptide, outperforming the costs associated with commercial peptide synthesis (FIG. 4E). Because this method requires no expensive equipment or specialized reagents, it is easily adaptable to labs of any scale, as well as automated medium throughput screening approaches. As peptide constructs will likely require additional engineering to maximize efficacy towards intracellular targets in vivo, this production protocol serves as both a complement to the presented PepTile screening method, as well as a general resource to accelerate the engineering of peptide therapeutics.

Cell Proliferation Assay. The Tat-RAF1-73, Tat-RAF1-78, Tat-EGFR-697 and Tat-Flag peptides were tested for growth inhibition in an in vitro cell proliferation assay. The assay tested the peptides against ten tumor cell lines and four non-tumor cell lines (Primary Fibroblasts, CCD 841 CoN, human umbilical vein cells and Human Hepatocytes). Cells were plated in a 384 well plate and allowed to grow for 24 hrs. Peptides were then added to cultures at a final concentration range of 100 μM-0.2 μM. Cells and peptides were then reacted for 72 hrs, after which the CellTiter-Glo Luminescent Cell Viability Assay kit (Promega) was used to assess cytotoxicity of therapeutic peptides. IC50 values were determined by the percent cell growth of the untreated (vehicle) control calculated from the luminescence signals compared to test wells. The surviving fraction of cells is determined by dividing the mean luminescence values of the test agents by the mean luminescence values of the untreated control. The inhibitory concentration value, IC50, for the test agents and control was estimated using Prism 8 software (GraphPad Software, Inc.) by curve-fitting the data using the non-linear regression analysis.

The results of the cell proliferation assay can be seen in Table 8. Ten cancer cell lines were screened as well as three non-cancer cell types (e.g. primary fibroblasts, CCD 841 CoN, and human hepatocytes). Activity of peptides was identified throughout the cell types including the cancer and non-cancer cell lines. Tat-Raf1-73 and Tat-Raf1-78 had more robust killing, with $IC_{50}$ values ranging from 1.66 μM to 48.87 μM, with Tat-EGFR-697 having more moderate IC50s that ranged from 5 μM to >100 μM (no effect). There was no activity observed in the control Tat-Flag tagged peptides in any of the cells screened.

TABLE 8

| Cell Line | Tissue Type | Mean $IC_{50}$ (μM) Tat-RAF1-73 | Mean $IC_{50}$ (μM) Tat-RAF1-78 | Mean $IC_{50}$ (μM) Tat-EGFR-697 | Mean $IC_{50}$ (μM) Tat-Flag |
|---|---|---|---|---|---|
| H929 | Human Multiple Myeloma | 1.67 | 2.6 | 5.1 | >100 |
| SNU398 | RAF1 mRNA (Log2) 6.07 | 7.91 | 11.06 | 29.23 | >100 |
| Jurkat | RAF1 mRNA (Log2) 6.05 | 7.4 | 9.24 | 41.06 | >100 |
| HUH6-luc | RAF1 mRNA (Log2) 6.05 | 21.31 | 25.32 | 73.48 | >100 |
| Colo205 | Human Colon | 6.12 | 7.28 | 19.81 | >100 |
| A549 | RAF1 mRNA (Log2) Negative | 13.09 | 15.74 | 59.65 | >100 |
| MDA-MB-231 | EGFR mRNA (Log2) 4.78 | 15.5 | 16.13 | 56.62 | >100 |
| HT1376 | EGFR mRNA (Log2) 5. | 25.09 | 26.99 | 95.60* | >100 |
| FaDu | EGFR mRNA (Log2) 6.28 | 20.62 | 26.67 | 89.21 | >100 |
| SK-MEL-5 | EGFR mRNA (Log2) 5.92 | 4.98 | 5.98 | 27.56 | >100 |
| Primary Fibroblasts | Skin Fibroblast | 1.77 | 2.97 | 15.07 | >100 |
| CCD 841 CoN | Normal Human Colon | 40.14 | 48.87 | >100 | >100 |
| Human Hepatocytes | Human Hepatocytes | 4.56 | 6.77 | 11.56 | >100 |
| Human umbilical vein endothelial cells (HUVEC) | Normal endothelial | 4.24 | 4.84 | 14.04 | >100 |

*Value was averaged using >100 μM value for one trial result

It will be understood that various modifications may be made without departing from the spirit and scope of this disclosure. Accordingly, other embodiments are within the scope of the following claims.

SEQUENCE LISTING

The patent contains a lengthy sequence listing. A copy of the sequence listing is available in electronic form from the USPTO web site (https://seqdata.uspto.gov/docdetail?docId=US12807940B2). An electronic copy of the sequence listing will also be available from the USPTO upon request and payment of the fee set forth in 37 CFR 1.19(b)(3).

What is claimed is:

1. A pharmaceutical composition in unit dose form comprising (a) an isolated RAF proto-oncogene serine/threonine-protein kinase (RAF1) peptide or salt thereof, wherein the isolated RAF1 peptide or salt thereof consists of the amino acid sequence selected from the group consisting of SEQ ID NOs: 3465-3467, 4641-4654, 8340-8403, 9530 and 9531; and (b) a non-naturally occurring pharmaceutically acceptable excipient, diluent, or carrier, wherein the RAF1 peptide or salt thereof kills a cancer cell in an in vitro assay; and/or inhibits cancer cell proliferation as determined by an in vitro assay.

2. The pharmaceutical composition in unit dose form of claim 1, wherein the RAF1 peptide or salt thereof kills the cancer cell in the in vitro assay.

3. The pharmaceutical composition in unit dose form of claim 1, wherein the RAF1 peptide or salt thereof comprises a recombinant peptide.

4. The pharmaceutical composition in unit dose form of claim 1, wherein the RAF1 peptide or salt thereof is a stapled peptide or salt thereof, a stitched peptide or salt thereof, a macrocyclic peptide or salt thereof, or any combination thereof.

5. The pharmaceutical composition in unit dose form of claim 4, wherein the stapled peptide comprises a covalent linkage between two amino acid side-chains of the RAF1 peptide or salt thereof.

6. The pharmaceutical composition in unit dose form of claim 1, wherein the RAF1 peptide or salt thereof inhibits cancer cell proliferation in the in vitro assay.

7. The pharmaceutical composition in unit dose form of claim 1, wherein the RAF1 peptide or salt thereof is operably linked to a protein transduction domain (PTD) selected from the group consisting of SEQ ID NO:9490 to 9505.

* * * * *